(12) United States Patent
    Handique et al.

(10) Patent No.: US 10,391,492 B2
(45) Date of Patent: Aug. 27, 2019

(54) SYSTEM AND METHOD FOR ISOLATING AND ANALYZING CELLS

(71) Applicant: Celsee Diagnostics, Inc., Plymouth, MI (US)

(72) Inventors: Kalyan Handique, Ann Arbor, MI (US); Vishal Sharma, Plymouth, MI (US); Priyadarshini Gogoi, Ann Arbor, MI (US); William Chow, Plymouth, MI (US); Austin Payne, Ypsilanti, MI (US); Kyle Gleason, Brighton, MI (US); Brian Boniface, Plymouth, MI (US); John Connolly, Plymouth, MI (US); Sam Tuck, Plymouth, MI (US)

(73) Assignee: Celsee Diagnostics, Inc., Plymouth, MI (US)

( * ) Notice: Subject to any disclaimer, the term of this patent is extended or adjusted under 35 U.S.C. 154(b) by 0 days.

(21) Appl. No.: 16/115,059

(22) Filed: Aug. 28, 2018

(65) Prior Publication Data

US 2019/0064168 A1 Feb. 28, 2019

Related U.S. Application Data

(60) Provisional application No. 62/551,575, filed on Aug. 29, 2017, provisional application No. 62/671,750, filed on May 15, 2018.

(51) Int. Cl.
| | |
|---|---|
| *C12Q 1/68* | (2018.01) |
| *B01L 3/00* | (2006.01) |
| *C12M 1/00* | (2006.01) |
| *G01N 33/574* | (2006.01) |
| *G01N 15/14* | (2006.01) |
| *G01N 33/543* | (2006.01) |
| *G01N 33/569* | (2006.01) |
| *C12Q 1/6816* | (2018.01) |
| *C12Q 1/6886* | (2018.01) |
| *G01N 15/10* | (2006.01) |

(52) U.S. Cl.
CPC ....... *B01L 3/502761* (2013.01); *C12M 47/04* (2013.01); *C12Q 1/6816* (2013.01); *G01N 15/1434* (2013.01); *G01N 15/1484* (2013.01); *G01N 33/543* (2013.01); *G01N 33/569* (2013.01); *G01N 33/574* (2013.01); *B01L 3/502715* (2013.01); *B01L 3/527* (2013.01); *B01L 2200/0668* (2013.01); *B01L 2300/0636* (2013.01); *B01L 2300/0819* (2013.01); *B01L 2300/0829* (2013.01); *B01L 2300/0851* (2013.01); *B01L 2400/0406* (2013.01); *C12Q 1/6886* (2013.01); *G01N 2015/1006* (2013.01); *G01N 2015/149* (2013.01)

(58) Field of Classification Search
None
See application file for complete search history.

(56) References Cited

U.S. PATENT DOCUMENTS

| | | |
|---|---|---|
| 7,588,672 B2 | 9/2009 | Unger et al. |
| 8,628,923 B2 | 1/2014 | Hamilton et al. |
| 8,802,367 B2 | 8/2014 | Taniguchi et al. |
| 9,194,001 B2 | 11/2015 | Brenner |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,637,799 B2 | 5/2017 | Fan et al. |
| 9,701,998 B2 | 7/2017 | Hindson et al. |
| 9,708,659 B2 | 7/2017 | Fodor et al. |
| 9,757,707 B2 | 9/2017 | Husain et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 2009/0258383 A1 | 10/2009 | Kovac et al. |
| 2015/0133319 A1 | 5/2015 | Fu et al. |
| 2015/0204864 A1 | 7/2015 | Fan et al. |
| 2015/0376609 A1 | 12/2015 | Hindson et al. |
| 2016/0024572 A1 | 1/2016 | Shishkin et al. |
| 2016/0024761 A1 | 1/2016 | Korb |

(Continued)

FOREIGN PATENT DOCUMENTS

| | | |
|---|---|---|
| EP | 2414548 A2 | 2/2012 |
| WO | 2018013723 A1 | 1/2018 |
| WO | 2018058073 A2 | 3/2018 |

OTHER PUBLICATIONS

International Search Report for PCT Application No. PCT/US2018/048353 dated Nov. 5, 2018.

*Primary Examiner* — James Martinell
(74) *Attorney, Agent, or Firm* — Jeffrey Schox

(57) ABSTRACT

A system and method for isolating and analyzing single cells, wherein the system includes: an array of wells defined at a substrate, each well including an open surface and a well cavity configured to capture cells in one of a single-cell format and single-cluster format, and a fluid delivery module including a fluid reservoir superior to the array of wells through which fluid flow is controlled along a fluid path in a direction parallel to the broad face of the substrate; and wherein the method includes: distributing a population of cells and a population of non-cell particles across the array of wells through the fluid reservoir to increase capture efficiency of individual cell-particle pairs within the array of wells, and processing the captured cell-particle pairs at the set of wells.

20 Claims, 36 Drawing Sheets

(56) References Cited

U.S. PATENT DOCUMENTS

| | | |
|---|---|---|
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0199838 A1 | 7/2016 | Handique et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2017/0044525 A1 | 2/2017 | Kaper et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |

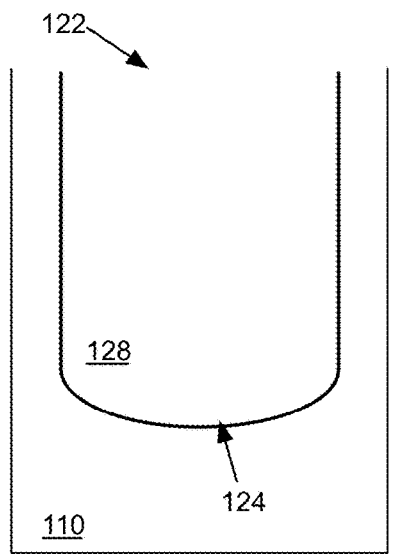
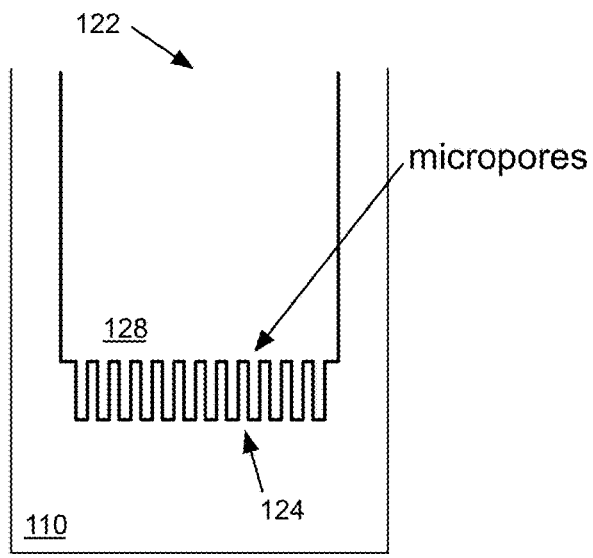
FIGURE 5A  FIGURE 5B
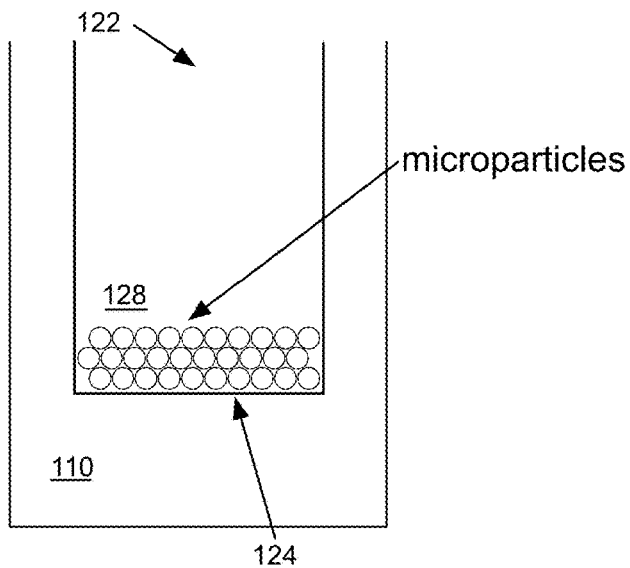
FIGURE 5C

Single Cell Comprehensive Analysis

User slides substrate platform to lock into place

User places substrate platform on heating element thermal control module 190 (thermocycler surface)

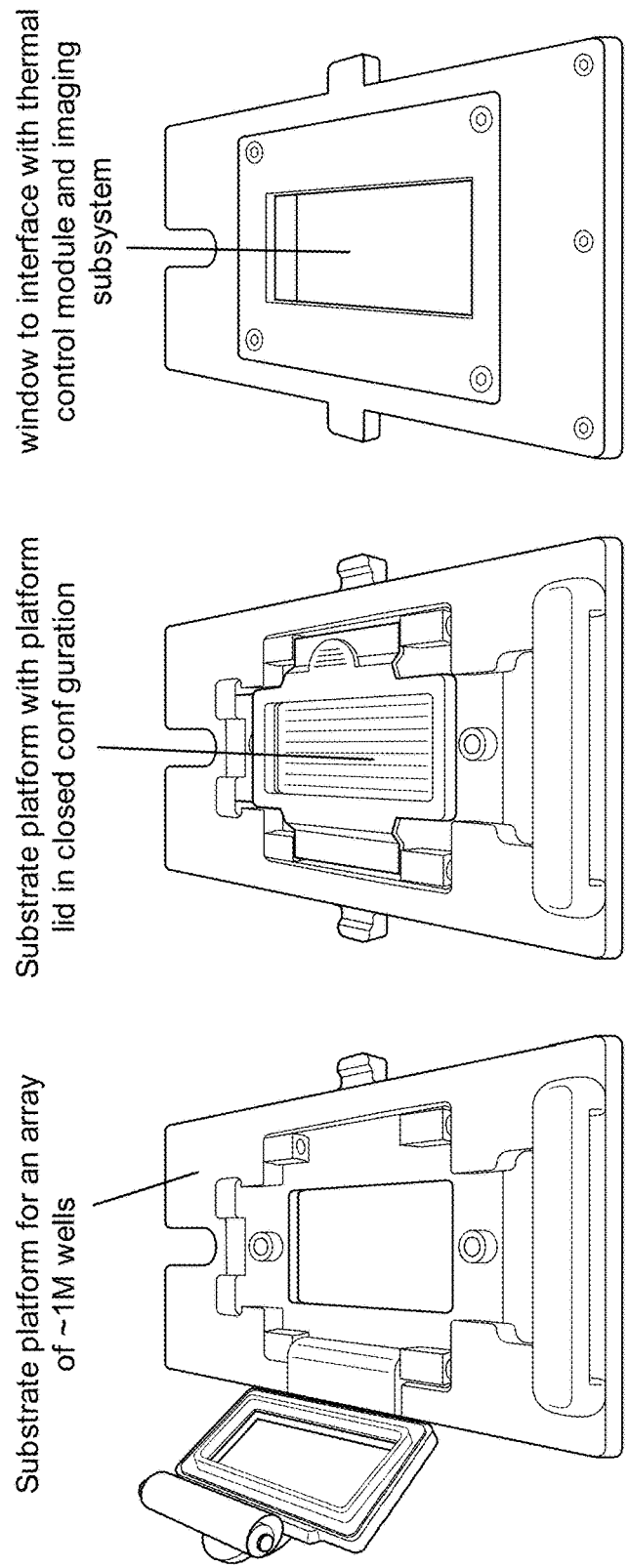

SYSTEM AND METHOD FOR ISOLATING AND ANALYZING CELLS

CROSS-REFERENCE TO RELATED APPLICATIONS

This application claims the benefit of U.S. Provisional Application No. 62/551,575 filed on 29 Aug. 2017 and U.S. Provisional Application No. 62/671,750 filed on 15 May 2018, which are both incorporated in their entirety herein by this reference.

TECHNICAL FIELD

This invention relates generally to the cell sorting and analysis field, and more specifically to a new and useful system and method for capturing and analyzing cells within the cell sorting field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting and genetic sequencing systems are becoming highly desirable. However, conventional technologies for cell capture systems posses various shortcomings that prevent widespread adoption for cell-specific testing. For example, flow cytometry requires that the cell be simultaneously identified and sorted, and limits cell observation to the point at which the cell is sorted. Flow cytometry fails to allow for multiple analyses of the same cell within a single flow cytometry workflow, and does not permit arbitrary cell subpopulation sorting. In other examples, conventional microfluidic devices rely on cell-specific antibodies for cell selection, wherein the antibodies that are bound to the microfluidic device substrate selectively bind to cells expressing the desired antigen. Conventional microfluidic devices can also fail to allow for subsequent cell removal without cell damage, and only capture the cells expressing the specific antigen; non-expressing cells, which could also be desired, are not captured by these systems. Such loss of cell viability can preclude live-cell assays from being performed on sorted or isolated cells. Cellular filters can separate sample components based on size without significant cell damage, but suffer from clogging and do not allow for specific cell identification, isolation of individual cells, and retrieval of identified individual cells. Other technologies in this field are further limited in their ability to allow multiplex assays to be performed on individual cells, while minimizing sample preparation steps and overly expensive instrumentation.

In the field of single cell analysis, the isolation, identification and genetic analysis of rare cells, such as cancer stem cells, currently suffer limitations in accuracy, speed, and throughput. Furthermore, many systems do not maintain the viability and/or quality of living cells or biological materials extracted from cells, as typical methods for identification of cells during the isolation process necessitates fixation, staining, or an additional biochemical process at higher temperatures, which may damage the cell and/or its genetic material, in addition to slowing processing speed. Thus, there is a need in the cell sorting field to create new and useful systems and methods for isolating and analyzing cells, which are able to maximize viability of cells and their intracellular components, including biomolecules such as messenger RNA, for downstream analysis. Furthermore, cell isolation workflows that further include molecular indexing of biomolecules and processing of genetic transcripts can provide several benefits for improving throughput and accuracy for applications in cellular analysis, including massively parallel RNA sequencing for full-length mRNA, whole genomes and/or single-cell exomes. To date, there are no systems and/or methods that facilitate single cell isolation and DNA/RNA sequencing library construction on a single, unified device. The system and method described herein address these limitations by integrating functions such as single-cell capture, biomolecule labeling, fluid delivery, and temperature modulation, in order to enable more advanced biochemical processes to be performed on individual cells within the same array of wells used to capture the cells (e.g., reverse transcription, polymerase chain reaction, single cell genome (DNA/RNA) sequencing), thereby vastly improving capture efficiency for desired cells and increasing speed and analytical capabilities for single-cell experimental workflows.

BRIEF DESCRIPTION OF THE FIGURES

FIGS. 5A-5C depict variations of a portion of a system for isolating and analyzing cells;

FIG. 32A-32C depicts an example of a variation of a portion of a system for isolating and analyzing cells;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
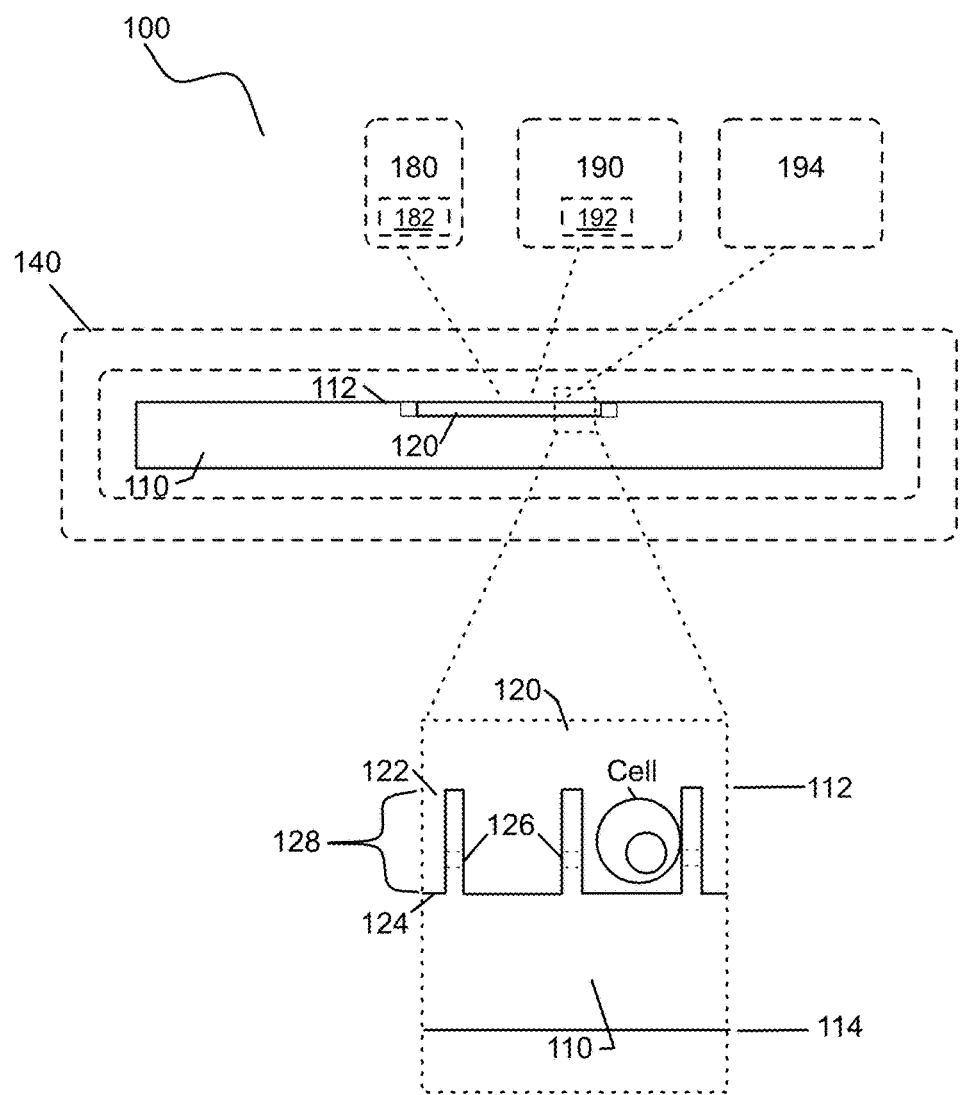
FIG. 1 is a schematic representation of an embodiment of a portion of a system for isolating and analyzing cells.

As shown in FIG. 1, a system 100 for isolating and analyzing a set of cells comprises: a substrate 110 having a broad surface; an array of wells 120 defined at a first side 112 (e.g., upper broad surface) of the substrate, each well 128 in the array of wells 120 including an open surface 122 defined at the first side 112, a base surface 124 defined within the substrate proximal a second side 114 (e.g., lower broad surface) directly opposing the first side 112, and a set of walls 126 extending between the base surface 124 and the open surface 122 to form a well cavity 128 of the well 128. The array of wells 120 can be arranged in an active region 116 of the substrate, or in any other suitable arrangement. To facilitate sample or fluid 40 delivery to the array of wells 120, the system 100 can further include a fluid delivery module 140 configured to couple to the substrate no and transfer a sample containing the set of cells and/or another fluid 40 to the array of wells 120. Additionally or alternatively, the system 100 can include a flow control subsystem (e.g., pressure pump system) 180 configured to control fluid 40 (e.g., biological sample, process reagent, solution containing non-cell particles) flow (e.g., direction, velocity, volume of the fluid) through the system 100, as well as any other suitable flow through the system requiring control and/or actuation. Additionally or alternatively, the system 100 can include a thermal control module 190 for controlling the temperature of portions of the system 100. Additionally or alternatively, the system 100 can include an imaging subsystem 194 configured to perform optical imaging, illumination, or irradiation of the contents of the array of wells 120, and to enable identification, localization, and quantification of cells retained by wells of the array of wells 120. Additionally or alternatively, the system 100 can include an extraction module that can extract one or more: target cells, particles, cell-particle pairs, genetic complexes, and/or genetic products from the array of wells. However, variations of the system 100 can include any other suitable component in any suitable configuration and/or combination, as described in U.S. application Ser. No. 15/333,420 entitled "Cell Capture System and Method of Use" and filed 25 Oct. 2016, U.S. application Ser. No. 14/208,298 entitled "System for capturing and analyzing cells" and filed 13 Mar. 2014, and U.S. application Ser. No. 14/289,155 entitled "System and Method for Isolating and Analyzing Cells" and filed 28 May 2014, which are each incorporated in their entirety by this reference.

The system 100 functions to isolate, capture, retain, and analyze cells of a cell population 20, in at least one of single-cell format and single-cluster format, at known, addressable locations, and further to facilitate performance of multiple single-cell assays that can be performed on individual target cells (e.g., rare cells in a biological sample) or clusters of cells (e.g., doublets, triplets). In preferred embodiments, the system 100 functions to facilitate the preparation of genetic libraries (e.g., cDNA generated from captured mRNA from lysed target cells, amplified cDNA, amplified DNA) of captured single cells for sequencing proximately following, and within the same device, as cell capture. Once cells are captured in defined locations determined by single cell capture wells, the fluid delivery module of the system 100 can be used to provide and deliver reagents simultaneously, sequentially, and/or in repetition to enable a variety of cellular, sub-cellular or molecular reactions to be performed in each of the single cells/cell clusters. Additionally or alternatively, the system 100 can function to capture and process non-cell particles (e.g., nucleic acid material, other biological material, other non-biological material, particles containing molecular probes or reagents, etc.), as well as combinations of single cells and single non-cell particles (e.g., a cell-particle pair). Furthermore, the system 100 can enable controlled and rapid thermal modulation of the array of wells and additionally or alternatively of the fluid 40 delivered to the array of wells (e.g., heating and cooling cycles from 95° C. to 5° C.), to maintain cell or biological material viability, increase efficiency of biological assays, and perform a variety of biochemical processes within the set of wells. The system 100 can also allow optical interrogation and detection of events on each of the captured cells at a single cell/single cluster level. The system 100 can additionally or alternatively enable selective release and/or selective removal of one or more of the captured cells or non-cell particles for further processing and analysis. In some embodiments, the system 100 can confer the benefits of real-time cell tracking, viable cell retrieval, biochemical processes (e.g., cell lysis, cell fixation, polymerase chain reaction, reverse transcription, etc.) and selective downstream molecular analysis (e.g., electrophoresis, sequencing, fluorescence imaging), either in the same microfluidic chip or off-chip. In some embodiments, the system 100 can be used to capture circulating tumor cells (CTCs) and subpopulations of CTCs, such as circulating stem cells (CSCs), but can additionally or alternatively be used to capture any other suitable cell (e.g., erythrocytes, monocytes, macrophages, osteoclasts, dendritic cells, microglial cells, T-cells, B-cells, megakaryocytes, germ cells, nurse cells, neural cells, stem cells, etc.) or biological material of possible interest. The system 100 is preferably defined on a substrate 110, more preferably a microfluidic chip, but can alternatively be located on or defined by any suitable substrate.

In specific examples, the system 100 can be used with method(s) operable for single cell polymerase chain reaction (PCR), wherein such systems can facilitate high efficiency capture of cells (e.g., 100s, of cells, 1000s of cells, 10,000s of cells, 100,000s of cells, 1,000,000 of cells, etc.) in single cell format (or single cluster format) within wells, as well as on-chip reagent delivery to the wells, incubation, and thermocycling in order to provide a cell capture-to-PCR workflow. In more detail, microfluidic and other portions of the system can be operable to perform assays (e.g., assays associated with ARV7 mRNA) using PCR with sample (e.g., prostate clinical samples) with single cell or single cell cluster resolution. In specific examples, the system 100 can accommodate sample volumes as low as 10 μl to as high as on the order of up to 1 mL within a fluid reservoir 160 associated with the array of wells 120, wherein the sample can contain a range of between 500 to 100,000 target cells, thereby providing the ability to process larger sample volumes containing a large number of cells of interest.

Figure 2A:
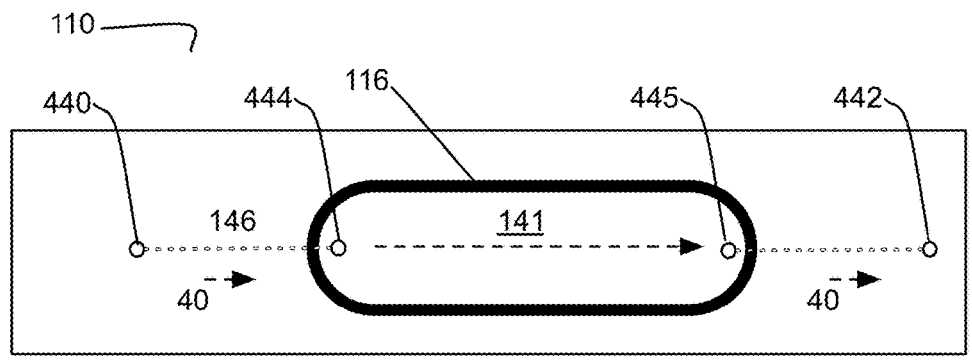
FIGS. 2A-2C depict variations of a portion of a system for isolating and analyzing cells.
Figure 2B:
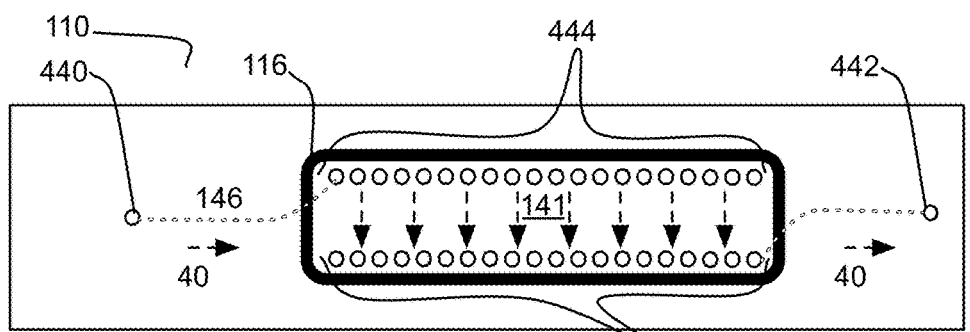
Figure 2C:
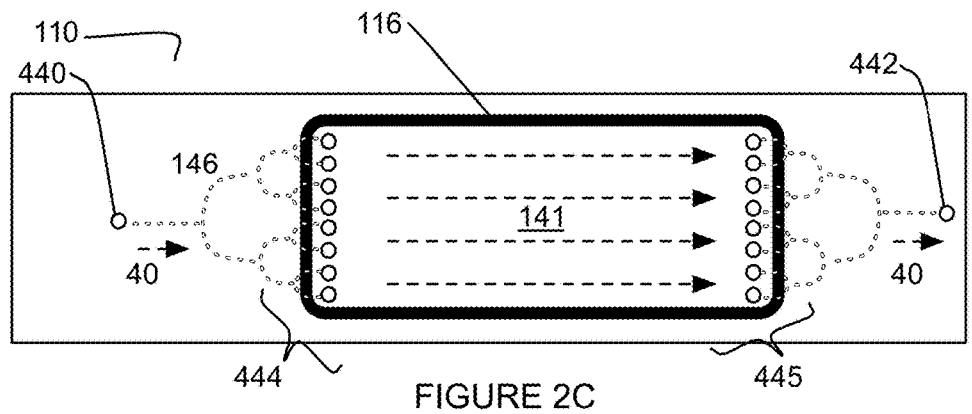

The system 100 preferably achieves individual cell capture and retention from a biological sample including a cell population 20 without antibody coated wells, and preferably maintains the viability of the cells throughout isolation, capture, retention, and/or removal. Individual cell capture is preferably achieved by flowing or dispensing a sample containing a group of single cells within a fluid layer over the array of wells 120 in a direction parallel (e.g., substantially parallel, within 0.1 degrees of parallel, within 1 degree of parallel, within 45 degrees of parallel, completely parallel, etc.) to the broad surface of the substrate, and capturing the cells once they have descended through the fluid layer towards the array of wells 120 under the influence of gravity. Alternatively, individual cell capture can be achieved by delivering a sample containing a group of single cells into a fluid layer provided by a fluid reservoir 160, over the array of wells 120 in a direction perpendicular to the broad surface of the substrate, and capturing the cells once they have descended through the fluid layer towards the array of wells 120 under the influence of gravity. However, in some variations, individual cell capture can additionally or alternatively be achieved by any suitable mechanism for promoting single cell transfer into a well of the set of wells. Furthermore, the system 100 is preferably configured to prevent undesired fluid currents that can lift cells from the substrate or move cells/cell clusters from well cavities 128 at which the cells are captured and fully retained within. However, in some variations, the system 100 can be configured to facilitate moving of cells/cell clusters in any suitable manner. The flow path of a fluid (e.g., biological sample, process reagent 40) through the system 100 is preferably multi-directional and uniform, such that each cell/cell cluster in the system 100 experiences consistent conditions (e.g., gradient length scales along the flow path of flow properties such as pressure, density, temperature, solution composition, and other suitable properties are large relative to the length scales of the system); however, the flow path can alternatively be unidirectional, bi-directional, or have any other suitable characteristic(s). In variations of a specific example, as shown in FIG. 2A-2C, the flow path 141 of a fluid through the system includes a set of fluid pathways 146 (e.g., of a manifold coupled to the array of wells) of equal length (e.g., substantially equal length, equal length to within manufacturability tolerances, etc.) that are configured such that a reagent supplied at a manifold inlet 440 to the set of fluid pathways 146 arrives at each array of inlets 444 (e.g., a single well, along a region of a first edge of the reservoir, along region of a first edge of the active region of the substrate, etc.) at substantially the same time point (e.g., at the same time, within 1 second, within 1 minute, etc.), and passing across the active region 116 of the substrate (e.g., containing the array of wells 120) through an array of outlets 445 to a manifold outlet 442. Cell transport, isolation, sorting and viability maintenance can additionally be accomplished by controlling the sample flow rate through the system (e.g., by adjusting the flow rate so that a characteristic length scale of the flow is of a similar order as a characteristic length scale of a well, by dithering the flow rate between high and low flow conditions, etc.), or through any other suitable means. However, the flow characteristics of a fluid through system 100 may be otherwise configured.

In operation, the system 100 preferably receives a biological sample including the cell population 20 and facilitates distribution of the biological sample uniformly across the array of wells 120 (e.g., using uniform cross flow, smearing, a cytospin procedure, pipetting aliquots of the sample at different regions of the array etc.). However, the system 100 can additionally or alternatively facilitate distribution of the fluid 40 (e.g., biological sample, process reagent, non-cell particles) across the set of wells using positive pressure (e.g., positive pressure at an inlet to the array) and/or negative pressure (e.g., negative pressure at an outlet of the array) applied by the flow control subsystem 180. Additionally or alternatively, actuation pressure that facilitates sample distribution can be cycled in a pulse-width modulation fashion or sinusoidal fashion to provide net actuation pressure, either net positive at the inlet or net negative at the outlet. As such, desired cells having a defining characteristic (e.g., size-based characteristic, density-based characteristic, adhesion-based characteristic, etc.) can be trapped within a well 128 as the biological sample flows across the array of wells 120. For example, in the variation of the system 100 configured to capture CTCs, the wells are preferably configured based upon defining morphological features of CTC cells, in order to facilitate capture and retention of CTCs in single cell or single cluster format. However, the system 100 can additionally or alternatively be configured to retain and facilitate processing or any other suitable particle of interest in any other suitable format. Actuation pressure is preferably provided by the flow control subsystem 180 (e.g., a manually-operated pipette, automated fluid-handling robot, vacuum pressure system, electromechanical micropump, etc.) in fluid communication with the system 100, but can alternatively or additionally be provided by any suitable mechanism.

Figure 35:
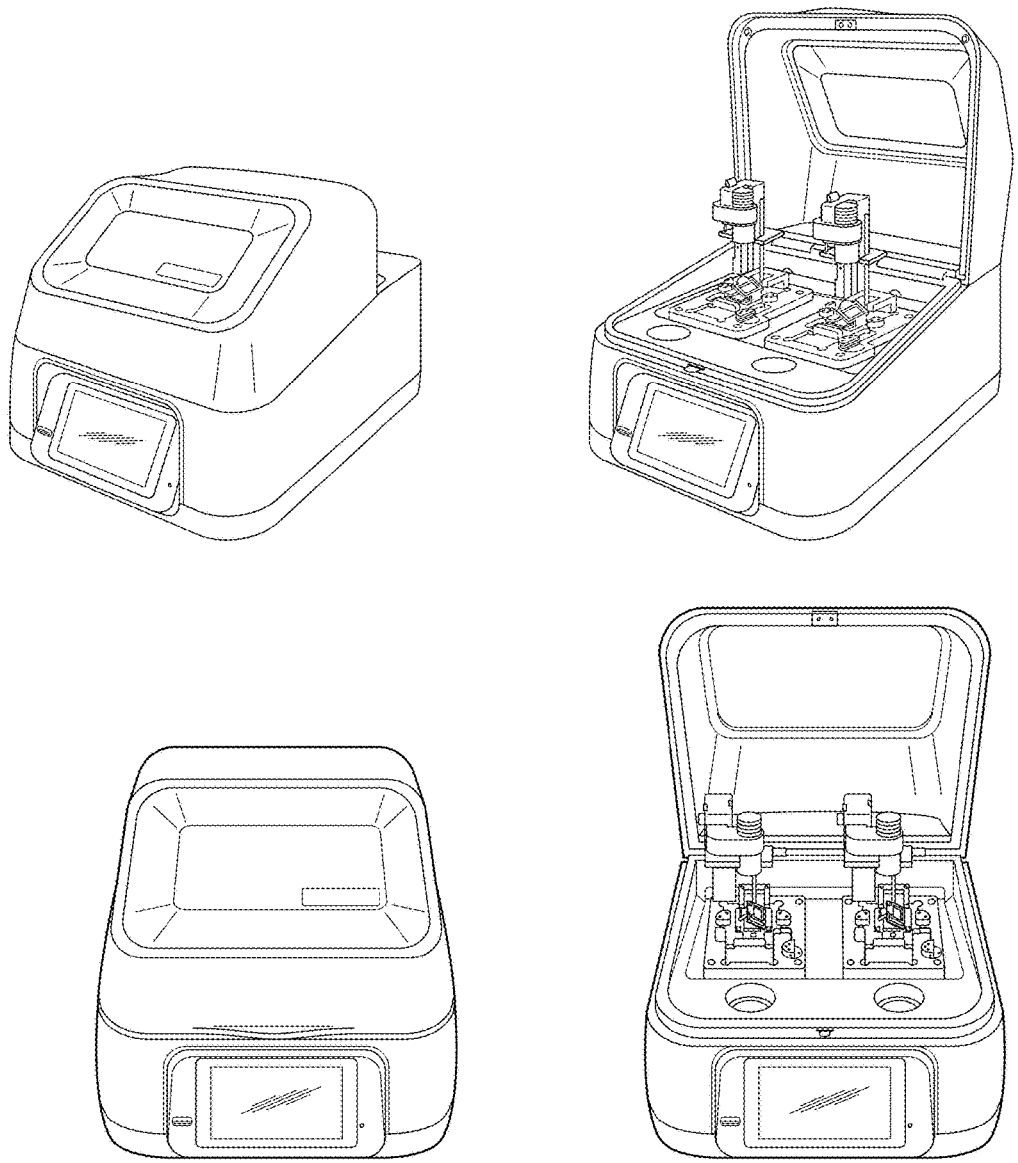
FIG. 35 depicts an embodiment of a system for isolating and analyzing cells.

In a preferred embodiment of the system 100, shown in FIG. 35, up to two individual arrays of wells can be processed in parallel (synchronously, asynchronously).

However, the components of the system can be configured with any numerosity to accommodate any suitable number of arrays.

1.1 System—Substrate

As shown in FIG. 3, the substrate 110 functions to provide a medium at which the array of wells 120 (set of microwells, microwells, wells) can be defined. In variations, the substrate 110 can have a first side (e.g., upper broad surface) 112, and a second side (e.g., lower broad surface) directly opposing the first side. The upper broad surface 112 of the substrate 110 is preferably a planar surface, such that microfluidic elements (e.g., inlet, outlet, inlet manifold, outlet manifold, fluid channels, etc.) of the system 100 are defined at least partially at a planar surface. Alternatively, the upper broad surface 112 of the substrate 110 can be a non-planar surface, such that microfluidic elements of the system 100 are defined at least partially at a non-planar surface. In variations, the non-planar surface can be a concave surface, a convex surface, or a surface having concave, planar, and/or convex surfaces. Such variations can facilitate various methods of depositing and distributing a sample at the array of wells 120. In any variations of the substrate 110 including a non-planar upper broad surface 112, the non-planar portion(s) are preferably shallow (e.g., having a small depth relative to a width of the broad surface) or short (e.g., having a small height relative to a width of the broad surface); however, the non-planar portion(s) can additionally or alternatively include portions that are deep (e.g., having a large depth relative to a width of the broad surface) or tall (e.g., having a large height relative to a width of the broad surface). However, the surface can alternatively have any other suitable axis or type of symmetry, or can be asymmetrical. In a preferred application, the first side of the substrate can define an alignment axis for a surface plane 118, wherein the surface plane 118 is parallel and coaxial to the first side of the substrate, and aligned between the first side of the substrate, and the base of a fluid reservoir through which fluids, such as a sample or process reagent, may flow to access the array of wells at the substrate.

The substrate 110 composition can provide desired characteristics relating to any one or more of: mechanical characteristics (e.g., substrate mechanical properties as a mechanical stimulus), optical properties (e.g., transparency), electrical properties (e.g., conductivity), thermal properties (e.g., conductivity, specific heat, etc.), physical characteristics (e.g., wettability, porosity, etc.), and any other suitable characteristic. The substrate 110 is preferably composed of a rigid material with high transparency (e.g., a transparent material, a translucent material), in order to facilitate imaging of the substrate no to analyze captured single cells/cell clusters. The high transparency material is preferably optically transparent, but can additionally or alternatively be transparent and/or translucent to other portions of the electromagnetic spectrum (e.g., microwaves, near infra-red, ultraviolet, etc.) In a few such variations, the substrate 110 can be composed of any one or more of: glass, ceramic, a silicone-based material (e.g., polydimethylsiloxane (PDMS)), a polymer (e.g., agarose, polyacrylamide, polystyrene, polycarbonate, poly-methyl methacrylate (PMMA), polyethylene glycol, etc.), paper, a porous material, and any other suitable material, including composites thereof, with high transparency. Alternatively, the substrate 110 can be composed of any other suitable material having any other suitable optical properties. Additionally or alternatively, the substrate can be composed of any one or more of: a ceramic material, a semi-conducting material, a polymer, and any other suitable material.

The substrate no can be processed using any one or more of: etching methods, molding methods, printing methods (e.g., 3D printing processes), machining methods, and any other suitable manufacturing processes suited to a brittle, elastic, or ductile substrate material. Furthermore, features defined at the upper broad surface 112, including the array of wells, can be produced by any one or more of: molding, by polishing, by spinning a material in a flow phase followed by setting the material, by machining, by printing (e.g., 3D printing), by etching, and by any other suitable process. In a specific example, the array of wells 120 is defined within a silicon mold using a three mask photolithographic process and deep reactive ion etching (DRIE) process to etch microfluidic elements into the silicon mold. In the specific example, the etched elements of the silicon mold are then transferred polymethylmethacrylate (PMMA) sheets as a substrate 110 using a hot embossing process. The substrate 110 in the specific example has dimensions of 3 inches by 1 inch, in order to substantially match dimensions of a glass microscope slide. In variations of the specific example, and/or for other variations of the array of wells 120, hot embossing of cyclic olefin polymer (COP) can be substituted for PMMA to form the microfluidic structures of the array of wells 120. However, the substrate 110 can alternatively be any other suitable substrate 120 processed in any other suitable manner.

Preferably, the substrate includes features that permit interaction (e.g., reversible or non-reversible attachment, coupling) to other subcomponents of system 100. In one variation, the substrate 110 can be coupled to components the fluid delivery module 140, wherein the substrate includes an inlet 142 and an outlet 144 to transmit fluid 40 into and out of the active region 116 of the substrate. In an example of this variation, the set of inlet channels of the inlet manifold and the set of outlet channels of the outlet manifold 164 can be embedded directly within the substrate between the upper and lower broad surfaces, but can additionally or alternatively be fabricated into at least a portion of the upper broad surface of the substrate. In another example, as shown in FIGS. 28A-28C, FIG. 29, and FIGS. 30A and 30B, the substrate 110 can be aligned to a first plate 150 containing a recess 152 superior to the active region of the substrate, wherein, upon attachment of the first plate 150 to the substrate, a region of the first plate 150 can be aligned above the array of wells to cooperatively define a fluid reservoir 160 to transfer fluid across the array of wells during operation of system 100. The fluid reservoir 160 can be sealed by a reservoir lid 164 that can be reversibly attached to the first plate 150, such that the combined assembly provides a fluid pathway 162 for delivery of reagents, air, oil or other materials to flow parallel to the surface of the array of wells. The resealable reservoir lid 164 can include a set of grooves 165 at the base of the reservoir lid, at the region of the reservoir lid that is inserted into the fluid reservoir, for ease of displacement of immiscible liquid (water replacing oil, oil replacing water) and, additionally or alternatively, displacement of different fluidic phases (water replacing air or air displacing water) along the fluid pathway 162. The grooves 165 of the reservoir lid 164 can posses characteristic dimensions on the order of: 25 microns, 50 microns, 100 microns, 150 microns, 200 microns, 250 microns, 300 microns, 350 microns, 400 microns, 500 microns and/or 1 millimeter. The number of grooves and dimensions of grooves 165 can be adjusted to allow for specific dead-volume of liquid to be provided in the systems, such as approximately: 10 microliters, 25 microliters, 50 microliters, 75 microliters, 100 microliters, 150 microliters, and/or 200 microliters. The material of the lid may be optically transparent to allow imaging of the cells or beads captured in the microwell arrays and/or UV-irradiation for photocleaving of specific biomolecules from surfaces of the microwells, particles, and/or genetic complexes, as described in Section 2. The reservoir lid 164 also accommodates elastomeric surfaces (FIG. 33) to allow for proper seal with the fluidic manifold. The resealable lid may be opened or closed at the beginning of the fluidic operation, in the middle of the process or at the end of the process as needed to deliver cells to the array of wells, deliver particles to the array of wells, deliver reagents to the array of wells, and/or remove specific cells, particles, and/or fluids from the array of wells. The reservoir lid 164 is designed for easy attachment or removal, either manually or in an automated fashion, however can be configured for operation in any other suitable manner to provide a complete fluidic system.

In a second variation, the substrate 110 can be attached to a substrate platform 105 that functions to reversibly attach and align the substrate to a platform, heating element (e.g., thermal control module 194), and/or stage upon which assays are performed, wherein the stage can be used to physically adjust the position of the substrate within the system 100 to improve access of the array of wells to other elements of the system, such as the imaging subsystem 194, thermal control module 190, and/or the extraction module. Preferably, the substrate platform 105 can be configured to accommodate, secure, and manipulate substrates with various array configurations (e.g., arrays with 50,000 wells, arrays with 1M wells, etc.) with high precision, and can include an optional substrate attachment mechanism 110. As shown in examples depicted in FIGS. 30A-30B, FIGS. 31A-31C, FIGS. 32A-32C, and FIG. 33, the substrate platform can include a platform lid 115 that can accommodate and support the reservoir lid 164, wherein the platform lid 115 functions to reversibly secure and seal the reservoir lid 164 into the fluid reservoir 160 formed by the first plate 150 attached to the substrate. In variations, the platform lid 115 can include an elastomeric gasket or sealing element and a detent plunger that applies pressure in a range between 1-4 pounds, in order to hermetically seal the fluid reservoir. In a specific application, the platform lid 115 can permit the array of wells to be observed (e.g., via the imaging subsystem 194, via the naked eye) with the reservoir lid 164 in either an open or a closed position above the array of wells. Furthermore, the base surface of the substrate platform can include an optically transparent and/or high-conductivity material that functions as a region of access to the array of wells 120 secured at the substrate platform to enable optical interrogation and/or thermal modulation of the substrate 110. In a preferred application, the substrate platform 105 can be used to precisely and reproducibly place the substrate on a heating element (e.g., a thermocycler surface) of the thermal control module 190, in order to better ensure reliable and uniform exposure of the array of wells to the heating/cooling source. However, the substrate can be configured in any other suitable manner to engage with any other suitable component of the system.

1.2 System—Array of Wells

The array of wells (set of microwells, microwells, wells) 120 functions to capture the set of cells in addressable, known locations such that the set of cells can be individually identified, processed, and analyzed. As such, the array of wells 120 is preferably configured to facilitate cell capture in at least one of a single-cell format and single-cluster (e.g., a cell-particle pair) format. However, the array of wells 120 can additionally or alternatively be configured to receive any other suitable type of particle, in any other suitable format. For instance, the array of wells 120 can be configured (e.g., sized, shaped) to receive mammalian cells, embyros, microspheres, particles, cell-particle pairs, and cells conjugated to microspheres.

Figure 3A:
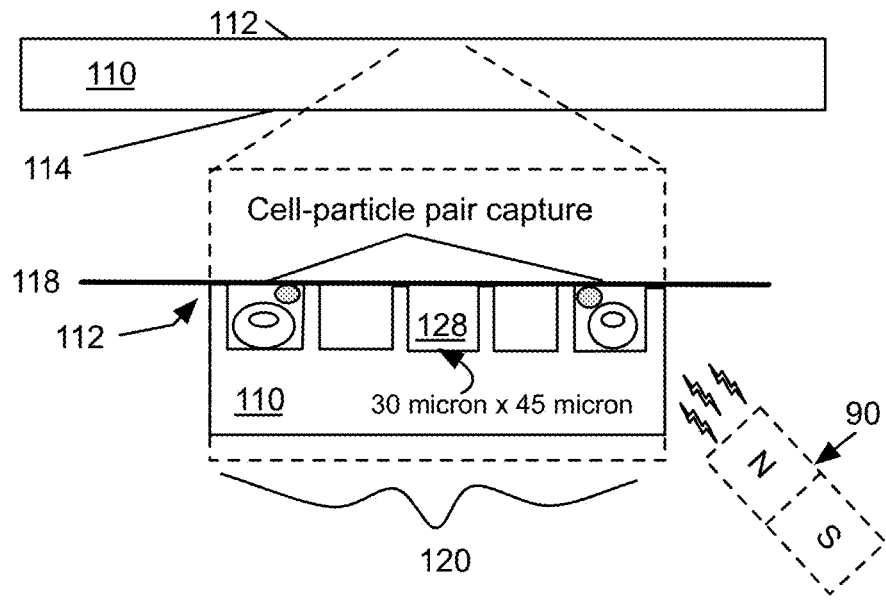
FIGS. 3A-3B depict variations of a portion of a system for isolating and analyzing cells.
Figure 3B:
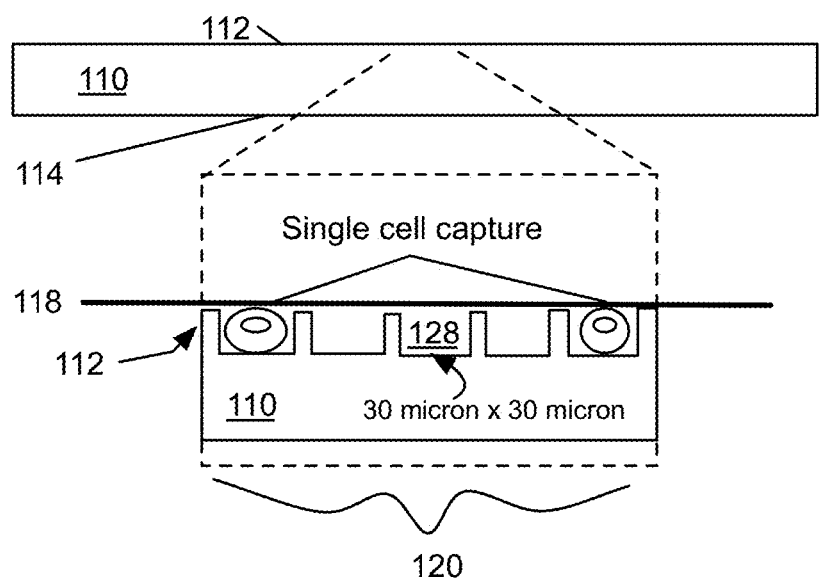

As shown in FIG. 1 and FIGS. 3A-3B, the array of wells 120 is preferably defined at the upper broad surface 112 of the substrate 110, each well 128 in the array of wells 120 including a base surface 124 defined within the substrate and proximal a second side (e.g., lower broad surface 114), an open surface 122 directly opposing the base surface 124 and proximal the upper broad surface, and a set of walls 126 extending between the base surface and the open surface defining the well cavity 128 of the well.

The array of wells 120 is defined at an active region 116 of the substrate 110, wherein the active region can be any suitable area (e.g., 1 square inch, 10 cm, 2 square inch, 3 square inch, 4 square inch, etc.) of the substrate (FIG. 2A-2C). Preferably, the active region (and the array of wells) of the substrate is accessible by other components of the system 100, including the imaging subsystem 194, fluid delivery module 140, thermal control module 190, and/or extraction module, in order to perform isolation, processing, and analysis of single captured cells. The array of wells 120 can include any suitable number of wells (e.g., on the scale of 100, 1,000, 10,000 wells, 50,000 wells, 100,000 wells, 1 million wells, 2 million wells, 3 million wells, 4 million wells, 5 million wells, 6 million wells, 7 million wells, 9 million wells, 10 million wells, etc.). In preferred variations, the array of wells includes at least 250,000 wells. In a specific example, the array of wells includes approximately 1 million wells (FIGS. 28A-28C and FIG. 29). However, the array of wells can be configured in any other suitable manner.

The open surface 122 is preferably an opening in the substrate 110 that provides access to the base surface 124 of a well 128, and is configured to receive one of a single cell, a single particle, and a single cluster of cells or particles (e.g. a cell-particle pair), from a direction perpendicular to the upper broad surface 112 of the substrate 110. For variations in which the system is configured to retain a cell-particle pair, as shown in FIG. 3A, each of the cell and particle of the cell-particle pair can be received in sequence or simultaneously. As such, the open surface 122 can have a characteristic dimension (e.g., width, diameter, circumference, etc.) that is larger than, smaller than, or equal to that of the base surface 124. In an example for capture of circulating tumor cells (CTCs) and a particle in single cell-particle pair format, the characteristic dimension of either the base surface 124 or the open surface 122 can range between 20 to 40 micrometers, and the height of the well cavity can range between 20 to 75 micrometers. In another variation, wherein the system is configured to retain either a single cell or a single particle, as shown in FIG. 3B, the characteristic dimension of the base surface and/or the open surface can range between 20 to 40 micrometers, and the height of the well cavity can range between 10 to 40 micrometers. However, in other variations, any dimension of the wells within the array of wells, including well cavity height and well cavity width, can be any value between 0.5 microns to 50 microns, and can optionally be selected based on the assay to be performed by the system 100, the dimensions of the target cells, and/or the dimensions of the particles used. The open area of the array of wells 120 (i.e., the sum total area of the open surface of each well in the set of wells) is preferably greater than 50% of the total area of the region of the substrate at which the wells are defined; more preferably, the open area is greater than 80% of the total area. However the open area can be any suitable fractional area or percentage of the total area of the substrate.

The open surfaces of each well are preferably aligned flush with the upper surface of the substrate (e.g., at a surface plane 118), but can alternatively be slightly recessed within the substrate or otherwise configured. Preferably, as shown in FIGS. 3A and 3B, the open surfaces of the wells of the array of wells are aligned with a surface plane 118 of the substrate, wherein the horizontal axes of the open surfaces are coaxial with the surface plane 118. In an example, the surface plane 118 can be a plane with a lateral face parallel to the upper broad surface of the substrate, and defined at the intersection of the upper broad surface of the substrate and a region of space superior the upper broad surface of the substrate. In a specific example, the surface plane 118 is a spatial boundary arranged between the upper broad surface of the substrate and a lower region of a fluid reservoir located superior the array of wells, and defined at the interface between the open surfaces of the array of wells and a fluid path within the fluid reservoir. In a preferred application, cells and/or particles that are received into a well below the surface plane 118 are not accessible by fluid flow at the open surface of the well, and are thus considered fully retained by the well cavity 128 of the well, while cells and/or particles traversing the surface plane 118 or remain above the surface plane 118 are accessible by fluid flow and are transmitted downstream of the fluid path, and are thus considered partially and/or non-retained by the well cavity 128. However, the surface plane 118 can additionally and or alternatively be arranged with respect to any dimension of the substrate and/or the array of wells. Furthermore, the open surfaces of each well can be positioned with respect to any region of the substrate, fluid reservoir, and/or fluid path.

Figure 4A:
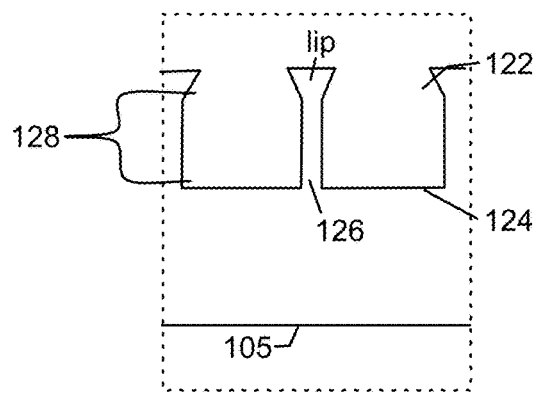
FIG. 4A depicts a variation of a portion of a system for isolating and analyzing cells.
Figure 4B:
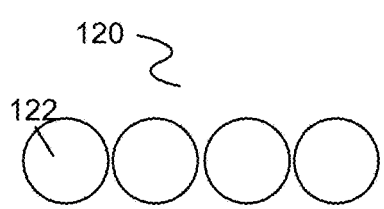
FIGS. 4B-4E depict schematic representations of example configurations of a portion of a system for isolating and analyzing cells.
Figure 4C:
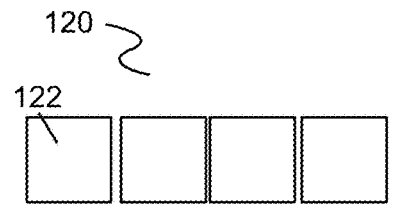
Figure 4D:
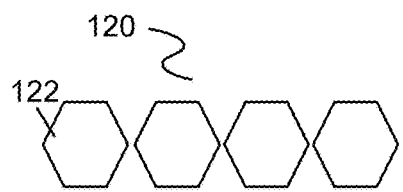
Figure 4E:
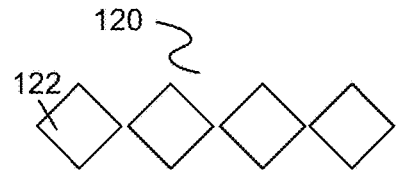

In preferred variations, the open surfaces of each well are directly fluidly coupled to a fluid path directly above and laterally superior to the array of wells. To enhance fluid flow across the open surfaces of the array of wells, the open surfaces of each well can optionally include a coating (e.g., hydrophobic, hydrophilic, electrostatic material, chemoattractive, etc.) or physical features (e.g., texturized, notched, ridged, etc.). Furthermore, the open surfaces of each well can optionally include passive or active retention features to retain and hold a single cell, or single cell-particle pair (e.g., physically or chemically triggered to increase or decrease open surface of well when well cavity 128 is occupied). In one example wherein the open surface 122 has a characteristic dimension smaller than that of the base surface 124, as shown in FIG. 4A, a well 128 can have a lip that forms a boundary of the open surface 122 in order to provide a characteristic dimension that is smaller than that of the base surface 124. The lip can be planar or non-planar, and can further facilitate retention of a single cell or a single cluster of cells at the well 128. FIGS. 4B to 4E depict variations of the open surfaces of each well, which can define any geometry for receiving a cell and/or particle into the well cavity, including a circular opening, rectangular opening, hexagonal opening, or any other suitable shape. The open surface 122 can, however, include any other suitable feature that facilitates fluid flow, cell reception, and/or particle retrieval from the well 128 of the array of wells 120.

The base surface 124 is preferably parallel to, symmetrical to, and directly opposing the open surface 122; however, in some variations, the base surface 124 can alternatively be non-parallel to, non-symmetrical to, and/or offset from the open surface 122. Similar to the upper broad surface 112 of the substrate 110, the base surface 124 can be a planar surface or a non-planar surface, and in variations of the base surface 124 having a non-planar surface, the non-planar surface can include convex and/or concave portions having any suitable geometric characteristic, as shown in FIG. 5A. Additionally or alternatively, as shown in FIGS. 5B and 5C, the base surface 124 can be any one or more of: textured (e.g., to facilitate desired fluid flow behavior, to attract or repel a given particle type, etc.), characterized by a desired porosity, characterized by a desired surface treatment, characterized by immobilized particles or biochemical moieties, and characterized by any other suitable feature that facilitates cell reception and/or retention in any other suitable manner. Though in preferred variations, the base surface is closed such that there is no fluid flow through from the open surface of the chamber through the bottom surface of the chamber, the base surface can be alternatively configured to include one or more fluid channels to allow egress of particles with characteristic dimensions less than the target cell in order to exit the well cavity 128. However, the base surface can be otherwise configured in any other suitable manner.

Figure 6A:
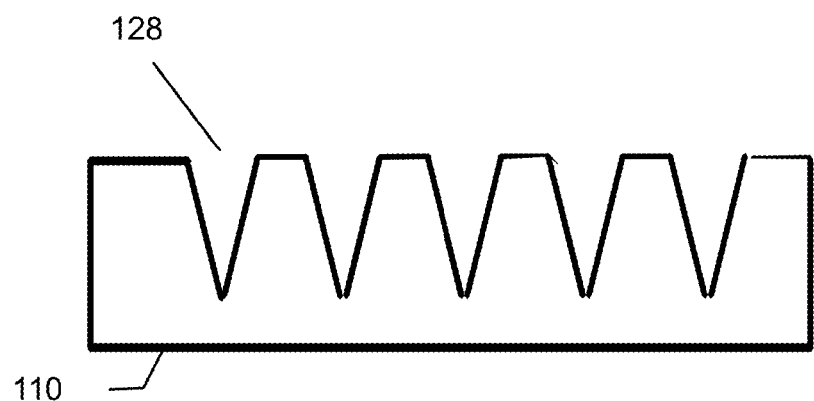
FIGS. 6A-6B depict variations of a portion of a system for isolating and analyzing cells.
Figure 6B:
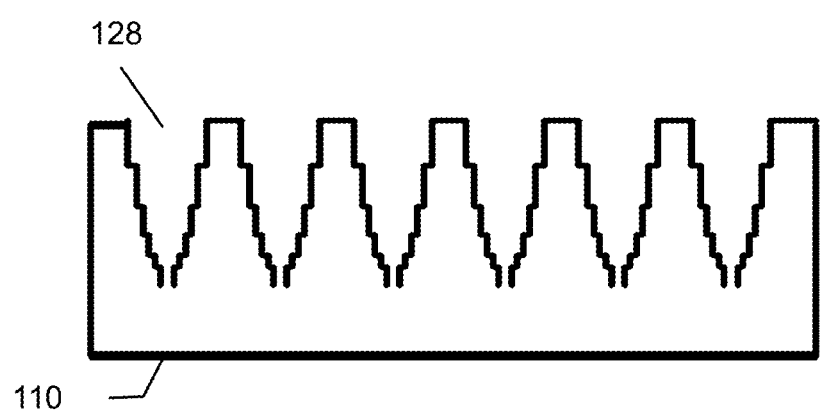

In relation to the base surface 124 and the open surface 122, each well 128 preferably has at least one wall (e.g., a set of walls) 126 extending between the base surface 124 and the open surface 122. In a variation, as shown in at least FIG. 1 and FIG. 4A, the walls of each well 126 at least partially physically and fluidly separates an individual well 128 from at least one other adjacent well, defines a depth, width, and/or cross-sectional dimensions of the well, and are preferably perpendicular to a plane defined by the horizontal axis of the open surface 122. Preferably, the wall thickness of the walls 126 is between 4-5 micrometers, but can be any dimension less than 10 micrometers. The wall 126 can extend vertically from a plane defined by the open surface 122 to the base surface 124 to define the well cavity 128; as such, in some variations, a well cavity 128 of each well in the the array of wells can be prismatic (e.g., cylindrical prismatic, hexagonal prismatic, polygonal prismatic, non-polygonal prismatic, etc.). In a specific example, the well cavity of each well defines a hexagonal prism. However, as shown in the variations depicted in FIGS. 6A and 6B, the wall 126 can extend between the open surface 122 and the base surface 124 in any other suitable manner in other variations (e.g., curved walls, straight walls, bent walls, etc.). For instance, the wall 126 can gradually reduce a characteristic dimension (e.g., diameter, horizontal cross section, vertical cross section) of the well from the open surface to the base surface (e.g., by forming discrete steps, by gradually adjusting the characteristic dimension in a linear or a non-linear manner with any suitable slope, etc.). However, in some variations, a well 128 may not have a well-defined wall 126 perpendicular to a plane defined by the open surface 122 (e.g., the base surface may extend in some manner directly to the open surface without forming a wall perpendicular to the open surface). In examples, the base surface 124 and the open surface 122 can be separated, with or without a wall, by a distance (e.g., height of a well cavity 128) of between 0.5 microns to 50 microns (e.g., approximately 25 microns for an application involving capture of single CTCs, approximately 40 microns for an application involving capture of single cell-particle pairs). However, the wells of the array of wells can be configured with any other physical characteristic and/or dimension, in order to perform the isolation, processing, and analysis steps described in method 200. In a preferred application, method 200 can include selecting an array of wells with specific dimensions, numerosity, geometry, spatial arrangement and/ or any other suitable characteristic, according to the dimensions of target cells desired to be captured, dimensions of non-cell particles utilized, and other parameters required to perform a specific assay using system 100 (as described in Block S218). Additionally or alternatively, the set of walls can include a set of channels that fluidly couple each well to at least one adjacent well in the array of wells 120. In such variations, the channel(s) of a set of channels can be defined within a region of the substrate no between adjacent wells, or can be defined by overlapping portions of adjacent wells. In a specific example, a channel can have a characteristic dimension of 5 microns, and in variations of the specific example, a channel can have a characteristic dimension ranging from 0.5 microns to 75 microns.

The walls of the array of wells are preferably constructed from the same material as that of the substrate (as described in a previous section), but can alternatively be constructed of any other suitable material to confer desired physical or chemical properties to the well cavities of the array of wells. For example, the walls can be configured to be non-permeable or semipermeable to various particles or fluids in solution that has entered the well cavities, and additionally or alternatively configured to be permanently or non-permanently rigid, flexible, or shape-changing (e.g., ability to expand open or collapse closed) to control cell and/or particle entry into the well. In an embodiment of method 200, wherein the system 100 is used to capture single cell-particle pairs, wherein the cells are captured in a first step and the particles are captured in a second step following the first step, at least a portion of the walls of the each well in the array of wells can be made of a shape-memory polymer, operable between a first open state and a second closed state. In an example, if a target cell is captured within a well at the first step, the walls of the well cavity 128 can maintain the first open state to permit the capture of a particle into the well at the second step, but if a target cell is not captured within a well at the first step, the walls of the well cavity 128 can be activated to transition into the second closed state, essentially closing the open surface of each unoccupied well, which can increase the efficiency of generating cell-particle pairs within the wells, and can help identify the wells of the array occupied by desired target cells. However, the physical and chemical properties of the wells can be configured in any other suitable manner to enhance the performance of the system for any suitable application and/or variation of method 200 described in Section 2.

Figure 7:
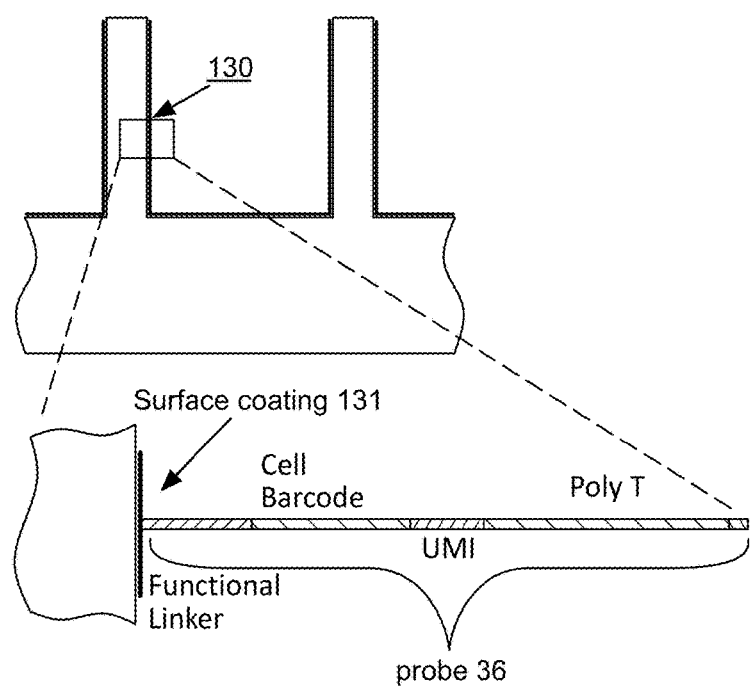
FIG. 7 depicts an example of a variation of a portion of a system for isolating and analyzing cells.

The internal surfaces of the well cavity 128 of each well in the array of wells (e.g., the sidewalls of the walls facing the interior of the well cavity 128) can optionally be configured to interact with the contents retained within the well cavity 128 (e.g., a captured cell, biological material, non-biological material, non-cell particles, cell-particle pairs, etc.). To permit such interaction, the internal surfaces can include a functional feature (physical or chemical) or surface-bound moiety on all sidewalls of the well cavity 128, but can alternatively be localized to any suitable portion or specific region of the well cavity 128 (e.g., at the base surface, proximal the open surface, along the sidewalls, etc.). In a first variation, as shown in FIG. 7, the internal surfaces include a functional surface coating 131 configured to bind to nucleic acid content that has been released from a lysed captured cell, a probe or set of probes 36 released from a non-cell particle, and/or any other suitable captured entity within the well. The functional surface coating 131 can be of synthetic, animal derived, human derived, or plant derived proteins that can bind to a functional linker of a nucleic acid probe 36, as further described in Section 2. In an example, the functional surface coating permits biotinylated surface chemistry (e.g., biotin-streptavidin linkers) to bind to a probe including a functional linker. However, the functional surface coating of the internal surface of a well can be configured to bind to any contents retained within the well cavity 128 in any other suitable manner. In a second variation, the functional surface coatings are configured to physically retain and/or manipulate the captured content, such as orienting a captured target cell or particle in a particular direction for downstream analysis (e.g., optical imaging). In an example, the functional surface coatings include a polymer or protein providing a sticky layer to adhere to a region of the captured target cell (e.g., polymer adhesive, catechol-polystyrene, poly-D-lysine, fibronectin, collagen, vitronectin, etc.). In another example, the functional surface coating includes a polymer or protein that attracts a cell towards the open surface of the well, or is a semi-permanent barrier at the open surface of the well to control entrance of particles into the well. In a third variation, the internal surfaces of the well are configured to add a chemical agent (e.g., a drug interacting with the cell, an agent that controls pH of the solution within the well, an agent that controls density of fluid within the well, etc.), biochemical agent (e.g., a fluorescent marker, antibodies, etc.), and/or a process reagent (e.g., a lysis buffer contained in a timed-released delivery vehicle/microsphere, etc.), in order to perform downstream assays and analysis of the captured cells. In a fourth variation, the the internal surfaces of the well can include physical features to increase, decrease, or vary the surface area (e.g., ridges, protrusions, pores, indentations within the well cavity 128). Furthermore, the physical features can include functionalized microparticles that have been immobilized within the well, reflective components to enhance optical access and optical interrogation of contents retained within the well, and/or magnetic elements to manipulate the position of the cell or particle within the well.

While every well 128 in the array of wells 120 can be substantially identical, the array of wells 120 can alternatively include wells that are non-identical to each other by any suitable feature (e.g., morphological feature, mechanical feature, surface coating feature, thermal conductivity feature, electrical conductivity feature, etc.). As such, some variations of the system 100 can be configured to capture at least one of multiple particle types and particles in multiple types of formats, in addressable locations, for processing and analysis. In a first example, the array of wells 120 can include a first subset of wells with wells having a first characteristic dimension (e.g., well diameter, well depth, well volume, etc.) in order to capture a first cell type in single cell format, and a second subset with wells having a second characteristic dimension (e.g., well diameter) in order to capture a second cell type in single cell format. In the first example, the first subset can be centrally located within the array of wells 120, and the second subset can be peripherally located within the array of wells 120 and have a second characteristic dimension that is smaller than the first characteristic dimension, in order to facilitate capture of larger particles at a central portion of the array of wells 120 and smaller particles at a peripheral portion of the array 100 (e.g., in a cytospin application). In one variation of the first example, the array of wells 120 can include wells having a gradient of characteristic dimensions in a radial direction (e.g., larger well dimensions toward the center of the array and smaller well dimensions toward the periphery of the array). In other variations of the first example, the array of wells 120 can include wells having a gradient of any other suitable feature characteristic (e.g., morphological feature, mechanical feature, surface coating feature, thermal conductivity feature, electrical conductivity feature, etc.) in a radial direction. In other examples, the array of wells 120 can include wells having a distribution (e.g., gradient) of any suitable feature characteristic (e.g., morphological feature, mechanical feature, surface coating feature, thermal conductivity feature, electrical conductivity feature, etc.) along any suitable direction (e.g., linear direction, radial direction, circumferential direction, etc.).

In variations including subsets of wells, the subsets can be separated from one another. In a first variation, each subset can be separated from other subsets by a portion of the substrate in which no wells are defined (e.g., a flat region of the broad surface). In a second variation, the subsets can be fluidically-isolated regions of a contiguous arrangement of wells, in which none of the wells of a particular subset are fluidly coupled to a well of another subset. In a specific example, the substrate defines twelve distinct subsets of the array of wells 120, arranged in a two-by-six grid, that are separated from adjacent subsets by flat region of the broad surface, with a uniform spacing (e.g., 1 mm, 100 microns, 3 mm, etc.) between array edges. The subsets of wells can be further divided into groups (e.g., groups of seven wells within a subset of 20,000 wells of a 250,000 well set of wells), and any suitable interconnectivity between wells (e.g., among subsets, between groups, etc.) can be provided by the set of channels of each well. Such configurations may permit efficient cell capture (e.g., by a group including seven interconnected wells) by groups of wells, while allowing the set of wells to be exposed to multiple distinct samples (e.g., one sample per subset of the set of wells). In an example, wells can be approximately 30 microns in diameter, 30 microns deep, and wall thicknesses of 4-5 microns (e.g., which provides more efficient cell capture). However, in related variations, the array of wells 120 can alternatively be subdivided and/or interconnected in any suitable manner. The subsets and/or groups of wells can be arranged in any suitable manner. For example, the subsets can be arranged in a rectilinear fashion (e.g, a grid layout of well subsets) and the groups can be arranged in a packed configuration (e.g., hexagonal close-packed, square lattice, etc.), and vice versa; the arrangement of the groups and subsets are preferably independent of one another, but can alternatively be based on one another (e.g., the subsets are arranged in a rectilinear fashion because the groups are arranged in a rectilinear fashion). Furthermore, each substrate 110 of the system 100 can have a single array of wells 120, or can have multiple subsets of wells defined at the substrate in any suitable manner (e.g., in a radial configuration, in a rectangular configuration, in a linear configuration, in a curvilinear configuration, in a random configuration, etc.).

Figure 8A:
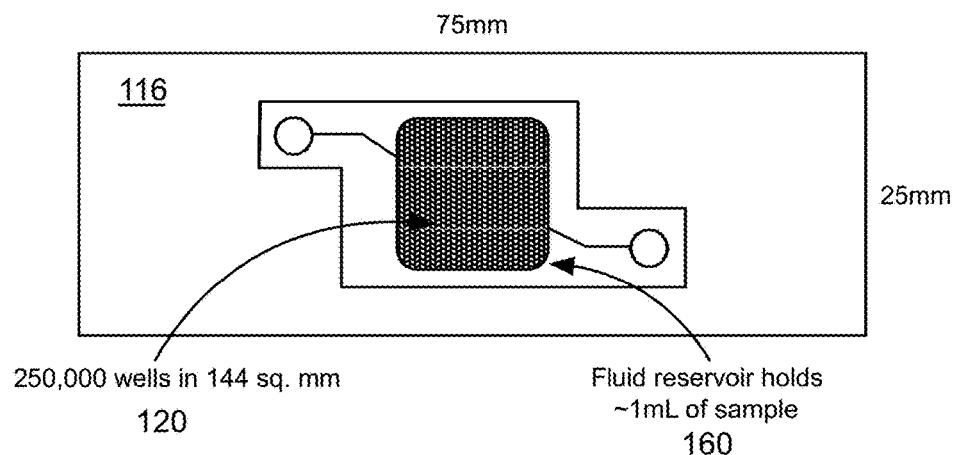
FIGS. 8A-8B depict a variation of a portion a system for isolating and analyzing cells.
Figure 8B:
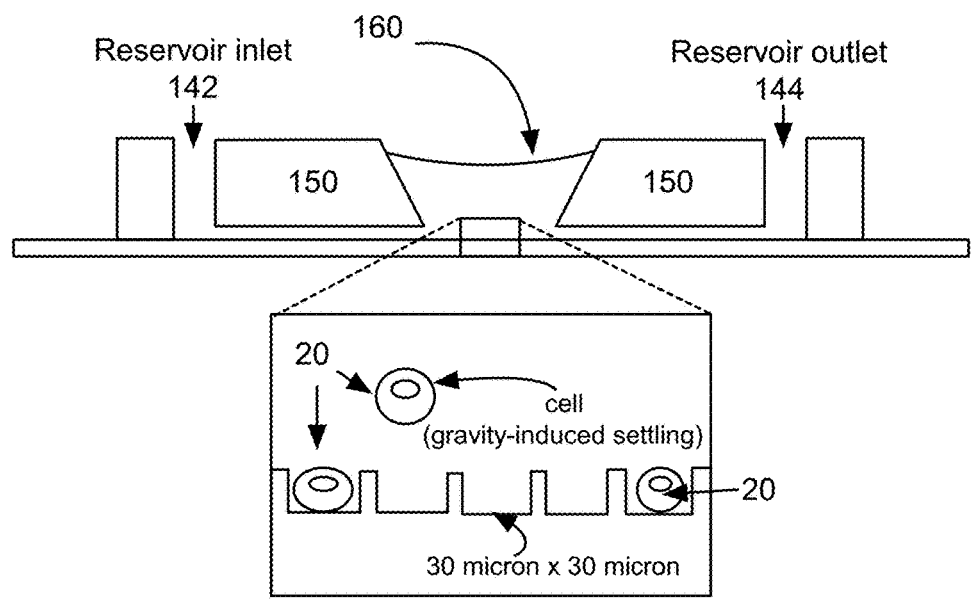

In a specific example of the array of wells, as shown in FIG. 8A, an array of 250,000 wells in 144 mm² can be embossed into a plastic (e.g., material COP480R) using a photolithographic etching process. A fluid reservoir 160 can then be provided (e.g., glued or otherwise attached) around the active region containing the array of wells that allows a relatively large liquid sample to be placed during use (e.g., 0.5 mL to 5 mL). The specific example can further include two microchannels that serve as inlet and outlet to the reservoir fluidly coupled to the array of wells at the active region. Furthermore, as shown in FIG. 8B, a cell-containing sample, (e.g., up to 1 ml in volume), can be dispensed into the fluid reservoir 160 formed by the recessed region of a first plate 150 of a fluid delivery model surrounding the active region of the substrate. Cells present in the sample will settle down (e.g., gravity-induced entry) over time through the fluid layer in the reservoir, and into the interior of the well cavity 128 through the open surfaces of the wells. In specific applications, the settling time depends on the size of the cells; typical cancer cells that are 10-25 microns in size will settle in about 30 minutes. Once the cells enter the well cavities, such that the entire volume of the cells is fully contained within the well cavity 128 (e.g., fully retained, descends below the surface plane 118, descends below the open surface of the well), they are captured in single cell format. Because the walls in between each of the wells in the array of wells are thin (e.g., less than 10 microns thick, less than 5 microns thick, etc.), most of the cells tend to settle inside and fully retained within the well as opposed to on top of or partially retained by the wells. In specific applications with cell-tracker stained cancer cells (SKBR3) spiked in 1 ml PBS, the system 100 demonstrated an over 90% capture efficiency.

Figure 9A:
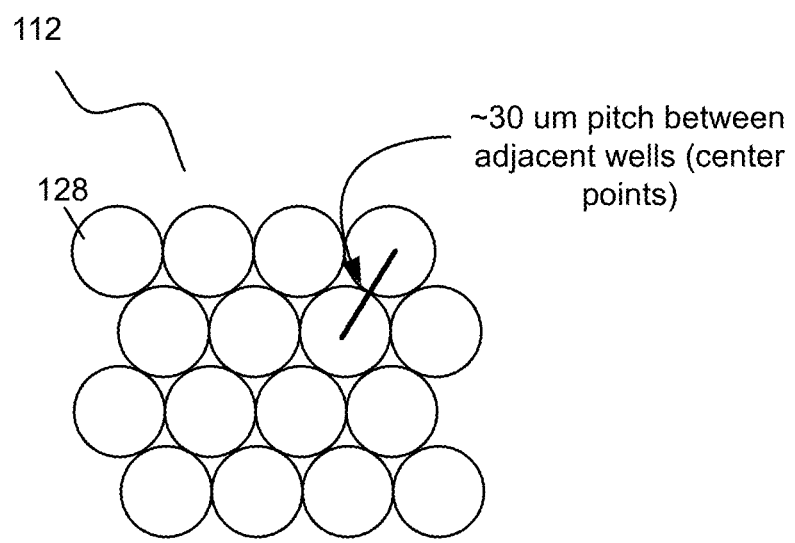
FIGS. 9A-9B depict schematic representations of example configurations of a portion of a system for isolating and analyzing cells.
Figure 9B:
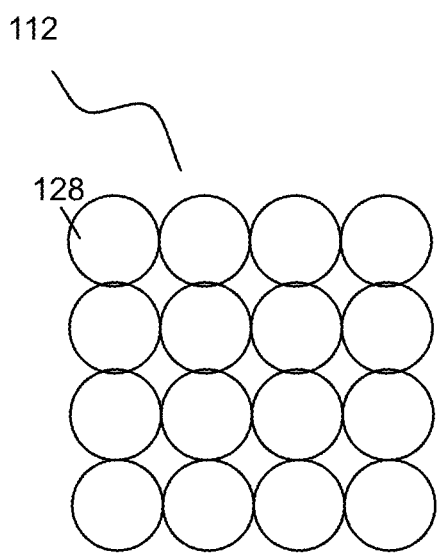

Furthermore, the array of wells 120 is preferably arranged in a packed array, but can alternatively be arranged in any other suitable manner. In one example, the array of wells 120 can be arranged in a hexagonal close-packed array, as shown in FIG. 9A. In another example, the array of wells can be arranged in a rectangular array, as shown in FIG. 9B. In another example, the array of wells 120 can be arranged in any suitable irregular or non-uniform manner, for instance, to facilitate fluid flow from one portion of the array of wells 120 to another portion of the array of wells 120. In a specific example, the shortest distance of the center of each well to the center of an adjacent well of the array of wells is approximately 30 micron. However, the array of wells 120 can alternatively be arranged with any suitable spacing between wells (e.g., in a packed or a non-packed configuration), and in any other suitable manner.

Figure 10:
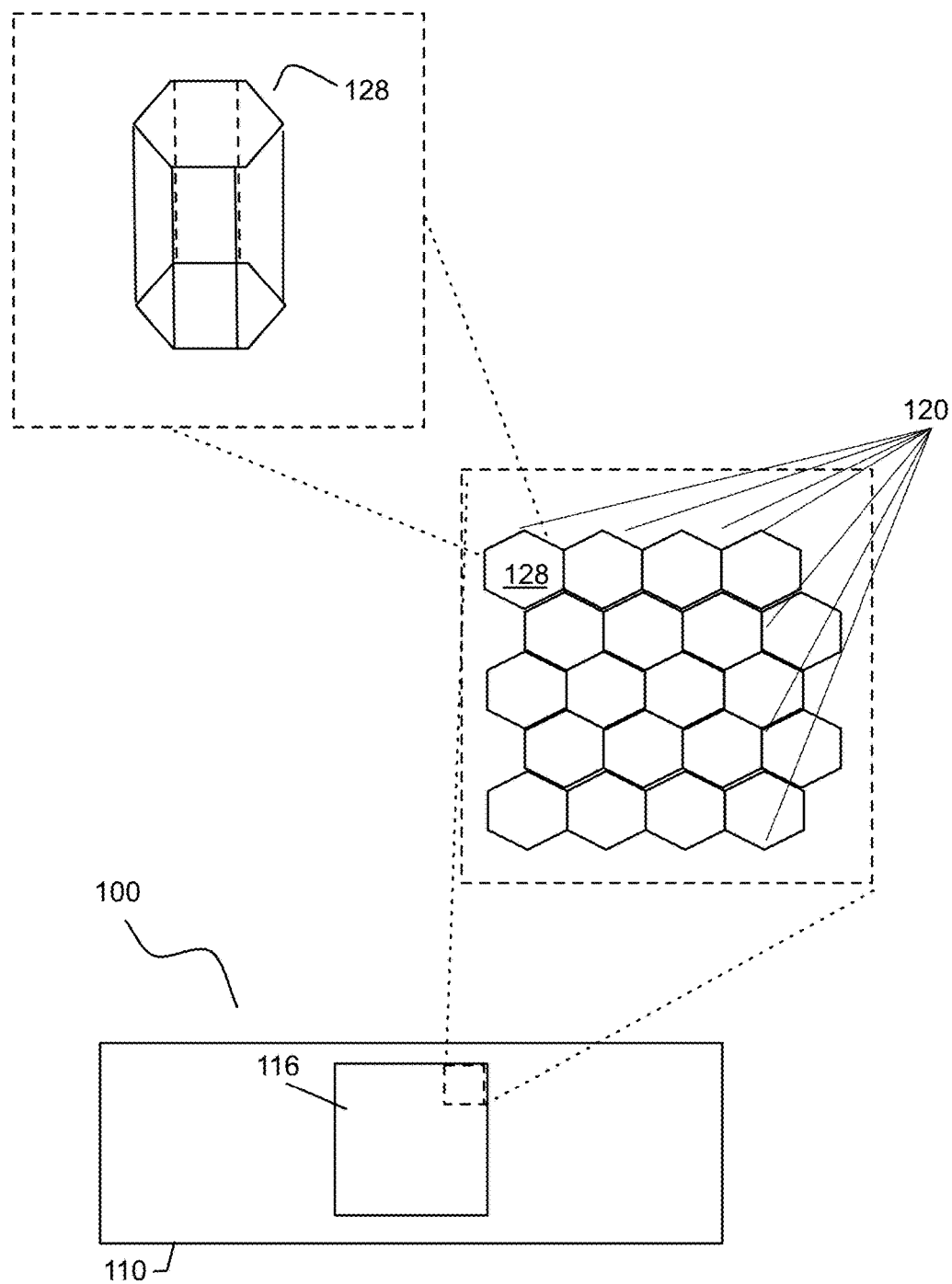
FIG. 10 depicts a schematic representation of a variation of a portion of a system for isolating and analyzing cells.

In a specific example configuration of the set of wells as shown in FIG. 10, the array of wells is arranged in a hexagonal close-packed configuration, wherein each well of the array of wells includes a hexagonal open surface aligned with the broad surface (e.g., surface plane 118) of the substrate. Furthermore, each well includes a hexagonal footprint at the base surface opposing the hexagonal open surface. Each well of the array of wells has a well cavity 128 that forming a hexagonal prism, including a set of walls approximately 5 micron in thickness, a height of approximately 40 micrometers, and a characteristic width of approximately 25 micrometers. The substrate defines 267,000 such hexagonal wells within an active region of the substrate that is approximately 150 square millimeters. However, the array of wells can be configured in any other suitable manner.

In some variations of the system 100, one or more wells of the array of wells 120 can further include any other suitable element that facilitates stimulation and/or detection of a parameter (e.g., a cellular response parameter) at the well(s) of the array of wells 120. In one example, one or more wells of the array of wells 120 of the array of wells 120 can include an electrode embedded in the substrate 110 at a surface of the well 128 in order to facilitate detection of bioelectrical signals from contents of the well 128, and/or to facilitate stimulation of the contents of the well 128. In variations of the example, the electrode can be embedded with an exposed portion at least one of the base surface 124 and a wall 126 of the well 128. In other examples, the well(s) can be coupled to channels that facilitate delivery of process reagents to a cell/cell cluster at a well 128, or facilitate extraction of contents of a well 128 (e.g., processed intracellular contents) from the well 128. The system 100 can, however, include any other suitable element that facilitates processing and/or analysis of cells in at least one of single-cell format and single cluster format.

1.3 System—Fluid Delivery Module

The system 100 can include a fluid delivery module 140 that functions to transfer a sample containing the population of cells, population of particles, and/or another fluid, such as a process reagent and/or distribution fluid, to the array of wells 120, and can be coupled to the substrate. As such, the fluid delivery module can include an inlet 142, an outlet 144 and fluidic guides and/or structures that enable fluid transfer into, out of, and throughout various portions of the system. As shown in at least FIGS. 11A-11B, FIGS. 28A-28C, and FIG. 29, the fluid delivery module 140 can include a first plate 150 arranged proximal the upper broad surface of the substrate 112, a second plate 156 arranged proximal the lower broad surface of the substrate 114, and optionally, a clamping module configured to couple the first plate 150 to the second plate, thereby positioning and/or aligning the substrate 110 between the first plate 150 and the second plate. Alternatively, however, the first plate 150 can be directly coupled to the substrate 110 and/or to any other suitable element of the system 100, such that the fluid delivery module 140 omits a second plate. As such, the fluid delivery module 140 facilities positioning of the substrate 110 to receive and/or seal the sample or fluid at the array of wells 120 (e.g., with a compressive force, with a hermetic seal, etc.). Additionally or alternatively, the fluid delivery module 140 can include a fluid reservoir 160 defined between the first plate and the broad surface of the substrate, and providing a region for a fluid path 162 that facilitates controlled fluid flow through the reservoir across the array of wells 120.

Figure 30A:
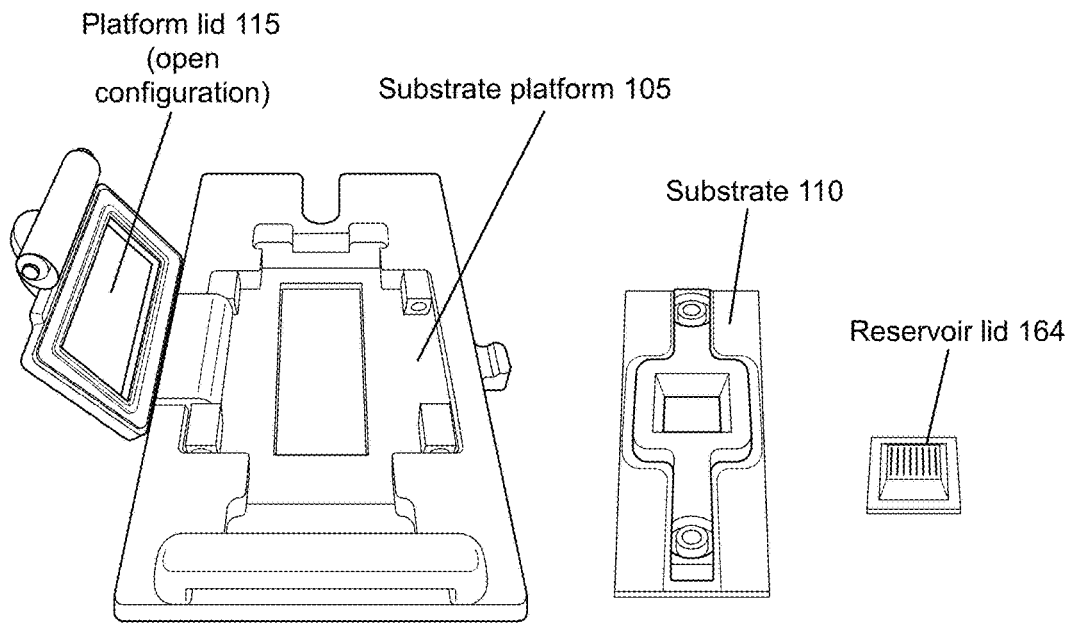
FIG. 30A-30B depict an example of a variation of a portion of a system for isolating and analyzing cells.
Figure 30B:
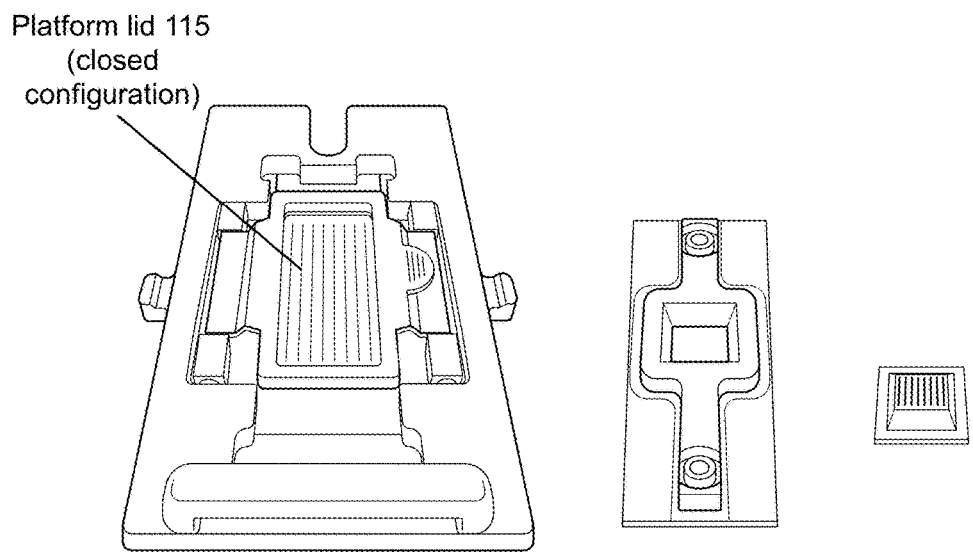
Figure 31C:
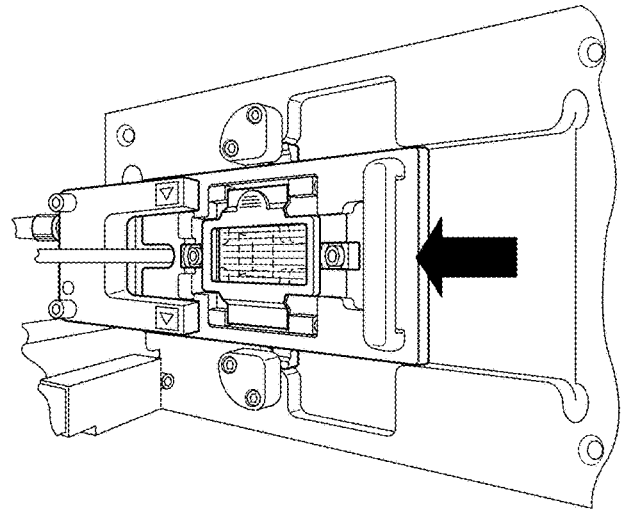
FIG. 31A-31C depict an example of a variation of a portion of a system for isolating and analyzing cells.
Figure 31B:
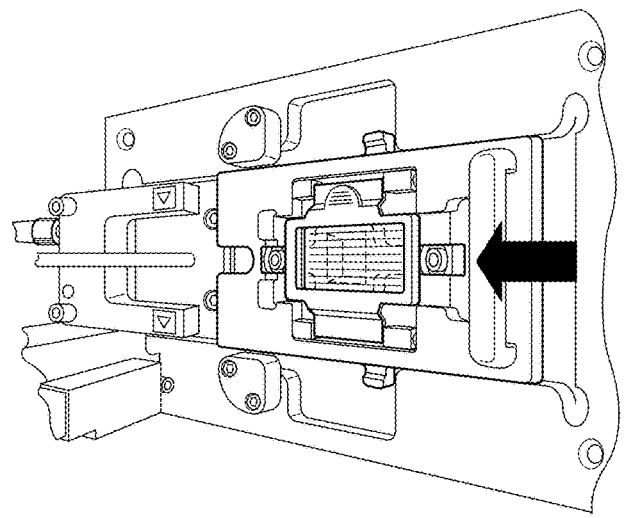
Figure 31A:
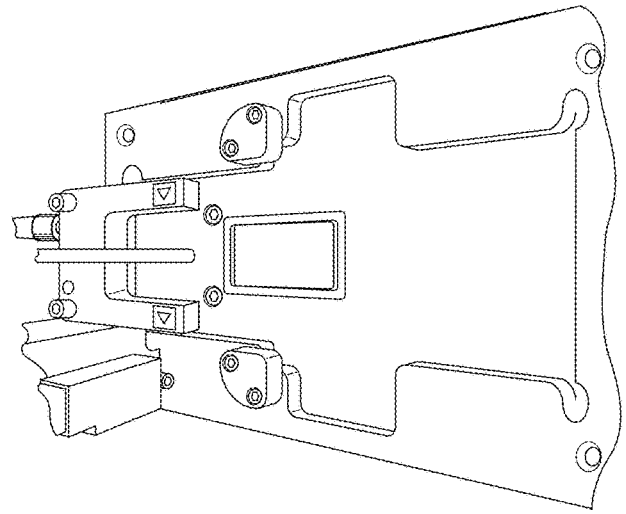
Figure 33:
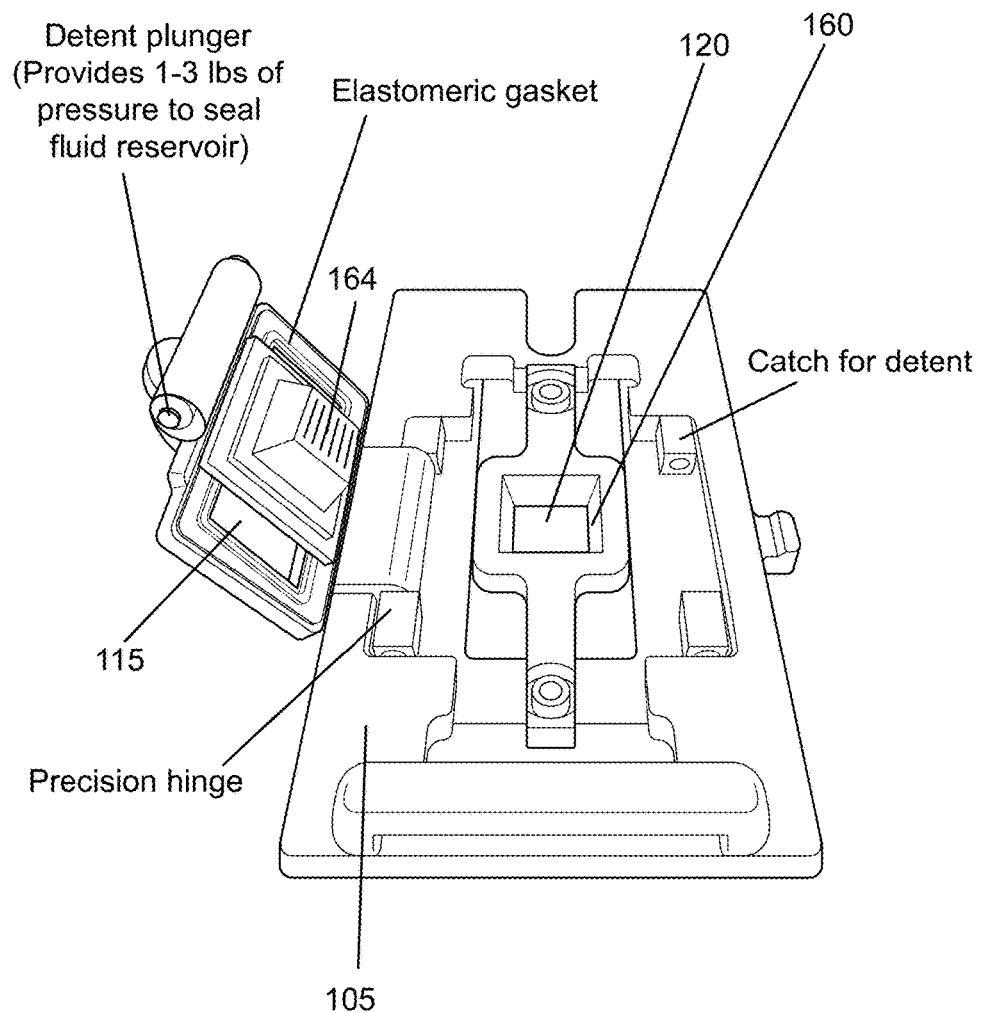
FIG. 33 depicts an example of a variation of a portion of a system for isolating and analyzing cells.

In variations, the first plate 150 can have a rectangular footprint that spans the upper broad surface 112 of the substrate 110. However, the first plate 150 can alternatively have any other suitable footprint (e.g., non-rectangular footprint, circular footprint, ellipsoidal footprint, etc.) configured to span all or a portion of the upper broad surface 112 of the substrate 110. In preferred variations, as shown in FIGS. 28A-28C and FIG. 29, the first plate 150 includes an opening or recess 152 to be positioned over the array of wells 120. When the first plate 150 is attached to the substrate 110, the recess 152 of the first plate 150 defines the fluid reservoir 160 against the array of wells. The fluid reservoir 160 can be sealed by a reservoir lid 164, and additionally and/or alternatively be placed within a substrate platform lid 115 (as shown in FIGS. 30A-30B, and FIG. 33), that can optionally include an elastomeric gasket and a detent plunger to hermetically seal the reservoir lid into the fluid reservoir. In another variation shown in FIGS. 11A and 11B, the first plate 150 includes a recess 152 at one side of a closed surface of the first plate and facing the upper broad surface 112 of the substrate 110, such that the recess 152 and the upper broad surface 112 cooperatively define a lumen that can be fluidly connected to an inlet 142 and outlet 144 of the fluid delivery module. The lumen of the recess 152 preferably functions as a fluid reservoir 160 to temporarily hold a sample and/or a processing reagent proximal to the array of wells 120 (e.g., in a fluid layer and/or fluid path 162 occupying the lumen defined by the recess and the broad surface of the substrate). As such, the recess 152 preferably spans the active region of the substrate at which the array of wells 120 is defined, and aligns with the array when the first plate 150 is coupled to the substrate 110. The lumen (e.g., fluid reservoir) can have any suitable volume, preferably defined by the product of the gap distance between the base surface of the recess and the projected area of the recess. The gap distance (e.g., height of the fluid reservoir) is preferably between 25 microns and 5 mm, but can alternatively be any suitable distance.

Figure 11A:
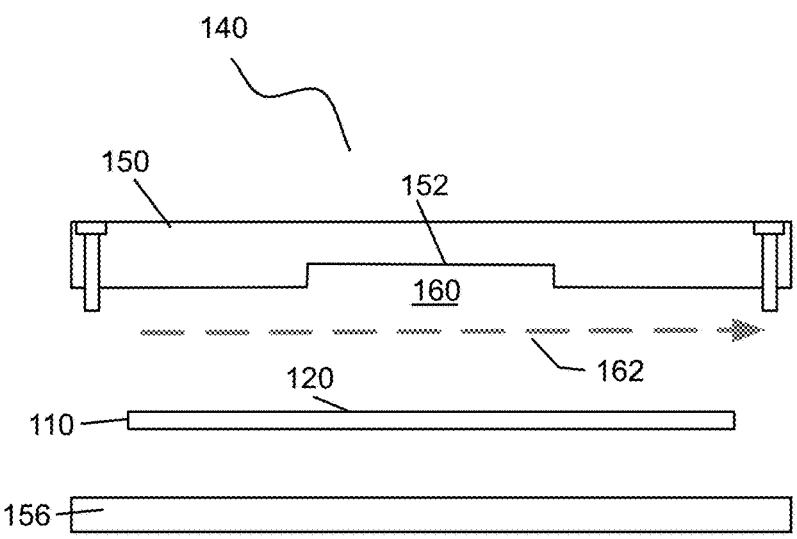
FIGS. 11A-11B depict a schematic representation of a variation of a portion of a system for isolating and analyzing cells.
Figure 11B:
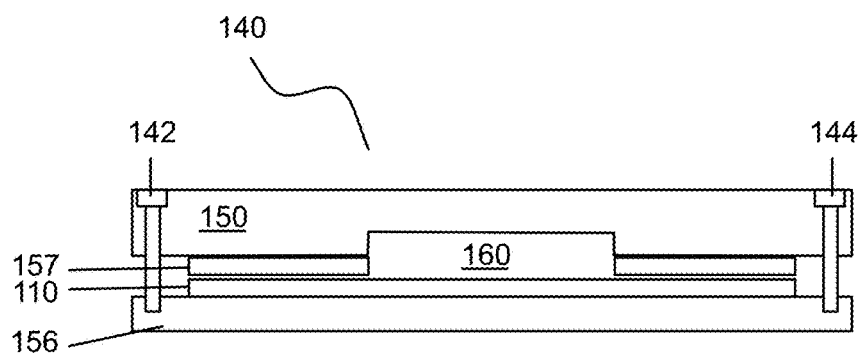

In one variation, the recess 152 can be a rectangular recess defined within the surface of the first plate 150 facing the substrate 110. Furthermore, the recess can have a substantially planar base surface, as shown in FIGS. 11A and 11B, or any other suitable base surface (e.g., non-planar base surface). However, the recess 152 can alternatively have any other suitable morphology. Additionally or alternatively, the recess 152 can include a sealing element 157 (e.g., o-ring, sealant, etc.) surrounding a region of the recess 152 proximal the substrate 110, in order to provide a hermetic seal upon coupling of the first plate 150 to the substrate 110. Additionally or alternatively, the sealing element can be located on the substrate platform lid 115 and secured to the first plate in a closed configuration (FIG. 33). However, the first plate 150 can alternatively be configured in any other suitable manner.

The second plate is configured proximal to a surface of the substrate 110, directly opposing the broad surface of the substrate 110, and functions to provide a base to which the first plate 150 can be coupled, thereby positioning the substrate 110 between the first plate 150 and the second plate. The second plate preferably provides a complementary surface to which the surface of the substrate 110, opposing the upper broad surface 112, can be coupled. In one variation, the second plate is a substantially planar, in order to provide a surface to which a planar surface of the substrate 110 (e.g., a planar surface directly opposing the broad surface of the substrate) can be coupled; however, the second plate can be configured relative to the substrate 110 in any other suitable manner. Furthermore, the second plate can include an aligning element that facilitates alignment of the second plate relative to the substrate no and/or to the first plate 150. In variations, the aligning element can include any one or more of: a protrusion and/or a recess at the second plate that facilitates alignment, a track that facilitates alignment, a magnetic element, and any other suitable alignment element.

In one variation, the first plate 150 is preferably coupled to the second plate with a coupling mechanism that can include one or more of: a pin, a screw, a magnetic coupler, a clamp, and any other suitable coupling mechanism. To prevent obstruction, the coupling mechanism can be located at peripheral portions of the system (e.g., at peripheral portions of the first plate 150, the second plate, and/or the substrate 110), or at any other suitable location that does not interfere with function of the substrate. Alternatively, some variations of the system 100 may omit the second plate, and have direct coupling between the first plate 150 and the substrate 110 in any suitable manner.

As shown in FIGS. 2A-2C and FIG. 14, some variations of the fluid delivery module 140 can include a set of inlet and outlet channels (e.g., a set of fluidic pathways 146 associated with respective manifold inlets 440 and manifold outlets 442) linking an inlet 142 of the system 100 to each of the array of wells 120 and additionally or alternatively, the array of wells 120 to an outlet 144, wherein the outlet is fluidly coupled to a receptacle for collecting removed fluids and/or sample fluid from the array of wells (e.g., to contain waste, to contain excess reagent, to collect desired sample for downstream processing). The set of fluid pathways 146 functions to distribute and route desired fluids (e.g., reagent-containing fluids, sample containing fluids, etc.) to the array of wells 120 at substantially consistent fluid flow rates and volumes. The set of fluid pathways 146 can have any suitable correspondence with the set of wells; for example, there may be one fluid pathway per single well 128, multiple fluid pathways 146 per single well 128, and/or one fluid pathway connected to multiple wells. In another example, the set of fluid pathways 146 is a network of fluid pathways 146 that branches from a single fluid pathway, connected to the inlet 142, into a set of fluid pathways 146 connected to each well individually such that the total length of any fluid pathway between the inlet and a well is substantially equal in length (e.g., exactly equal length, equal to within 10-100 microns, equal to within a characteristic length for a given flow rate and pathway cross-section, equal to within any suitable threshold length, etc.). The set of fluid pathways 146 can additionally or alternatively include fluid pathways 146 that connect groups and/or subsets of wells to an inlet, as well as to other groups and/or subsets of wells. Each of the subsets thus connected can include an identical number of wells, but can alternatively have differing numbers of wells in each subset connected by the set of fluid pathways 146.

In an example, the fluid delivery module comprises the first plate 150, and the first plate 150 defines an inlet 142 and an outlet 144. The plate further defines a recessed region 152 that is fluidly connected to the inlet, and that faces the broad surface of the substrate so as to define a contiguous lumen (e.g., fluid reservoir 160) cooperatively with the array of wells 120. The fluid delivery module is operable in a cell capture mode, in which a fluid sample containing a population of cells and/or a distribution fluid used to re-distribute deposited cells is flowed into the fluid reservoir 160 between the inlet and the outlet (e.g., by a pressure differential). In this example, the fluid sample is flowed substantially parallel to the broad surface of the substrate through a fluid path 162. The sample is flowed at a flowrate (e.g., at least 0.5 millileters per second, 1 millileter per second, 1 millileter per minute, 1 microliters per second, 10 microliters per second, 100 microliters per second, etc.), and the flowrate is selected (e.g., controlled) such that the combination of vertical forces on the single cells (e.g., gravitational, buoyancy, etc.) is directed toward the broad surface, and is greater the lateral pressure forces from the surrounding fluid so as to promote settling of the single cells into the set of wells from the laterally flowing sample.

The fluid reservoir 160 functions to receive a biological sample including cells of interest and at least one fluid from the fluid delivery module 140, and to deliver the biological sample and at least one fluid to the set of fluid pathways 146 (e.g., of a manifold, an inlet manifold, an outlet manifold) to facilitate cell capture and/or analysis. In a first variation, the fluid reservoir 160 includes an opening to atmospheric pressure, such that fluid delivery from the fluid reservoir 160 in an inlet-to-outlet direction is enabled by negative pressure applied by a pump in communication with a flow control subsystem 180 and coupled indirectly to the fluid reservoir 160 by at least one of the set of fluid pathways 146 and the waste chamber. In the first variation, the negative pressure applied can be reversed in order to facilitate flow in an outlet-to-inlet direction. In a second variation, the fluid reservoir 160 may not include an opening to atmospheric pressure, but can alternatively be coupled to a pump configured to provide positive pressure and negative pressure at the fluid reservoir 160, in order to facilitate flow in both an inlet-to-outlet direction and an outlet-to-inlet direction, respectively. In a specific example of the second variation, the fluid reservoir 160 is coupled to a syringe pump configured to provide positive and negative pressure by manual pumping. Fluid delivery from the fluid reservoir 160 to the manifold can, however, be performed in any alternative suitable manner.

The fluid reservoir 160 can further comprise a level sensor, configured to detect fluid level within the fluid reservoir 160, which functions to prevent gas bubbles from entering the set of fluid pathways 146. As such the level sensor can generate a signal upon detection of a trigger fluid level (e.g., a low fluid level as a threshold), and transmit the signal to a processor configured to receive the signal and generate a command to control fluid delivery (e.g., via the flow control subsystem 180) into the set of fluid pathways 146 based upon the signal. The command can be used to automatically stop fluid flow from the fluid reservoir 160 into the set of fluid pathways 146, and/or can function to implement control of fluid flow in any other suitable manner. In variations of the fluid reservoir 160 comprising a level sensor, the level sensor can be a load cell, an ultrasonic level sensor, or any suitable signal configured to generate a signal when fluid level in the fluid reservoir 160 passes a certain threshold. Detection of the signal can then generate a response to stop fluid flow within the system 100 and/or a response to add more fluid to the fluid reservoir 160, thus preventing gas bubbles from entering the manifold. In a specific example, the fluid reservoir 160 has a volumetric capacity greater than 6 mL, is configured to couple to the manifold inlet 160 by a threaded male-female coupling, and comprises an opening to atmospheric pressure, wherein the opening can also couple to a syringe pump. In the specific example, the fluid reservoir 160 further comprises an ultrasonic level sensor configured to generate a signal when fluid level in the fluid reservoir 160 passes a certain threshold. Other variations of the system 100 can altogether omit the fluid reservoir 160 and use a network of fluid delivery conduits, with or without valves, to deliver at least one fluid to the set of fluid pathways 146.

1.3.1. Fluid Delivery Module—Cartridge

Figure 12A:
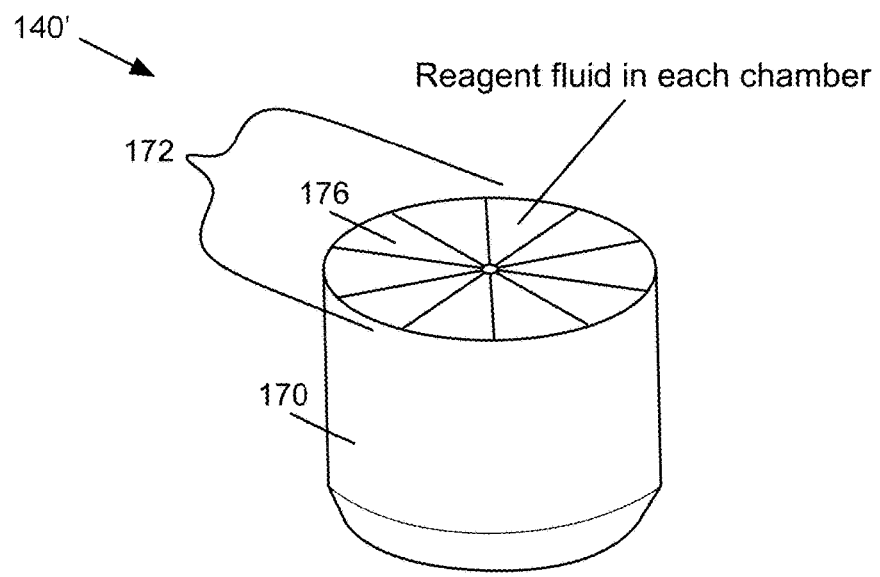
FIGS. 12A-12B depict a variation of a portion of a system for isolating and analyzing cells.
Figure 12B:
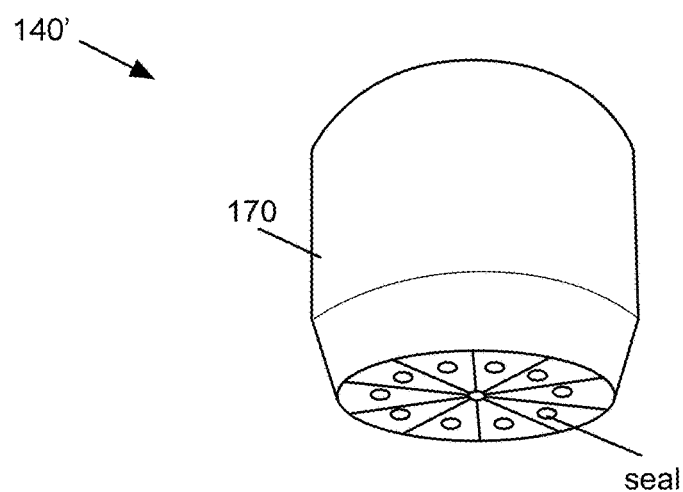

The fluid delivery module 140 further functions to contain and deliver at least one fluid to the fluid reservoir 160, in order to facilitate capture and/or analysis of cells within the array of wells. Preferably, as shown in FIGS. 12A and 12B, the fluid delivery module 140 comprises a reagent cartridge 170 having a set of reagent chambers 172, each reagent chamber 176 in the set of reagent chambers configured to contain a fluid of a set of fluids to facilitate capture and/or analysis of cells. The cartridge 170 can be cylindrical, conical, frustoconical, prismatic, pyramidal, or of any other suitable morphology. Each reagent chamber 176 in the set of reagent chambers 172 is preferably identical to the other chambers, but can alternatively be non-identical to other reagent chambers based on fluid storage requirements (e.g., volume requirements, temperature requirements, light exposure requirements, pressure requirements). The set of fluids preferably comprises reagents including buffers (e.g., priming, wash, and permeabilization buffers), fixing solutions (e.g., pre-fixing and post-fixing solutions), and cocktails (e.g., lysis, inhibitor, primary antibody, and secondary antibody cocktails), and can additionally or alternatively comprise stains (e.g., fluorescent stains or histological stains) and any other suitable fluids for cell capture or analysis. In a first example, the set of fluids can include reagents used to perform on-chip cDNA synthesis from captured mRNA, including lysis buffers, RNase inhibitors, and dNTPs. In a second example, the set of fluids can include reagents used to perform exonuclease treatment of the contents within the array of wells to remove any single-stranded oligonucleotide sequence (e.g., from a captured population of particles containing oligonucleotide probes). In a third example, the set of fluids can include reagents for cDNA amplification using PCR master mix, dNTPs and primer sets. In a fourth example, the set of fluids can include reagents for targeted amplification of products (e.g., genetic material, set of genetic complexes produced in variations of method 200) from the nucleic acid recovered from single cells. In a fifth example, the set of fluids can include enzyme mixes and oligonucleotide sequences for ligating specific oligonucleotide sequences to single cell DNA or RNA. In a sixth example, the set of fluids can include enzymes mixes for tagmentation and labeling of nucleic acids. In a seventh example, the set of fluids can include reagents that contain a population of SPRI beads used for size-based purification and elution of nucleic acids of specific base pair lengths. However, the set of fluids can be otherwise configured and can include any other suitable combination of reagents for any assay that can be performed by system 100 and/or method 200. In variations of the system 100 configured to further promote purification of captured cells by magnetic separation, the set of fluids can also comprise solutions of magnetic beads coupled with affinity molecules configured to bind to components of interest (e.g., undesired cells, fragments, waste products) within a biological sample. In one example, a reagent chamber 176 can contain a solution of streptavidin-coated magnetic microparticles, configured to bind to CD45-bound white blood cells (WBCs). In alternative variations, the fluid delivery module 140 can comprise a single chamber configured to facilitate delivery of a single fluid or multiple fluids to facilitate capture and/or analysis of cells within a biological sample. In other variations, the chamber(s) of the fluid delivery module 140 can be replaced by any suitable fluid conduit(s).

The fluid delivery module 140 is preferably configured to be prepackaged with at least one fluid (e.g., reagent, buffer, cocktail, stain, magnetic particle solution, etc.) inside a chamber, which functions to facilitate capture and/or analysis of cells of interest according to a specific, pre-defined protocol. Alternatively, the fluid delivery module 140 can be prepackaged in an open or semi-open configuration, such that a user can transfer at least one fluid into at least one reagent chamber 176 of the fluid delivery module 140 to facilitate capture and/or analysis of cells of interest according to a different protocol. Preferably, at least part of the fluid delivery module 140 is configured to be consumable, such that a portion of the fluid delivery module 140 can be disposed of after one use or multiple uses. Alternatively, the fluid delivery module 140 can be configured to be reusable, such that fluids can be repeatedly transferred to a reusable fluid delivery module 140 configured to transfer fluids to the fluid reservoir 160.

In embodiments of the fluid delivery module 140 comprising a cartridge 170 having a set of reagent chambers 172, each chamber is preferably configured to be isolated from other reagent chambers and individually accessible, which functions to control delivery of a specific fluid to the fluid reservoir 160. In a first variation, the fluid delivery module 140 comprises a set of reagent chambers 172, and comprises at least one seal configured to seal the set of reagent chambers 172, thus isolating each chamber in the set of reagent chambers from other chambers. The seal in the first variation is a puncturable foil seal, such that puncturing the seal at a chamber location provides access to the reagent chamber 176. In an example of the first variation, each chamber is sealed at two locations and puncturing the seal at the two locations exposes the chamber to atmospheric pressure, facilitating delivery of a fluid within the chamber, through a location of puncture, to the fluid reservoir 160 by means of hydrostatic pressure. In another example of the first variation, each chamber is sealed and puncturing the seal at a puncture location, while providing a positive pressure at the puncture location (e.g., using a hypodermic needle, using a syringe pump, etc.) facilitates delivery of a fluid within the chamber to the fluid reservoir 160. In yet another example of the third variation, each chamber is sealed and applying negative pressure at a chamber location (e.g., through a valve or an opening) facilitates delivery of a fluid within the chamber to the fluid reservoir 160. Puncturing a seal, applying positive pressure, and/or applying negative pressure at a chamber can be performed manually, or can alternatively be performed automatically using an actuation system configured to enable access to contents of reagent chambers of the cartridge 170. The fluid delivery module 140 can alternatively facilitate individual access and/or isolation of a reagent chamber 176 using any other suitable mechanism or combination of elements.

In a first specific example, as shown in FIGS. 12A and 12B, the fluid delivery module 140' comprises a substantially cylindrical cartridge 170 comprising ten identical isolated reagent chambers 176, each configured to contain a fluid or reagent to facilitate cell capture and/or analysis. In the first specific example, the cylindrical cartridge 170 can have one of an open configuration comprising open chambers, a semi-open configuration comprising open reagent chambers and sealed reagent chambers with prepackaged reagents, and a completely sealed configuration comprising sealed reagent chambers with prepackaged reagents. In semi-open or sealed configurations, sealed reagent chambers are sealed at two ends with a puncturable foil seal, and in open or semi-open configurations, open reagent chambers are sealed at one end with a puncturable foil seal. Each of the ten reagent chambers has a volumetric capacity of 4-6 mL and has a wedge-shaped cross section that is substantially uniform along a majority of a 2" length. In the first specific example, the cartridge 170 has a bevel at an inferior region of the cartridge 170, as shown in FIG. 12B, in order to facilitate fluid flow toward an inferior region of the cartridge 170, proximal the seal.

The fluid delivery module 140' of the first specific example can also be coupled to an actuation system configured to individually access each chamber of the cylindrical cartridge, in order to facilitate automatic delivery of a fluid within each chamber to the fluid reservoir 160. The actuation system of the first specific example comprises a rotary shaft driven by a stepper motor, wherein the rotary shaft is mounted to the cylindrical cartridge. In the first specific example, the rotary shaft is mounted along an axis of rotation (e.g., a vertical axis of rotation) of the cartridge 170, such that the ten reagent chambers 172 surround the axis of rotation. This configuration, along with the stepper motor, functions to allow determination of the positions of the ten reagent chambers 172 as the cartridge 170 rotates during operation. The actuation system of the first specific example also comprises a first actuator configured to provide relative displacement between a first piercer and the cartridge 170, in order to facilitate piercing of a seal of a single reagent chamber 176 of the cartridge 170. In the first specific example, the first piercer is situated inferior to the cartridge 170, and comprises a puncturing tip, that aligns with reagent chambers 172 of the cartridge 170 in different rotational configurations of the cartridge 170, wherein the puncturing tip is proximal to (e.g., concentric with) and coupled to (e.g., contiguous with) a boundary of an aperture of the first piercer. As such, piercing of a seal of the cartridge 170 at a chamber location, by way of the puncturing tip, facilitates flow of contents of the chamber(s) through the aperture of the first piercer and into a fluid reservoir 160 configured to receive chamber contents. In some variations, the puncturing tip may also have an opening (e.g., an opening into a vertical channel, a slanted channel, or a channel with any other suitable orientation or path) to allow fluid to flow from the cartridge 170 to the fluid reservoir 160. Additionally or alternatively, the structure of the puncturing tip can extend below the surface of the first piercer to allow fluid to drip in a guided fashion toward the fluid reservoir 160.

In one variation of the first specific example, the actuation system can displace the piercer relative to the cartridge 170 (e.g., in a vertical direction, in a non-vertical inferior-superior direction) in order to drive the piercer into a seal of the cartridge 170. In this variation, the first piercer can be coupled to a drip plate that facilitates fluid delivery into the fluid reservoir 160. In another variation of the first specific example, the actuation system can displace the cartridge 170 relative to the piercer (e.g., in a vertical direction, in a non-vertical inferior-superior direction), in order to drive the seal of the cartridge toward the puncturing tip of the piercer. In still other variations of the first specific example, the actuation system can displace one or both of the cartridge 170 and the piercer in any other suitable direction (e.g., vertical direction, a direction angularly displaced from a vertical direction, a horizontal direction) in order to enable piercing of a seal of the cartridge 170. As such, in some variations of the first specific example, the cartridge 170 and/or the piercer can be tilted away from a vertical or horizontal configuration. In tilted variations, fluid flow can be facilitated by gravity and/or application of positive or negative pressure to a reagent chamber 176 of the cartridge 170.

In a second specific example of the fluid delivery module 140'', the actuation system comprises a first actuator configured to drive a first piercer to puncture a seal at a first end of a reagent chamber 176, and a second actuator configured to drive a second piercer configured to create an opening in a second end of the reagent chamber 176. Puncturing the first end of the reagent chamber 176 functions to vent the first end of the reagent chamber 176 to atmospheric pressure, in order to facilitate fluid delivery from the reagent chamber 176, and creating an opening in a second end of the reagent chamber 176 functions to allow fluid within the reagent chamber 176 to flow from the reagent chamber 176, to the fluid reservoir 160, due to hydrostatic pressure. In the second specific example, the first actuator is a solenoid actuator configured to linearly displace the first piercer relative to a chamber, and to drive the first piercer into a puncturable foil seal at a first end of the chamber. The second actuator is a rotary solenoid actuator configured to convert rotary motion into linear motion, such that the second piercer coupled to the rotary solenoid actuator creates an opening in chamber through a puncturable foil seal at a second end of the reagent chamber 176. The first actuator and the second actuator, however, can be replaced or supplemented by any suitable actuator (e.g., pneumatic or hydraulic actuator) or multiple actuators in variations of the second specific example. Furthermore, variations of the first and the second specific examples can include any suitable actuator(s) that enable a piercer to provide access to contents of a reagent chamber 176. Similarly, the stepper motor of the first and the second specific examples can be replaced or supplemented by any suitable actuator or element that enables determination of actuator position (e.g., an actuator coupled to a linear encoder). Thus, the actuation system of the first and the second specific examples facilitates rotation of the cartridge 170 to position individual reagent chambers 176 into alignment with at least one piercing element using a stepper motor, and facilitates puncturing of individual reagent chambers using a subsystem of one or more actuators.

Figure 13A:
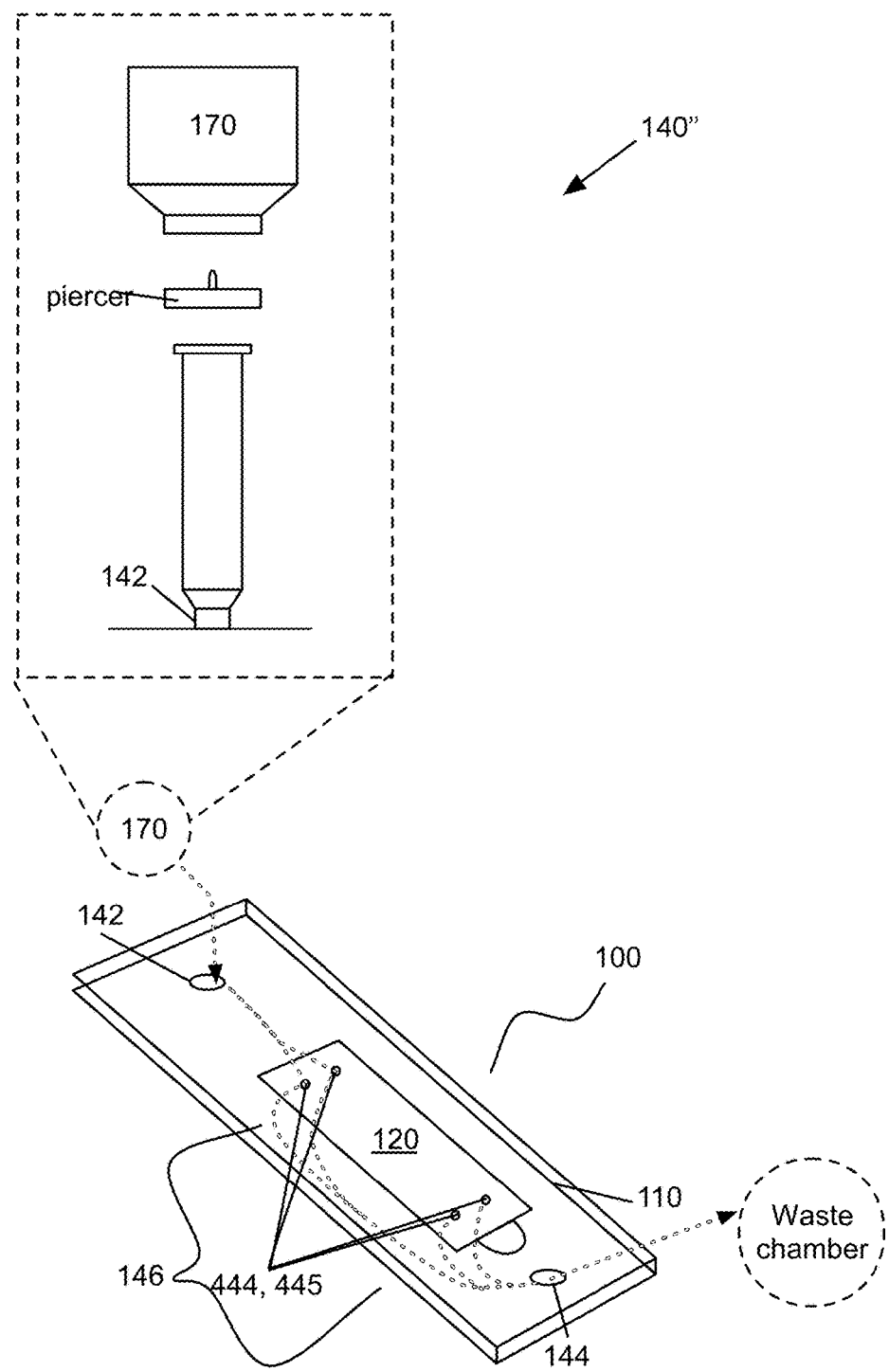
FIG. 13A depicts an variation of a portion of a system for isolating and analyzing cells.
Figure 13B:
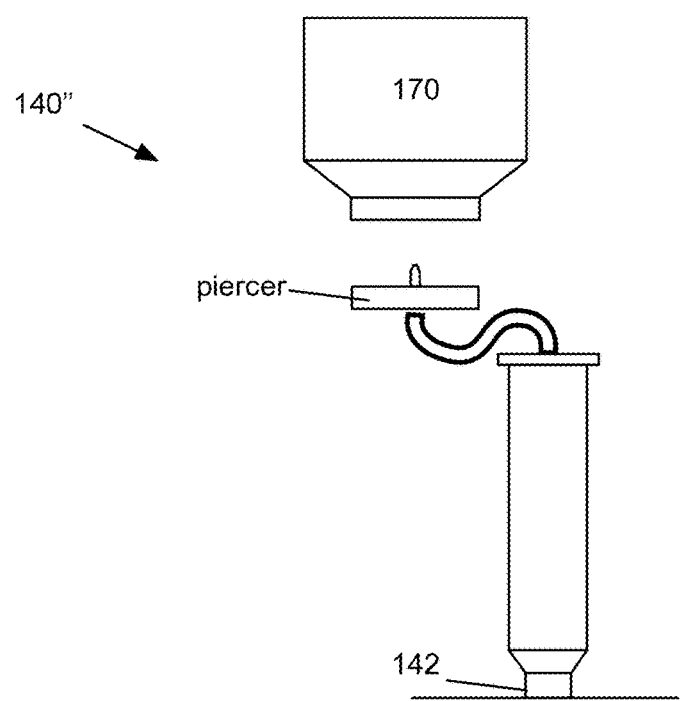
FIG. 13B depicts a variation of a portion of a system for isolating and analyzing cells.
Figure 14:
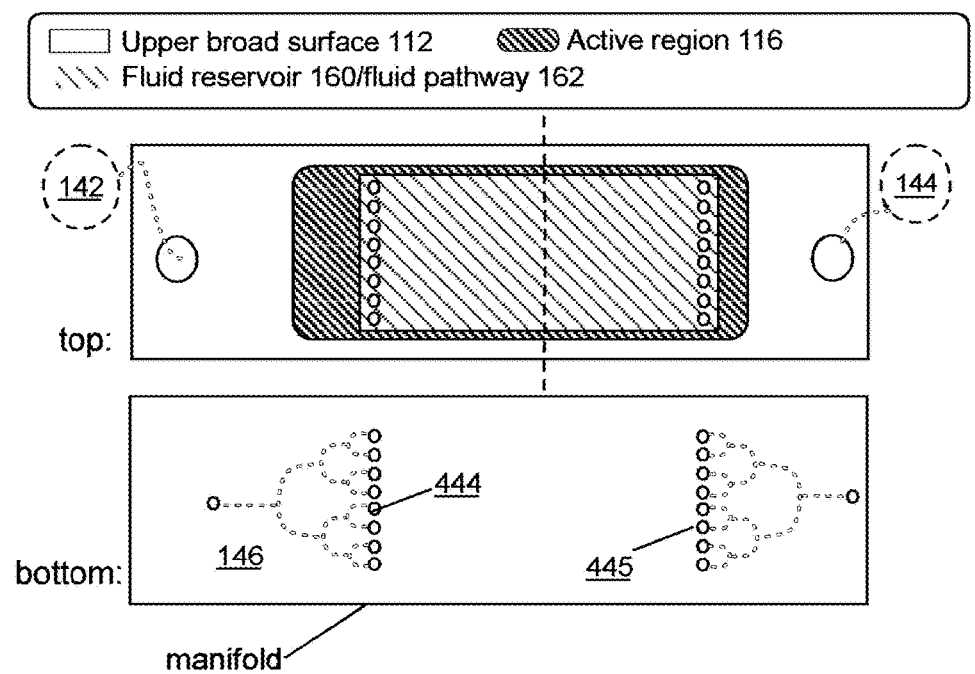
FIG. 14 depicts a variation of a portion of a system for isolating and analyzing cells.

In both of the first and the second specific examples, the rotation of the cartridge positions a desired reagent chamber 176 directly into alignment with (e.g., directly over) a fluid inlet 142 coupled to the fluid reservoir 160 and configured to receive and distribute contents of the reagent chamber 176 into a manifold (e.g., set of fluid pathways 146), as shown in FIG. 13; however, in variations of first and the second specific examples, the cartridge 170, the reagent chamber 176, and/or the fluid reservoir 160 may be out of alignment (e.g., offset), but fluidly coupled in any suitable manner to facilitate fluid flow from a reagent chamber 176 to the fluid reservoir 160. In one example, as shown in FIG. 13B, the fluid reservoir 160 can be out of alignment with the reagent chamber 176 of the cartridge, but coupled to a piercer (or the reagent chamber 176) using a fluid conduit (e.g., a flexible fluid conduit). Furthermore, still other variations of the first and the second specific examples can omit rotation of a cartridge 170, or can additionally or alternatively include translation of a cartridge (e.g., in X, Y, and/or Z directions) to align desired cartridge reagent chambers 112 for delivery of processing fluids to a fluid reservoir 160. Furthermore, still other variations can include keeping the reagent cartridge fixed at a location (e.g., without rotating to access a piercer and/or inlet), and extracting fluid from the top of a desired reagent chamber using a pipettor or capillary to aspirate and dispense fluid into the fluidic manifold, inlet, fluid reservoir, fluid pathways, and/or outlet of the array of wells as needed.

1.3.2 Fluid Delivery Module—Flow Control Subsystem

The system 100 can additionally include a flow control subsystem 180 configured to control fluid and/or sample flow through the system 100, as well as reagent flow or the flow of any other suitable fluid through the system. The flow control subsystem is preferably operable in a flow mode, in which the flow control system applies a pressure gradient between the inlet and outlet of the fluid delivery module. The pressure gradient can be a positive pressure gradient (as defined between the inlet and outlet) or a negative pressure gradient, and it may be applied continuously, periodically, asynchronously, in a reciprocating fashion (e.g., between positive and negative), or in any other suitable manner. In variations, the flow control subsystem comprises a pump configured provide at least one of positive pressure and negative pressure, and functions to facilitate fluid flow through the system 100. Preferably, the pump 182 is configured to provide both positive pressure and negative pressure, such that fluid can flow in a forward direction and in a reverse direction within an element of the system 100. Flow in a forward direction preferably facilitates capture of cells of interest from a biological sample, and flow in a reverse direction preferably facilitates retrieval and/or analysis of cells of interest from the biological sample. Preferably, the pump 182 is configured to couple to the waste chamber and comprises a multi-way valve configured to provide a connection at least between the pump 182 and the atmosphere, and between the pump 182 and the waste chamber. The pump 182, however, can additionally or alternatively be coupled to any suitable element of the system to facilitate fluid flow, comprise a valve configured to provide any suitable alternative connection, and/or may not comprise a multi-way valve 162. In some variations, the pump 182 can also comprise a pressure sensor, which functions to enable measurement of a pressure provided by the pump 182. In one example, the pump 182 is a syringe pump, however, the pump 182 can be any suitable pump configured to provide at least one of a positive pressure and a negative pressure to facilitate fluid flow within the system 100. In order to minimize damage to cells, the pressures used for fluid delivery are low (e.g., less than 2 psi or less than 1 psi). In preferred variations, the pumping system can control pumping pressures as low as 0.1 psi.

1.4 System—Thermal Control Module

The system 100 can additionally include thermal control module 190 that functions to heat and/or cool the substrate and its contents, in order to control the temperature of contents of the set of wells and/or fluid delivery module during operation of the system 100. In variations, the thermal control module can heat and/or cool a biological sample containing cells of interest and/or a fluid to facilitate cell capture and analysis, and can further function to facilitate reactions requiring cycling from low to high temperatures, such as for cell lysis, enzyme activations for probe hybridizations and thermocycling of biological sample mixtures for molecular diagnostic protocols, such as polymerase chain reaction (PCR). The thermal control module 190 can comprise a heater, a heat sink, a sensor, a fan, and one or more processors, however; the thermal control module can include any suitable component to sense and modulate the temperature of the array of wells, and according to any instruction (e.g., user-input, automatically, pre-set temperature schedule, according to a particular assay, etc.). In variations, the heater 192 of the thermal control module is preferably a thin heater (e.g., Peltier device) configured to controllably heat and cool the biological sample and/or fluid. The thermal control module 190 can additionally and or alternatively comprise a temperature sensor, or any other suitable element configured to facilitate temperature control. For example, the temperature sensor can couple to a heat-conductive substrate, to a heating element, or to a plate-shaped heater. Temperature control can be enabled using pulse-width modulation through fuzzy logic control, a proportional-integral-differentiation algorithm, or any other suitable means. Temperature control can be provided to a resolution of 1° C., or any other suitable resolution given the application.

The heater 192 functions to modulate the temperature of the array of wells 120 at the substrate 110, but can additionally or alternatively include any suitable temperature control mechanism (e.g., an electrothermal cooling plate). In variations, the heater can include a low-mass heater that interfaces with substrate 110 for thermocycling or incubation (e.g., of PCR components, reagents, and/or sample), and in a specific example, the heater can comprise an aluminum heater coupled to a resistive power resistor (7 ohms) and a 2-wire 100-ohm RTD, wherein the the heater elements are connected to an in-house heater driver and temperature controller. A PWM signal of 12 volts is provided across the heating element to heat the aluminum heater. The RTD provides temperature sensing and a control algorithm is used to modulate the temperature. During cooling, heating is stopped and a fan is turned on to remove heat. Because the thermal mass is small, heating between anneal temperature (~60° C.) and denaturation (~94° C.) can be achieved in 20 seconds and cooling from 94° C. to 60° C. can be achieved in 40 seconds with the specific example. In another specific example, the thermal control module can be used to maintain the temperature of the array of wells below 10° C. (e.g., 5° C.) in order to preserve the viability of mRNA extracted from captured cells.

The heater is preferably a resistive electrothermal heating element, but can alternatively or additionally include an induction heating element, convective heating element, optical heating element, or any other suitable heating mechanism. Preferably, the heater is preferably arranged adjacent to a bottom surface of the substrate, wherein the lateral broad face of the heating element is directly coupled to the lower broad face 114 of the substrate beneath the array of wells, but can alternatively be positioned adjacent to a top surface of the substrate 112, distal the substrate (e.g., in variations wherein the heater includes non-contact heating mechanisms) at either the bottom or top surface of the substrate, or in any other suitable location relative to the substrate.

In a first variation, the heater 170 comprises a heat-conductive substrate coupled to a heating element. In the first variation, the heat-conductive substrate preferably houses the heating element; however, the heating element can alternatively be configured to contact a surface of the heat-conductive substrate. The heat-conductive substrate can be composed of a conductive material (e.g., silicon, aluminum, copper, gold, silver), or any other suitable material for transferring heat from the heating element. Preferably, the heat-conductive substrate maintains temperature uniformity over a heating surface with less than 1° C. variability over the heating surface; however, the heat-conductive substrate can provide any suitable temperature profile over a heating surface. In the first variation, the heat-conductive substrate preferably has a thin profile (e.g., has a dimension less than 4 mm thick), to reduce the energy required to heat the heat-conductive substrate to a specified temperature. The heat-conductive substrate can be further configured to provide cooling. In a specific example of the first variation, less than 50 (e.g., 40, 30, 20, 10) Watts of power is required to heat the heat-conductive substrate to a temperature of 100° C. from room temperature within an appropriate amount of time.

In an example of the first variation, heating through one face can be accomplished by using a plate-shaped resistance heater that has one exposed face and thermal insulation covering all other faces. In another example of the second variation, heating can be provided through one face of a heater by using a Peltier heater. In a variation of the heater 192 using a Peltier heater, the heater 192 comprises a thermoelectric material, and produces different temperatures on opposite faces of the heater 192 in response to a voltage difference placed across the thermoelectric material. Thus, when a current flows through the Peltier heater, one face of the Peltier heater lowers in temperature, and another face of the Peltier heater increases in temperature. The system 100, however, can further comprise any other suitable heater 170 configured to heat a biological sample and/or a fluid.

Figure 15A:
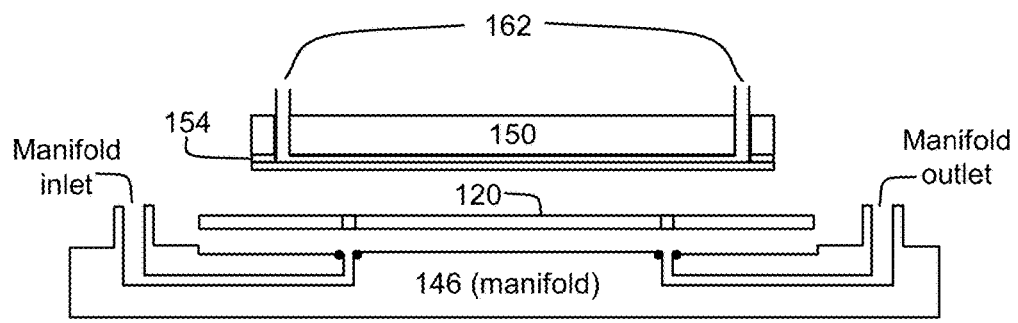
FIGS. 15A-15B depict cross-sectional views of a variation of a portion of a portion of a system for isolating and analyzing cells.
Figure 15B:
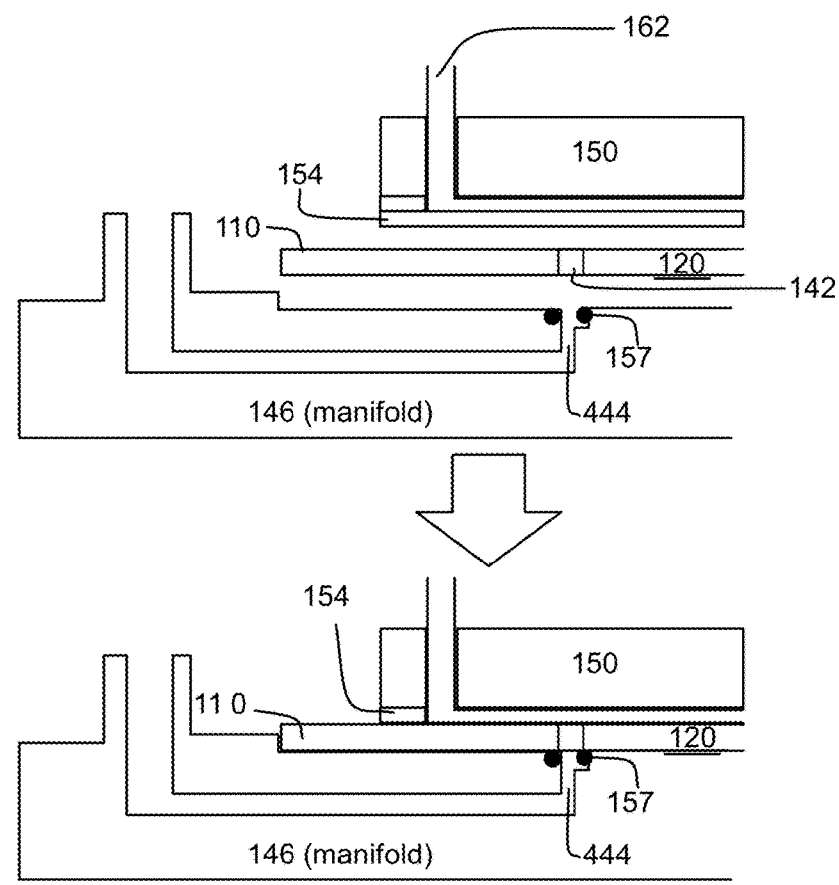

The thermal control module can also include a second heating element additionally and/or alternatively to the heater 192 described above, that functions to modulate and control the temperature of fluids provided to the array of wells during reagent delivery. As shown in FIGS. 15A and 15B, a fluid heater 154 (e.g., an aluminum heater with a defined geometry) can be coupled within the recess 152 of the fluid delivery module 140. The fluid heating plate 154 is preferably coupled to a plate (e.g., the first plate 150 of the fluid delivery module 140), wherein the first plate 150 is configured to facilitate coupling of the set of fluid pathways 146 (e.g., via the manifold) to the array of wells. In one variation, the fluid heater 154 is coupled to a surface of the first plate 150, and in another variation, the fluid heater 154 is embedded within the first plate 150. The plate 150 is preferably configured to facilitate heat transfer between the fluid heater 154 and the fluid within the fluid reservoir coupled to the array of wells, such that a biological sample and/or a fluid within the array of wells can be appropriately heated. The plate 150 can be further configured to provide conductive cooling through a fluid path 162; however, cooling may not be provided, or can be provided using any other suitable element (e.g., a fan blower coupled to provide forced air cooling as necessary). In variations wherein the plate 150 is configured to provide cooling, cooling can be enabled by flowing a coolant (e.g., water, oil, air, composite liquid) through a fluid path 162, and controlled using a controlled fluid pump.

Figure 16:
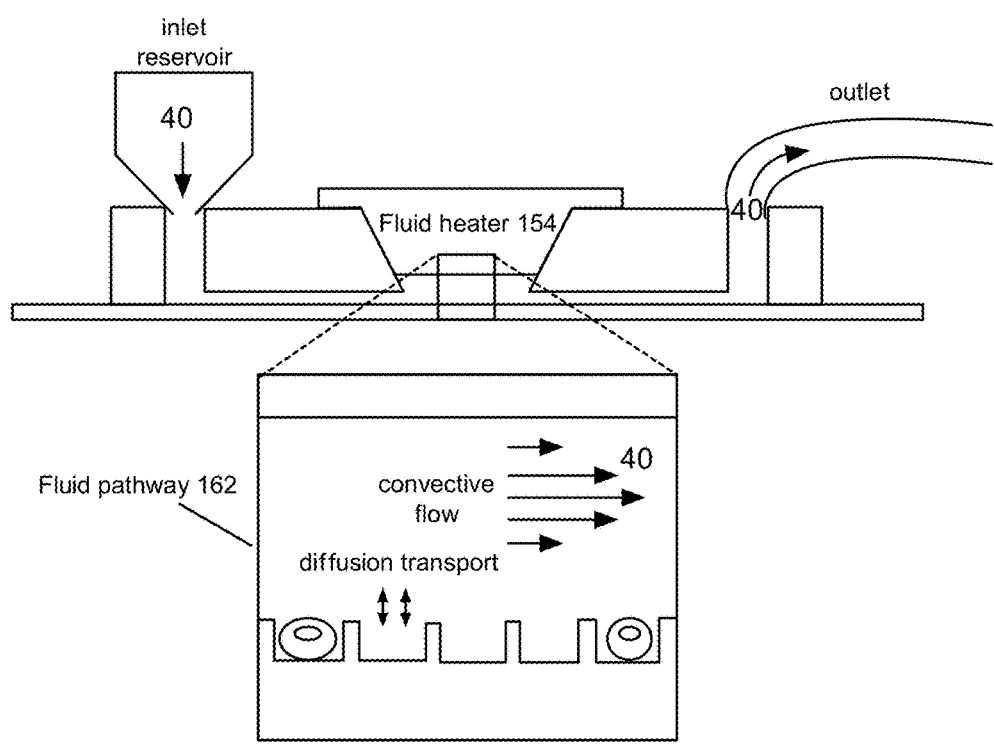
FIG. 16 depicts a variation of a system for isolating and analyzing cells.

As such, a variation of the system 100 as shown in FIG. 16 can further comprise a fluid heater 154 coupled to the first plate of the fluid delivery module within the recessed region, the fluid heater 154 at least partially defining the fluid layer through which a convective flow provided by the fluid heater 154 can flow in the second direction parallel to the broad surface, wherein, with the fluid heater 154, the system is operable in a diffusion mode that provides diffusion transport between the convective flow and the set of wells. In more detail, the open surfaces of the set of wells are very small compared to the region of the reservoir where convective reagent flow through the fluid path is established. Reagents can be transported from the fluid layer into the set of wells by diffusive transport. The time required for diffusion of a reagent into a well (approximately 30-50 microns deep) can be estimated using the formula, Diffusion Time~(Diffusion Length)$^2$/Diffusivity, and the timing, velocity, and temperature at which multiple and/or consecutive reagents are dispensed to the array of wells can be appropriately adjusted and/or optionally automated to account for proper uniform exposure of the contents of the wells to the reagents during various biochemical assays. For example, a small molecule, such as PCR primer (Diffusivity $10^{-6}$ cm$^2$/s) would take approximately 9 seconds to diffuse into the well. Taq Polymerase with diffusivity of approx. $4.7 \times 10^{-7}$ cm$^2$/s would need about 19 seconds to diffuse across the well cavity. Thus, in order to deliver "all-in-one" (e.g., sequential, simultaneous, single, multiple, mixtures of reagents) PCR reagents into the array of wells, reagents are convectively transported into the fluid reservoir given the provision of sufficient time (around 2-3 minutes) for the reagents to diffuse into the array of wells. In variations, for a well containing a cell-particle pair with a well cavity height of approximately 40 microns, the presence of an impermeable non-cell particle on top of a cell can obstruct the diffusive fluid path between the fluid path 162 within the fluid reservoir 160 and the well cavities below, thereby requiring at least two (e.g., three, four, five, ten) times more diffusion time for reagents to arrive at the captured cell than for wells containing only a single cell.

1.5 System—Imaging Subsystem 194

The system 100 can additionally include an imaging subsystem 194 that functions to image the contents of the set of wells, and can further function to distinguish target objects (e.g., CTCs, labeled cells, microspheres) captured in the set of wells from other cells or objects in the sample introduced into the system 100. The imaging subsystem 194 preferably includes a fluorescence microscope, but can additionally or alternatively include any suitable imaging mechanism (e.g., an optical microscope, a CCD camera, a photodiode array, a light emitting diode, reflectors, one or more processors etc.). The fluorescence microscope is preferably operable (e.g., in an identification mode, a detection mode, etc.) to detect a fluorescence signal emitted from a target object one or more of the set of wells, and thereby identify that the well(s) contain(s) a target object. In a specific example, the imaging system (e.g., fluorescence imaging system) can be operable in a mode for providing real-time or near real-time fluorescence imaging of samples processed according to an assay. The imaging subsystem 194 is preferably positioned beneath the substrate and oriented to image the contents of the set of wells through the transparent (or translucent) material of the substrate; alternatively, the imaging subsystem 194 can be positioned above the substrate and oriented to image the contents of the set of wells unobstructed by the material of the substrate itself. However, the imaging subsystem 194 can be otherwise positioned in any suitable manner.

Additionally or alternatively, the system 100 can include any other suitable element that facilitates cell processing and/or analysis. For instance, the system 100 can include optical elements (e.g., embedded within the substrate 110, coupled to the substrate 110) that function to facilitate imaging. The optical elements function to adjust incoming light, preferably to facilitate imaging. The optical elements can function to bend, reflect, collimate, focus, reject, or otherwise adjust the incoming light. The optical elements are preferably defined within the substrate 110, but can alternatively be defined by any other suitable component of the system 100. Optical elements can include any one or more of: light reflectors disposed within the substrate thickness adjacent the array(s) 110 defined on a surface of the substrate 110 opposite that defining the array of wells 120, microlenses defined on a broad surface of the substrate 110 proximal that defining the array of wells 120, light collimators, light polarizers, interference filters, light reflectors (e.g., 90° illumination elements), elements that minimize excitation rays from going into path of collected fluorescence emission light, diffraction filters, light diffusers, and any other suitable optical element. The system 100 can additionally or alternatively include well affinity mechanisms that function to attract a cell of interest 10 towards a well 128. Well affinity mechanisms can include electric field traps, affinity moieties (e.g., coated to a well surface), features (e.g., microfluidic features) that direct flow into an element, or any other suitable pore affinity mechanism. The system 100 can, however, include any other suitable element(s).

Figure 17:
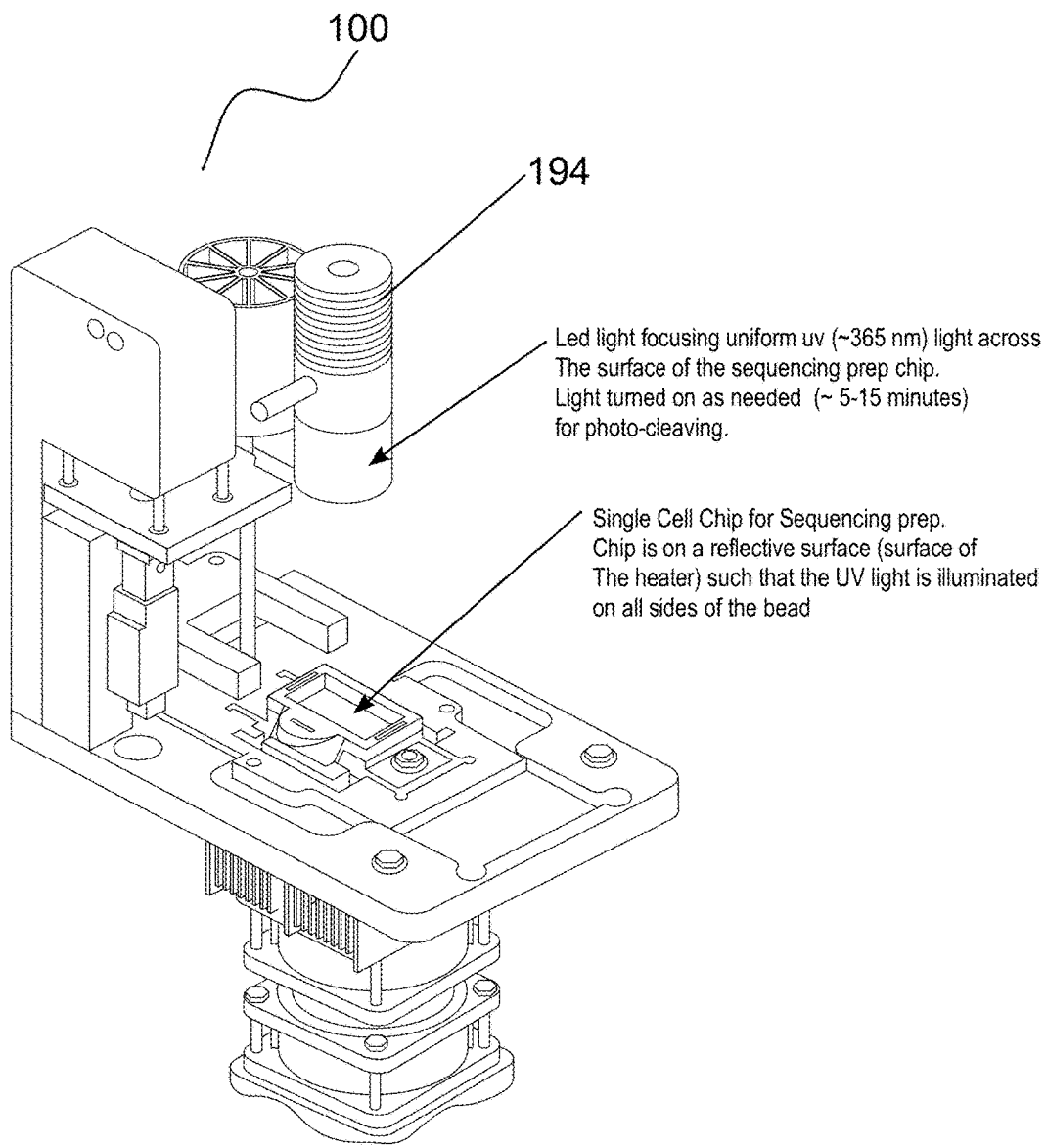
FIG. 17 depicts a variation of a portion of a system for isolating and analyzing cells.

In a variation, as shown in FIG. 17, the imaging subsystem 194 can include an ultraviolet illumination element that functions to sterilize wells, and additionally or alternatively to irradiate wells containing light-reactive components, such as photo-cleavable chemical bonds. The ultraviolet illumination element can include one or more light emitting diodes, mercury vapour lamps, and/or metal halide lamps, that emit wavelengths between 300 to 400 nm. In a specific application, as described in Section 2.4, UV illumination at ~365 nm wavelength can be performed for 5 to 20 minutes at the array of wells to separate a set of probes 36 from a particle, by cleaving a photo-sensitive bond coupling the set of probes 36 to the particle (e.g., biotinylated chemistry). In some variations, wherein the illumination element is positioned superior the array of wells, the heating element of the thermal control module below the array of wells can include a reflective surface that can enhance the uniform illumination of the particles within each well in the array of wells. However, photo-illumination of the contents of the array of wells can be performed in any suitable manner, and by any configuration not the illumination element. Furthermore, the imaging subsystem and/or any other component of system 100 can also include reflective surfaces positioned at different locations in relation to the array of wells, in order to uniformly illuminate the interior of each well cavity. In one example further described in Section 2, the heating surface of the thermal control module 190 below the substrate can be reflective, thus permitting UV light to illuminate all surfaces of the captured particles for photocleaving molecules (e.g., set of probes, genetic complexes) from the outer surfaces of the particles and/or the interior surfaces of the well cavities. However, incident light from the imaging subsystem into the array of wells can be modified, reflected, refracted, diffused, and/or otherwise manipulated by any other feature of any other component in system 100 to improve optical interrogation of the contents of each well.

The imaging subsystem 194 can also further comprise a tag identifying system comprising a detection module and at least one tag configured to provide information. The tag identifying system functions to read barcodes, QR codes and/or any other identifying tags of the system 100, and to communicate information from the identifying tags to a processor. The tag identifying system can be coupled to the illumination module 110, to facilitate identification and reading of tags located on imaging substrates coupled to the platform, or any other suitable system element. In other variations, the tag identifying system may not be coupled to the illumination module. The tag identifying system is preferably fixed in location, but can alternatively be configured to move relative to other system elements. In one alternative variation, the tag identifying system can be a standalone unit that is configured to be manipulated by a user to scan tags or labels located on elements of the system 100. The tag identifying system can comprise a barcode reader, a radio-frequency identification (RFID) reader, a QR code reader, a nearfield communication device, or any other suitable element implementing a mechanism that can identify a unique identifier located on the an imaging substrate or other aspect of the system 100 (e.g., glass slide, cartridge, array of wells, etc.). The tag identifying system can alternatively or additionally be configured to parse and interpret non-encoded information (e.g., text) on an identifying tag. In some variations of the system 100, the optical sensor of the imaging subsystem 194 can additionally function as a tag identifying system.

Preferably, a tag intended to be identified and/or read by the tag identifying system preferably communicates information to the tag identifying system upon being read. The information can comprise information related to imaging substrate (e.g., array of wells, glass slide) identification information, protocol information (e.g., staining protocol information), information related to suggested system parameters required to actualize a protocol, information related to calibration of the system 100 with regard to a specific imaging substrate, information related to contents of an imaging substrate, information configured to facilitate positive location identification of an imaging substrate or locations within an imaging substrate, and/or any other suitable type of information. The information can be coupled to (e.g., embedded within) image data captured by the optical sensor, and/or can be communicated to the processor using any other suitable means.

1.6 System—Additional Elements

In embodiments of the system 100 configured to promote further purification of captured cells, the system 100 can further comprise a magnet 90 that enables separation of captured cells from undesired sample materials. The magnet 90 is preferably a single magnet, but can alternatively be one of multiple magnets (e.g., lined up in parallel), in order to provide a greater magnetic flux to capture magnetically-bound particles. Preferably, the magnet or group of magnets 90 is coupled to a magnet holder of the system 100, wherein the magnet holder is configured stabilize the position of the magnet(s) of the system 100 to provide experimental consistency. Additionally, the magnet 90 is preferably configured to be positioned proximal to the fluid reservoir 160, such that purification of captured cells is facilitated within the fluid reservoir 160 by a magnetic field provided by the magnet; however, in alternative variations, the magnet can be unfixed or fixed relative to any suitable element of the system. In an example, the magnet 90 is a rectangular prism-shaped magnet 90 fixed to the manifold (e.g., set of fluid pathways 146) proximal to the fluid reservoir 160 and contacting a wall of the fluid reservoir 160, such that particles of a sample bound to magnetic beads can be reversibly captured at a wall within the fluid reservoir 160. In another example, the magnet can be configured to provide a magnetic field at the manifold, at the array of wells 180, or at an outlet fluid reservoir 160, such that magnetically-bound particles can be captured within at least one of the manifold, the array of wells 180, and the outlet fluid reservoir 160 during processing and/or purification.

The system 100 can further include an extraction module (e.g., cell retrieval subsystem) that functions to extract at least one of a single cell and a cell cluster from a well 128 of the array. While an individual cell from a single well 128 is preferably selectively removed, the extraction module can facilitate simultaneous multiple cell/cell cluster removal from the array of wells 120. The cell/cell cluster is preferably removed by applying a removal force to the cell. The removal force is preferably applied by aspirating the contents out of a well 128 (i.e., using a negative pressure); however, the removal force can additionally or alternatively be applied by pumping fluid through the array of wells 120 (e.g., by way of a perimeter channel 150) to provide a positive pressure that drives the cell/cell cluster from the well 128. In one variation, the pump pressure provided by a pump mechanism at the extraction module is less than 10,000 Pa, and in a specific variation, the provided pump pressure is 6,000 Pa. In another specific variation, the provided pump pressure is 1,000 Pa. However, any other suitable pump or aspiration pressure can be used.

In some variations, the extraction module can comprise a particle extractor. The particle extractor functions to selectively remove one or more isolated cells and/or non-cell particles from an addressable location within the system 100. The particle extractor is preferably configured to remove a cell/particle cluster from a single well 128, but can alternatively be configured to simultaneously remove multiple cells/particle clusters from multiple wells. The extraction module is preferably operable in an extraction mode, wherein in the extraction mode the extraction module extracts at least one of a set of single cells and a set of non-cell particles from a well of the set of wells, along a direction normal to the base surface of the well. In the extraction mode, the fluid delivery module is preferably removed from the substrate; however, the fluid delivery module can alternatively remain coupled to the substrate when the cell removal module is operated in the extraction mode. The particle extractor can, however, comprise any other suitable cell removal tool such as that described in U.S. application Ser. No. 13/557,510, entitled "Cell Capture System and Method of Use" and filed on 25 Jul. 2012, which is herein incorporated in its entirety by this reference.

In a first variation of the particle extractor, the particle extractor is configured to access the array of wells 120 from a direction normal to the upper broad surface 112 of the substrate 110. The particle extractor preferably removes the cell/particle cluster in a substantially normal direction from the upper broad surface 112 of the substrate 110, but can alternatively remove the cell/particle cluster in an angled direction relative to the upper broad surface 112 of the substrate 110. The particle extractor preferably includes a hollow channel (e.g., of a micropipette, capillary tube, etc.) that accesses the array of wells 120 and defines a substantially fluidly isolated volume in fluid communication with one or more wells. The hollow channel can include one or more sealing elements at the tip (e.g., a polymeric coating or adequate geometry) that facilitate fluid seal formation with the well(s). The particle extractor preferably tapers from a proximal end to the tip, in order to provide an adequate geometry to receive contents of a well into the particle extractor; however, the particle extractor can alternatively have any other suitable form. As such, the hollow needle is preferably configured to form a substantially fluidly isolated volume within a well 128 of interest, and a low-pressure generator (e.g., a pump) is then used to aspirate the retained cell/cell cluster out of the well 128, through the hollow channel, and into a cell collection volume of the particle extractor. In one variation, the particle extractor is a micropipette having a height of 200 micrometers and a hollow channel diameter of 25 micrometers; in another variation, the particle extractor is a capillary tube having a channel diameter of 150 micrometers. In another variation, the wells of the array of wells 120 are grouped such that each group may be circumscribed by a closed curve in the plane parallel to the broad surface of the substrate, and the particle extractor has an inner diameter that is smaller than the largest chord of the closed curve. However, other variations of these specific examples can have any other suitable defining dimensions.

Cell and/or non-cell particle removal from the system 100 is preferably automated, but can additionally or alternatively be semi-automated or manual. Furthermore, cell and/or non-cell particle removal can be performed along with cell identification, comprising automatic fixing, permeabilzation, staining, imaging, and identification of the cells removed from the array of wells 120 through image analysis (e.g., through visual processing with a processor, by using a light detector, etc.) or in any other suitable manner. The extraction module can be configured to facilitate advancement of a particle extractor to a well 128 containing a cell/particle cluster of interest, for instance, with an actuation subsystem. The extraction module can additionally or alternatively be configured to facilitate cell and/or particle removal method selection and/or cell removal tool selection. In another variation, cell identification at the extraction module can be semi-automated, and cell and/or particle retrieval can be automated. For example, cell staining and imaging can be done automatically, wherein identification and selection of the cells of interest can be done manually. In another variation, all steps can be performed manually. However, any combination of automated or manual steps can be used.

Variations of the system 100 can be operable to facilitate assays in a manner analogous to the methods described in U.S. application Ser. No. 15/333,420 entitled "Cell Capture System and Method of Use" and filed 25 Oct. 2016, U.S. application Ser. No. 14/163,185 entitled "System and Method for Capturing and Analyzing Cells" and filed 24 Jan. 2014, U.S. application Ser. No. 14/863,191 entitled "System and Method for Capturing and Analyzing Cells" and filed 23 Sep. 2015, and U.S. application Ser. No. 14/289,155 entitled "System and Method for Isolating and Analyzing Cells" and filed 28 May 2014, which are each incorporated in their entirety by this reference. The system is additionally or alternatively operable for a variety of on-chip (e.g., in situ at the substrate) analyses and assays, including: on-chip immunochemistry, on-chip DNA and/or mRNA FISH, on-chip mRNA and/or DNA PCR, on-chip isothermal amplification, on-chip live cell assays, on-chip cell culture, and other similar assays.

In a specific example, the system may be operated according to the following procedure: a 4 milliliter whole blood sample is partially fixed with an equal volume of 0.4% PFA for 10 minutes; the sample is enriched for cancer cells and washed with PBS; the cells, comprising approximately 85% cancer cells and approximately 20,000 whole blood cells are backflowed with 1 milliliter PBS to generate a backflow solution containing the cells; the backflow solution is flowed over the array of wells 120 of the system 100 and the cells are captured by the wells; an immunostaining reagent is flowed by way of the fluid delivery module to each of the wells of the set of wells; cancer cells are identified using a fluorescence microscope which detects a fluorescence signal emitted by any cells which are successfully tagged by the immunostaining reagent; identified cells are extracted from their corresponding wells using the cell removal module of the system (e.g., a capillary tube on a three-axis traversing stage) and transferred to a PCR tube, where the single cell genome is amplified; the amplified single cell genome is packed for downstream processing (e.g., whole genome sequencing, targeted sequencing, etc.).

Additionally, as a person skilled in the field of cell sorting will recognize from the previous detailed description and from the figures and claims, modifications and changes can be made to the embodiments, variations, examples, and specific applications of the system 100 described above without departing from the scope of the system 100.

2. Method

Figure 18:
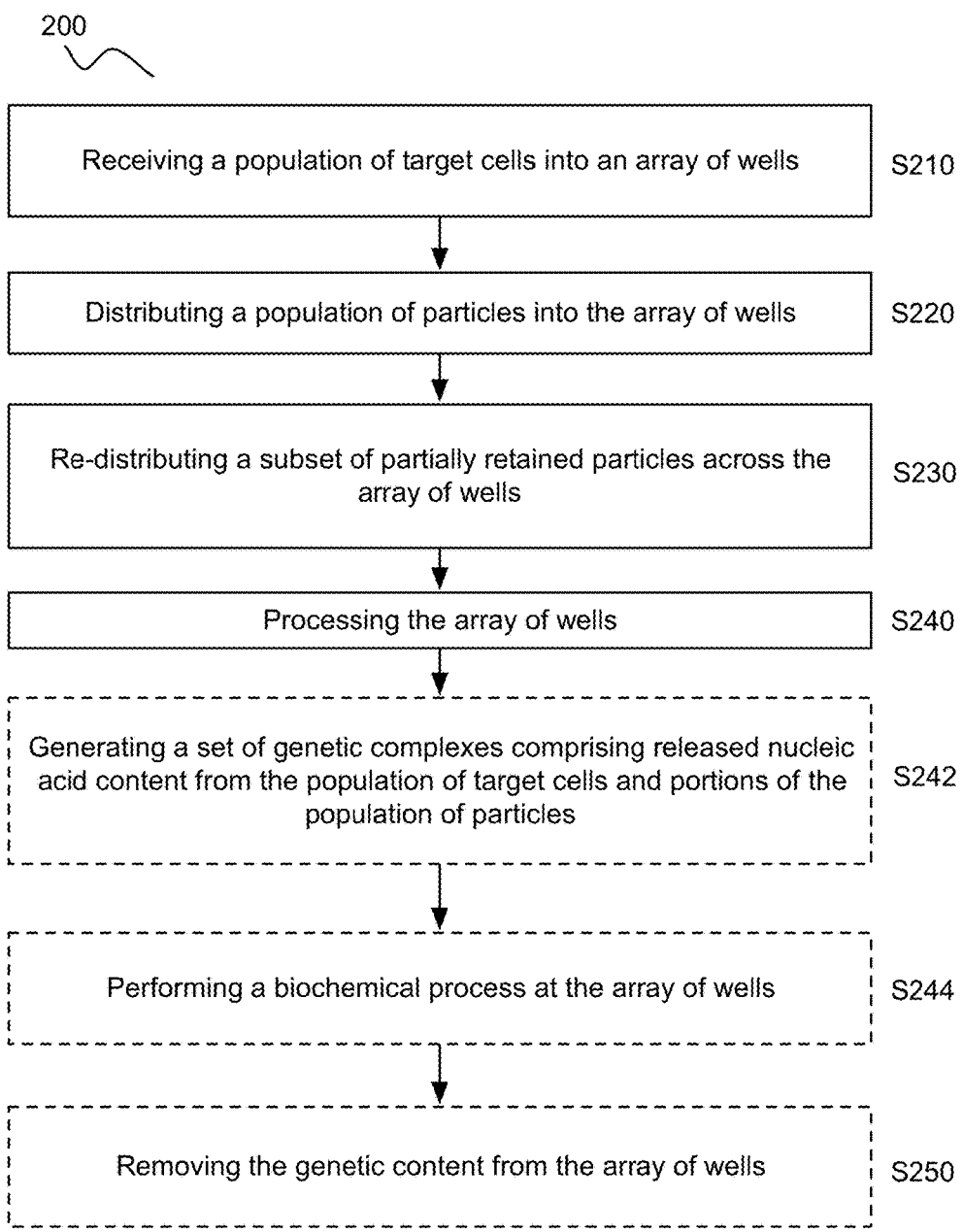
FIG. 18 depicts a flow chart for an embodiment of a method for isolating and analyzing cells.

As shown in FIG. 18, a method 200 for isolating and analyzing a population of target cells comprises: receiving a population of target cells into an array of wells in Block S210; distributing a population of particles into the array of wells in Block S220, wherein each particle of the population of particles can optionally be coupled to a set of probes 36 having a binding affinity for a biomolecule associated with the population of target cells; redistributing a subset of partially retained particles across the array of wells in Block S230; and processing the array of wells in Block S240. In some variations, Block S240 can include: generating a set of genetic complexes 70 comprising released nucleic acid content from the population of target cells and portions of the population of particles (e.g., the set of probes 36) in Block S242, and additionally or alternatively performing a biochemical process at the array of wells in Block S244. Furthermore, method 200 can additionally or alternatively include removing the set of genetic complexes 70 generated in Block S240 from the array of wells for downstream analysis in Block S250.

Figure 19:
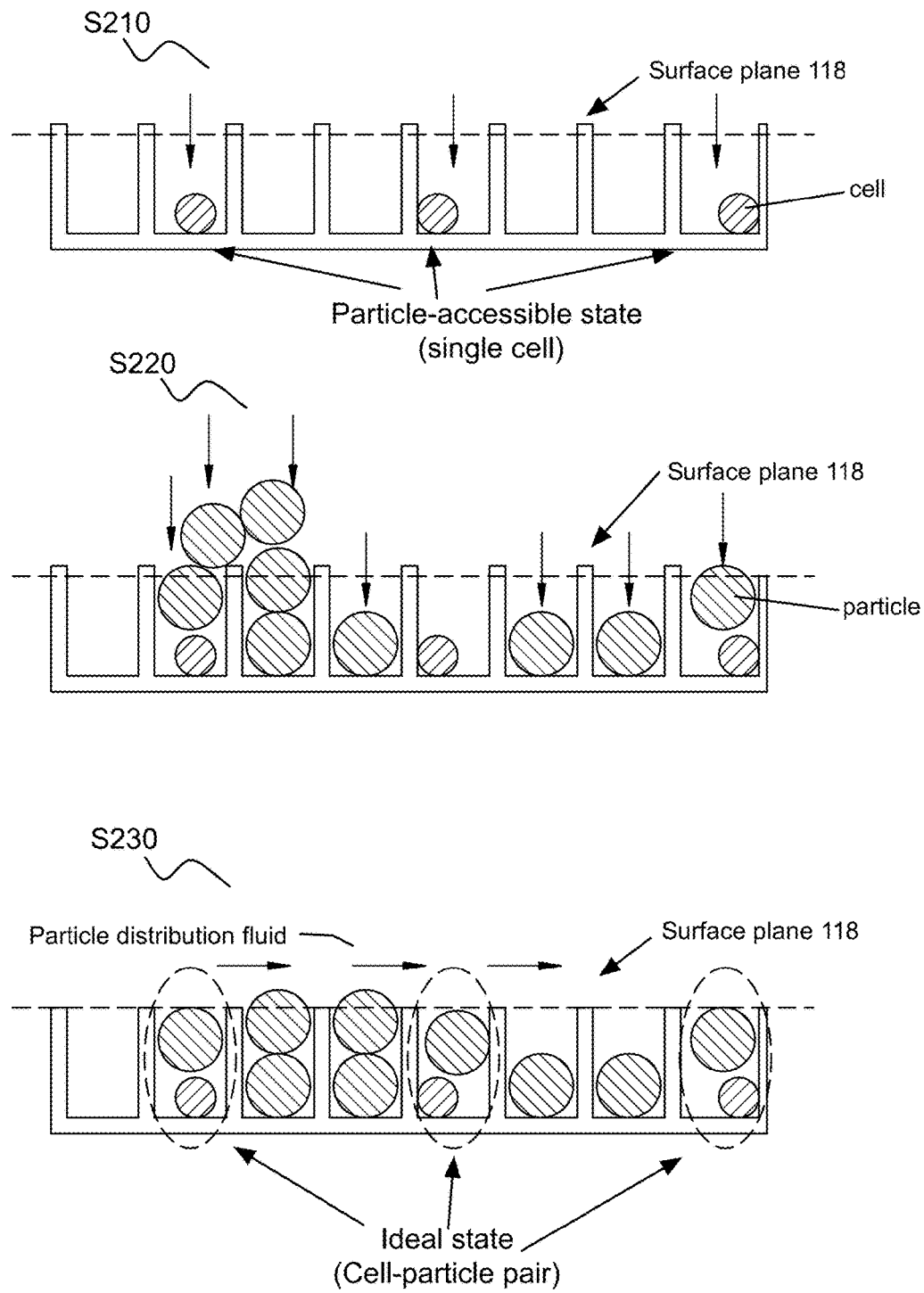
FIG. 19 depicts a schematic representation of a variation of an portion of a method for isolating and analyzing cells.

The method 200 functions to enable isolation, capture, and retention of cells, more preferably to enable efficient capture of cells in single-cell format and/or single-cluster format (e.g., a pair of a single cell and a single particle colocalized within the same well), at known, addressable locations, and further to facilitate performance of multiple single-cell/single cluster assays that can be performed on individual cells or cell clusters (e.g., rare cells in a biological sample, a cell-particle pair). In a preferred embodiment, as shown in FIG. 19, the method 200 functions to achieve an ideal state for a subset of the array of wells, wherein a well in the ideal state receives a single cell in Block S210, followed by a single particle in Block S220, in order to capture individual cell-particle pairs in single-cluster format within the array of wells. However in variations, the method 200 can achieve the ideal state for a subset of the array of wells that have received more than a single cell and/or particle, by redistributing the population of cells and/or particles that exceed the capacity of the well (e.g., traversing a spatial boundary defined by the surface plane 118 of the substrate), thereby correcting errors (e.g., aggregation, oversaturation) in the distribution steps in Block S210 and Block S230 to improve the efficiency of single-cell and/or single-cluster capture within the array of wells. In additional variations, the method 200 can redistribute the population of cells and/or particles that have not yet entered the array of wells as a result of previous distribution steps (e.g., remaining above the surface plane 118), thereby permitting uncaptured cells and/or particles additional opportunities to be received into accessible wells, and increasing capture efficiency of the introduced cell and/or particle populations. Specifically, through implementation of variations of the preferred embodiment, the steps of method 200 can increase the capture efficiency of single cell-particle pairs to greater than 80% capture efficiency, as compared to less than 20% capture efficiency by other methods. The steps of method 200 can be used to achieve the ideal state for a subset of the array of wells in any sequence or number of repetitions, and can additionally and/or alternatively be used to manipulate the contents of the array of wells to hold any number of cells, non-cell particles, and/or any combination thereof (e.g., combinations of one or more cells, one or more particles, etc.) in order to permit downstream analysis of the population of captured cells.

Figure 20:
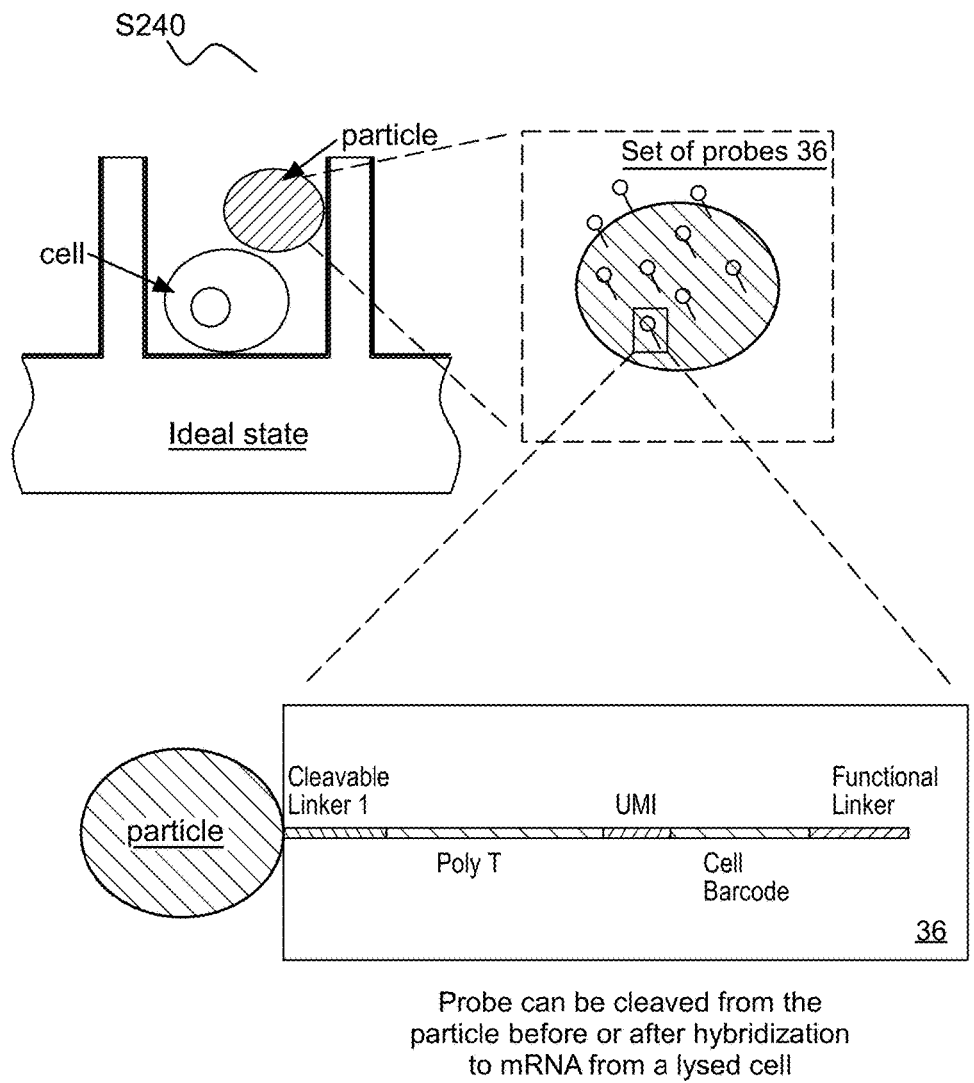
FIG. 20 depicts a schematic representation of a variation of a portion of an embodiment of a method for isolating and analyzing cells.

In a preferred application, method 200 can function to enable downstream processing of the array of wells for genetic analysis. In a variation, as shown in FIG. 20, a single cell-particle pair that has been captured within a well can be processed within the well to form an identifiable genetic sequence, wherein nucleic acid content of the cell can bind to a complementary nucleotide probe coupled to the particle. In this way, method 200 can provide significant benefit to increasing the number of cells that can be processed in a short amount of time by quickly isolating and retaining cell-particle pairs, and performing biochemical processes upon the cell-particle pairs without necessitating removal from the array of wells. In some embodiments, the method 200 can be used to capture and facilitate analyses of circulating tumor cells (CTCs) and subpopulations of CTCs, such as circulating stem cells (CSCs), but can additionally or alternatively be used to capture any other suitable cell of possible interest for processing and analysis. However, method 200 can be implemented in any other suitable manner for any other suitable application in which high-throughput cell/particle isolation or pairing is desired.

In variations of the method 200, Blocks S210, S220, and/or S230 can be performed with any suitable number of repetitions, according to protocols for processing the cell population according to different assays. Furthermore, Blocks S210, S220, S230, and S240 can be performed in any suitable order or simultaneously, according to protocols for processing the cell population according to different assays. In an alternative embodiment of method 200, distribution of particles in Block S220, and additionally or alternatively re-distribution in Block S230, can be performed prior to distribution of target cells in Block S210.

Figure 24:
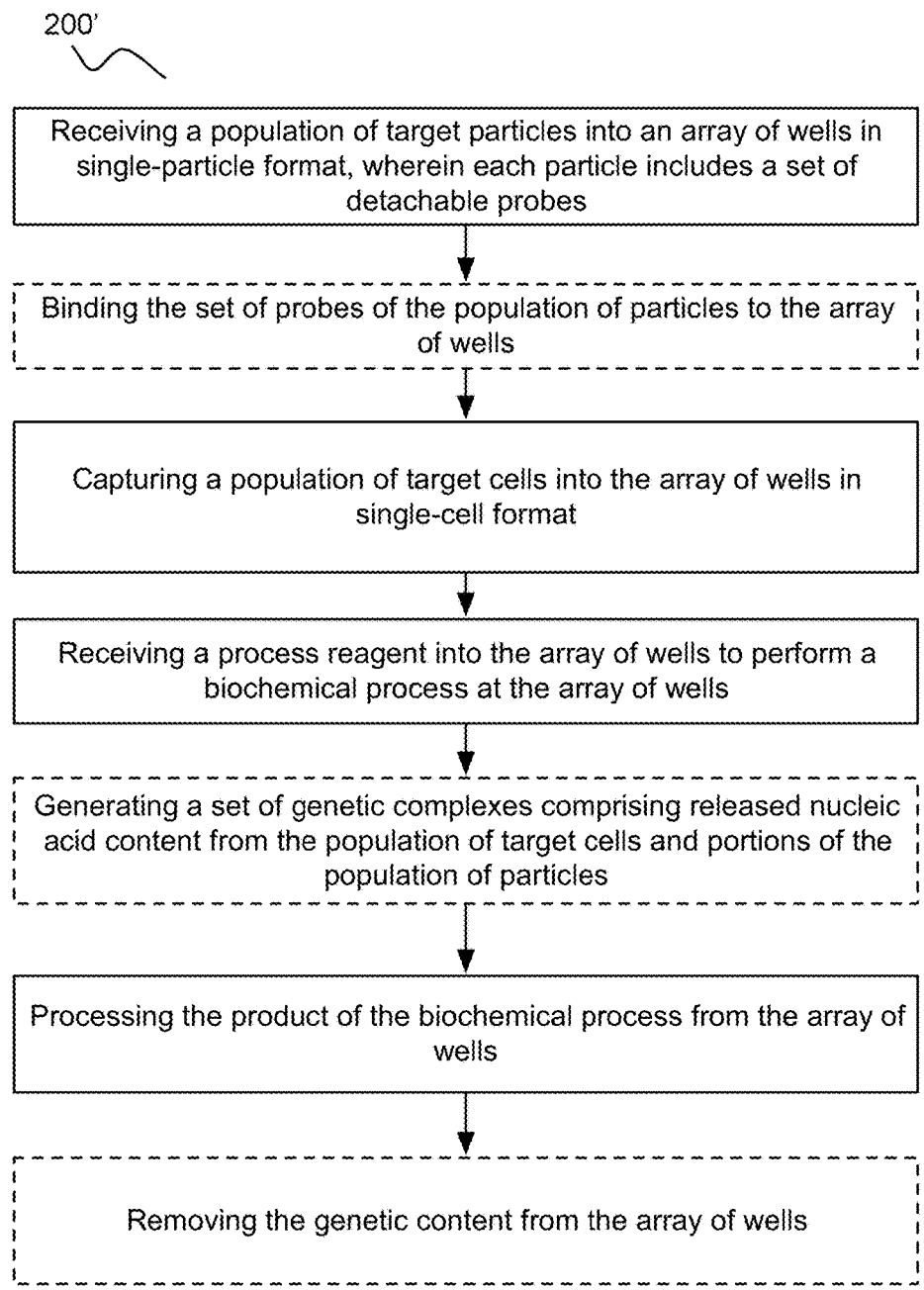
FIG. 24 depicts a flow chart for an embodiment of a method for isolating and analyzing cells.
Figure 25:
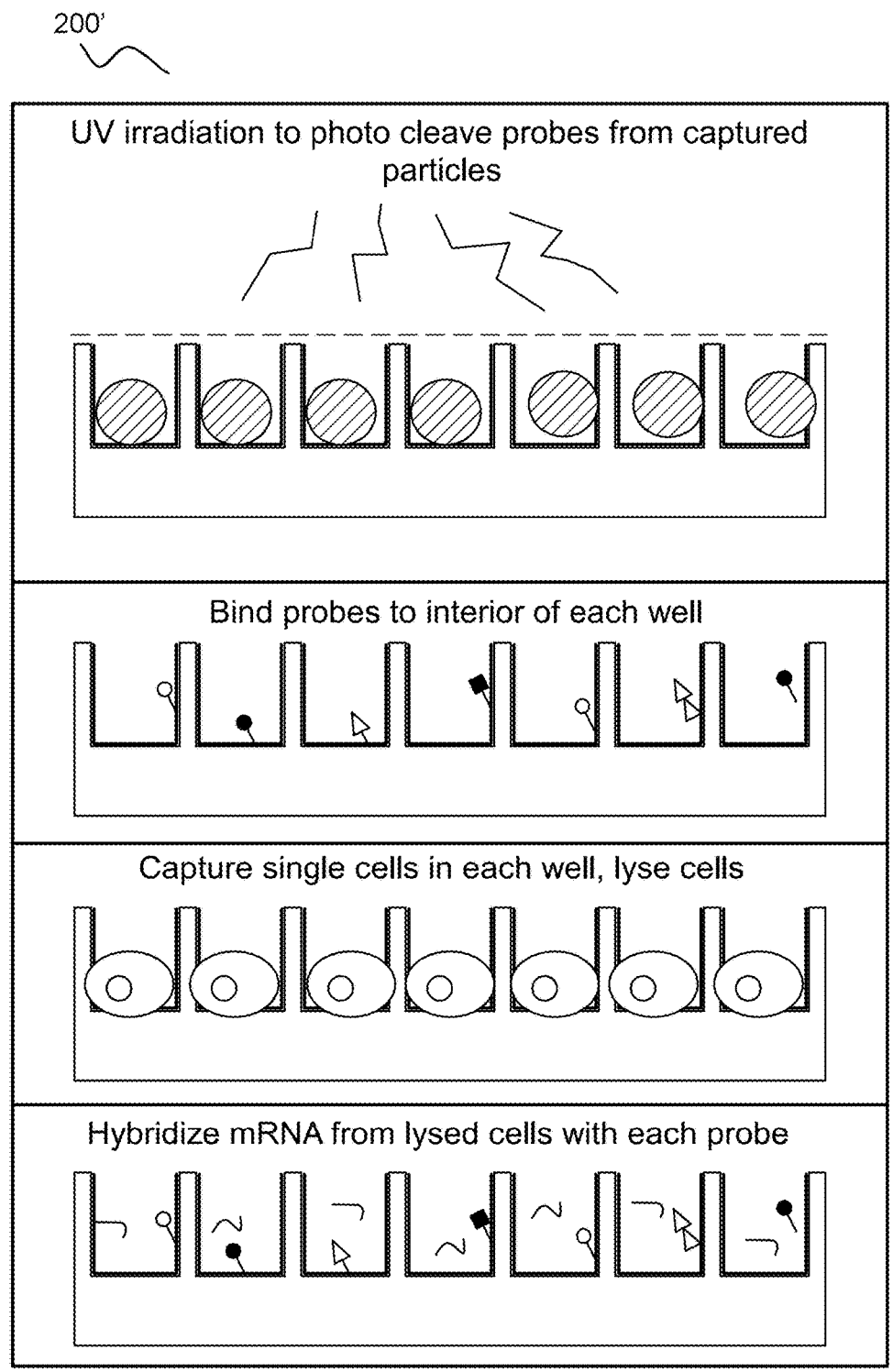
FIG. 25 depicts a schematic representation of a variation of a portion of an embodiment of a method for isolating and analyzing cells.
Figure 26:
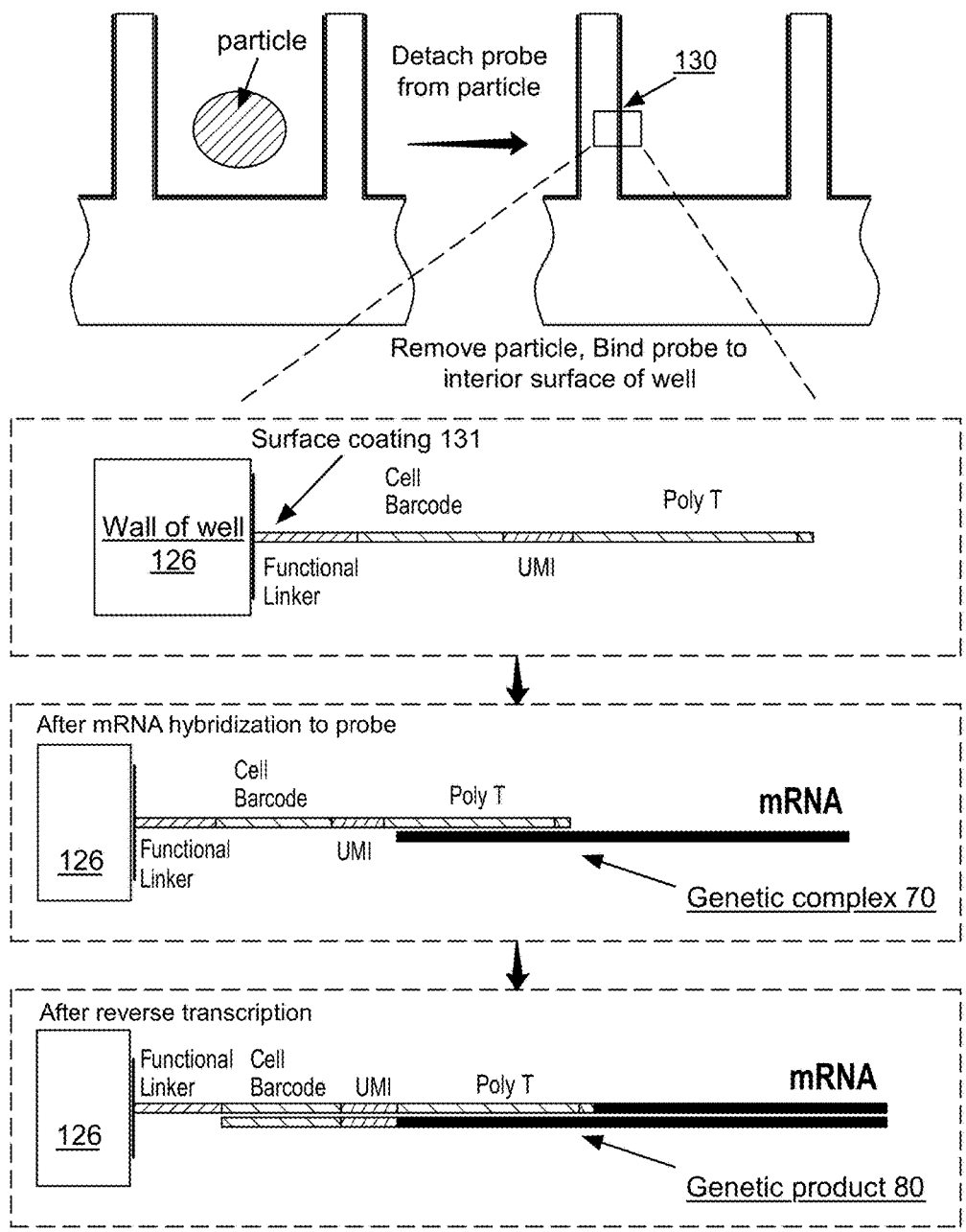
FIG. 26 depicts a schematic representation of a variation of a portion of an embodiment of a method for isolating and analyzing cells.
Figure 27:
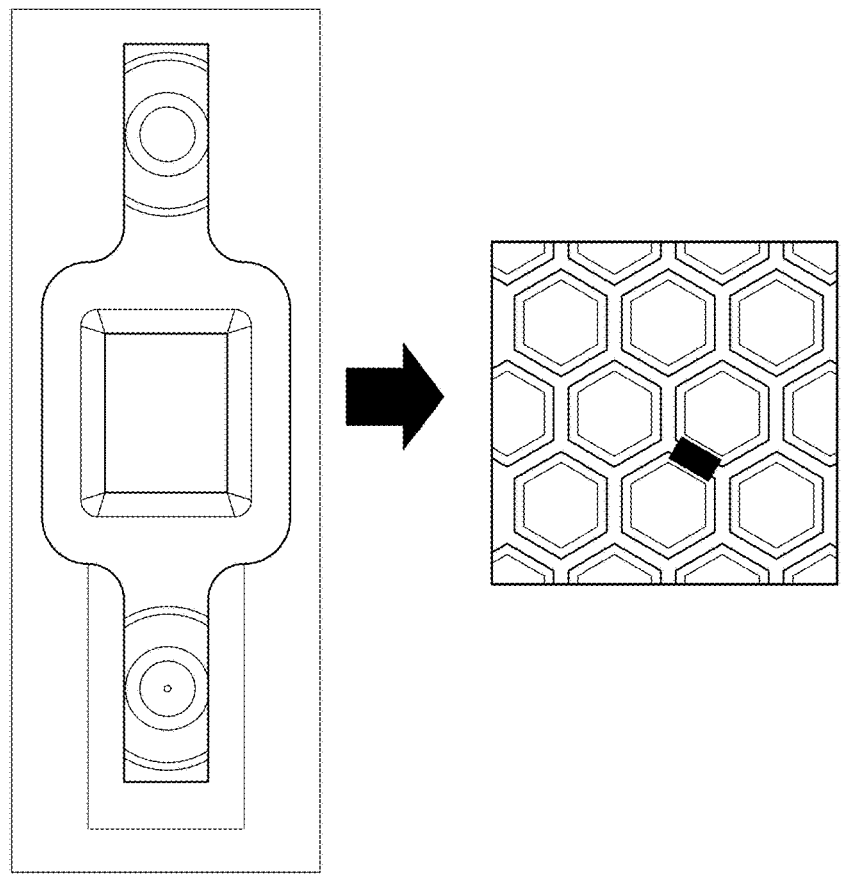
FIG. 27 depicts an example of an embodiment of a portion of a system and a method for isolating and analyzing cells.
Figures 28A, 28B:
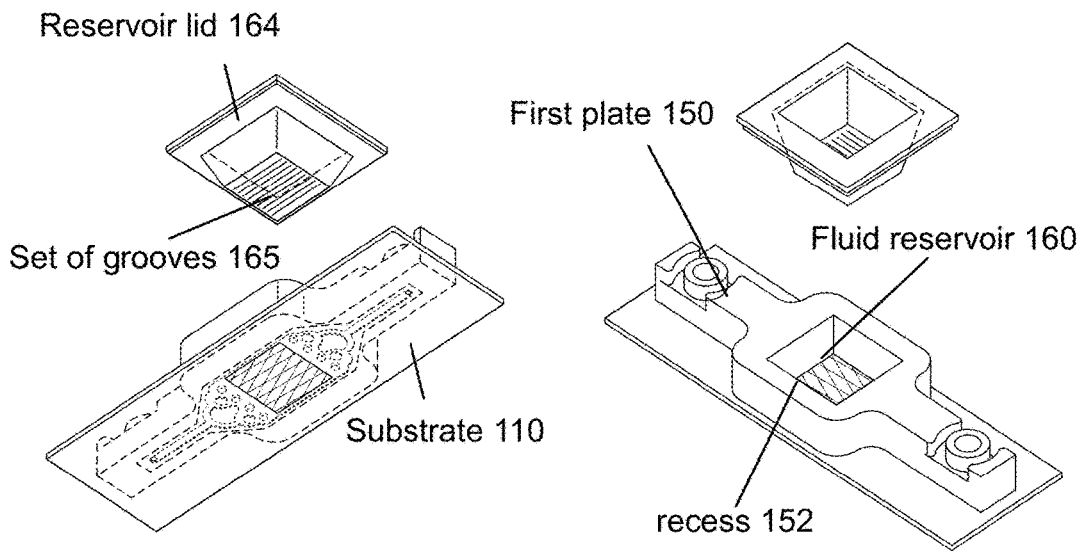
FIG. 28A-28C depicts an example of an embodiment of a portion of a system for isolating and analyzing cells.
Figure 28C:
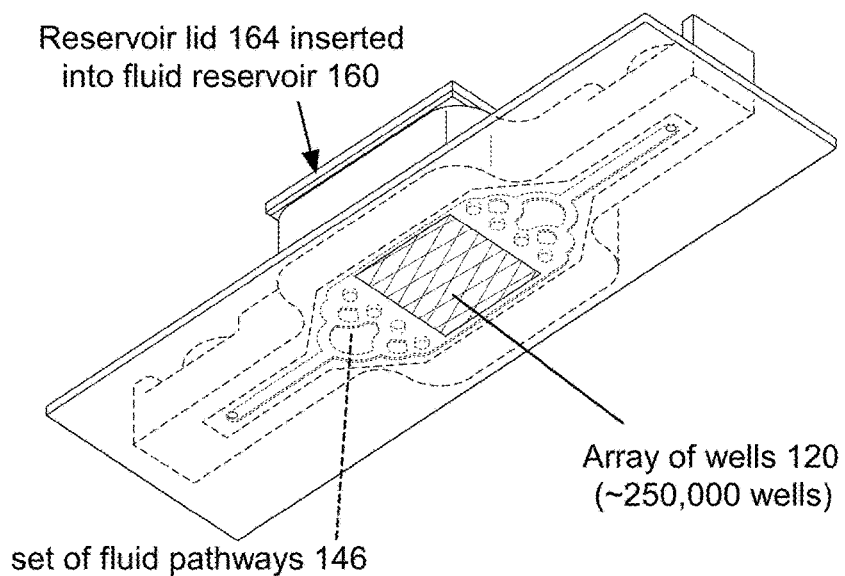
Figure 29:
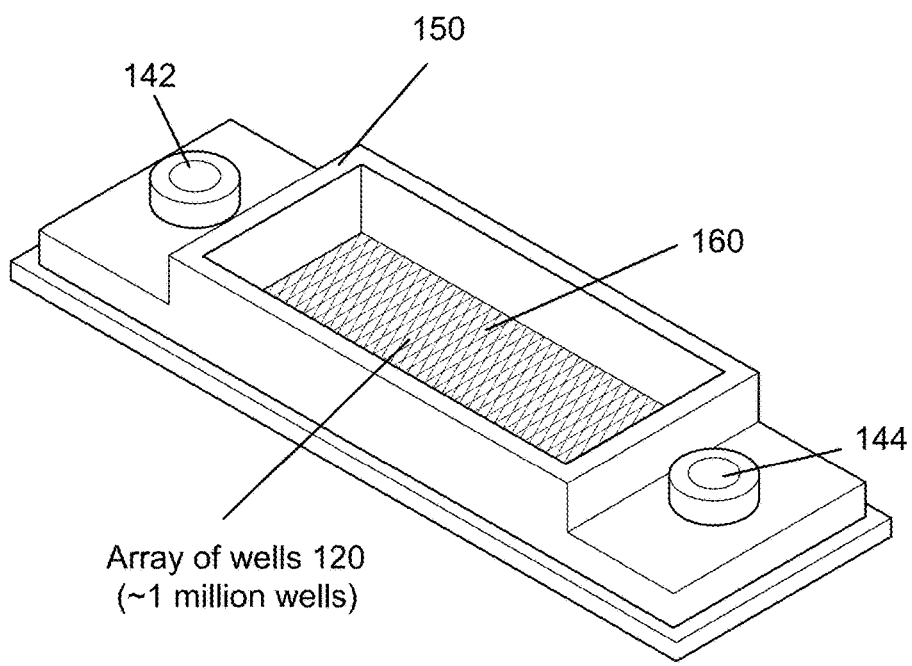
FIG. 29 depicts an example of a variation of a portion of a system for isolating and analyzing cells.

In a variation of this alternative embodiment of method 200, as shown in FIG. 24, FIG. 25, and FIG. 26, Block S220 can be performed prior to Block S210, which functions to enable single-particle capture of the population of particles within each well of the array of wells, wherein the population of particles can serve as delivery vehicles to deliver a set of labeled probes to each well. Preferably, each particle of the population of particles is detachably coupled to a probe or set of probes 36 comprising a unit identifier common to all probes in the set of probes 36 (FIG. 7). Once a single particle has been successfully captured into a well, the set of probes 36 may be released from the particle and can be bound to the interior surface of each well cavity. The particle can be optionally removed from the well, thereby enabling facile access of single cells to the array of wells for single-cell capture as described in Block S210. Once single cells have been captured within the wells, wherein each well contains a set of probes 36 unique to the individual well via the unit identifier of the set of probes 36, biomolecules, including genetic content, of the captured cells can be released and bound to the sets of probes to generate genetic complexes, as described in variations of Block S240 (FIGS. 24, 25 and 26). Removal, processing, and/or analysis of the genetic complexes can be performed in Block S250. As shown in FIG. 24 a method 200' for isolating and analyzing a population of target cells comprises: receiving a population of particles into an array of wells in single-particle format, wherein each particle includes a set of probes 36; capturing a population of target cells into an array of wells in single-cell format, wherein each cell can interact with a corresponding set of probes 36 within each well; receiving a process reagent into the array of wells to perform a biochemical process at the array of wells; and processing the product of the biochemical process from the array of wells. In some variations, method 200' can include: binding the set of probes 36 of the population of particles to the array of wells; generating a set of genetic complexes 70 comprising released nucleic acid content of each cell and the set of probes 36 within each well; processing the genetic complexes within the array of wells; and removing the set of genetic complexes 70 from the array of wells. The method 200' can function to enable the isolation, capture, and labeling of single cells for generating genetic libraries in single-cell format in a high-throughput manner, without necessitating the need for additional removal steps from the array of wells for downstream processing. By labeling each of the wells with a set of probes 36 comprising a unique label (particles captured in single-cell format), cells captured in single-cell format can be subsequently processed using the corresponding set of probes 36 localized within the same well. However, variations of steps of method 200 can be performed in any suitable order to isolate and label genetic material originating from single cells, and achieve generation of genetic complexes that can be easily identified, processed, and analyzed.

The method 200 is preferably implemented at least in part using the system 100 described in Section 1 above; however the method 200 can additionally or alternatively be implemented using any other suitable system 100 for cell capture and analysis. As described in a variation of Section 1 above, the well dimensions can be configured and selected to retain cells and/or particles below a surface plane 118 of the substrate (e.g., fully retained cells and particles), and egress cells and/or particles that traverse the surface plane 118 of the substrate (e.g., partially retained cells and particles). In such variations, any cells and/or particles that are not fully retained by their associated wells can be egressed in subsequent re-distribution steps as described in sections below. In a preferred variation, the well dimensions are selected to retain a single cell and a single particle as a cell-particle pair within the well cavity 128 and below the surface plane 118, however, the well dimensions can be configured to retain any number or combination of cells and non-cell particles, and can be utilized by method 200 in any other suitable way.

2.1 Method—Receiving the Population of Target Cells

Block S210 recites receiving a population of target cells into an array of wells. Block S210 functions to receive a biological sample including target cells of interest at an embodiment of the system 100 described in Section 1 above, and to facilitate distribution of the target cells into wells of the system 100 in at least one of single-cell format and single-cluster format. However, Block S210 can alternatively include receiving a biological sample at any other suitable system configured to capture cells in at least one of single-cell format and single-cluster format. In variations of Block S210, the biological sample can be received directly at a variation of the array (e.g., by pipetting, by fluid delivery through a fluid channel coupled to the array, etc.), by way of a variation of the first plate of a fluid delivery module (e.g., through a fluid reservoir 160 defined by a recess of the first plate, from a fluid channel embedded within the first plate and in fluid communication with the array, etc.), and/or in any other suitable manner. Furthermore, in variations of Block S210, the cell population can include a cell population of target cells (e.g., CTCs, CSCs, Immune cells) and/or any other suitable particle of interest.

Figure 21:
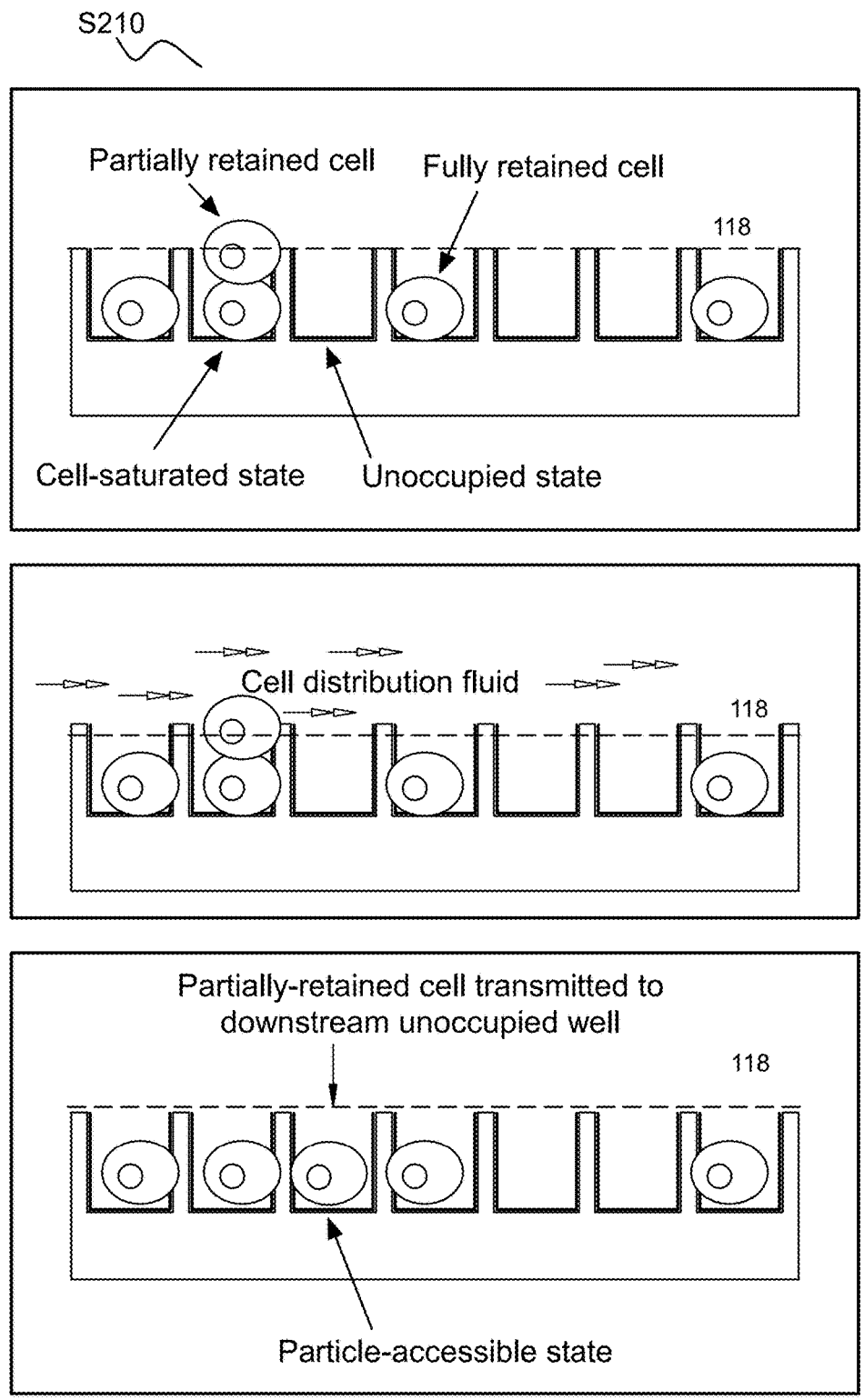
FIG. 21 depicts a schematic representation of a variation of a portion of an embodiment of a method for isolating and analyzing cells.

In variations of Block S210, as shown in FIG. 21, receiving the population of target cells can include distributing the population of target cells to the array of wells, and can optionally include re-distributing the population of target cells in one or more additional steps to correct for inaccuracies in the initial distribution step (e.g., when a subset of wells receives more or less cells than desired, when a subset of cells aggregates at a region of the substrate, etc.), which can improve the efficiency of capturing a desired quantity of target cells in each well. In a preferred embodiment, coordination of Block S210 with the size constraints of the well cavities of the array of wells can determine the number and shape of cells that can be captured and retained within the wells, as further described in Block S218 below. For example, a well with a height of 30 micrometers can receive one target cell with a characteristic diameter between 15-25 micrometers below the surface plane 118, and any additional target cells that enter the well beyond the first target cell traverse the surface plane 118, and exceed the boundaries defined by the height of the well cavity 128. Accordingly, any cells that are not fully retained by the well cavity 128 but instead traverse the surface plane 118 can be egressed from the well cavity 128 by a subsequent cell re-distribution step, by which a subset of wells of the array of wells wells that receive more than one cell (e.g., in a cell-saturated state) can be corrected to contain only a single cell by the redistribution step. However, receiving the population of target cells can include any method or sequence of distribution and re-distribution steps to achieve the desired contents within each well.

Block S210 is preferably performed as a first step of method 200, prior to any other cell or particle distribution steps, and wherein the array of wells has no other cell or non-cell particle inside the wells (e.g. the wells are in an unoccupied state prior to Block S210). However, Block S210 can be performed at any other suitable time, such as following distribution of the population of particles in Block S220, and/or repeated after a first cell distribution step. Furthermore, Block S210 or substeps within Block S210 can be repeated any number of suitable times in order to achieve desired distribution of target cells into the array of wells.

Distributing the population of target cells into the array of wells also functions to maximize cell viability during the capture of the target cells into the wells. In a first variation, an initial distribution step for the population of target cells can include loading the cells into the wells by gravity-induced entry, without additional physical forces applied to the cells. In an example, gravity-induced entry of cells into the array of wells can be achieved by pipetting small aliquots (e.g., ranging from 50-500 ul per aliquot) of the sample at different regions of the array, and incubating the biological sample at the open surface of the array (at which the open ends of each well are located) for an allotted period of time to allow target cells to enter the wells by gravity. More specifically, each aliquot can be delivered to a different region of the array of wells within a fluid reservoir superior to the array of wells to distribute the sample across the open surfaces of each well, generating a fluid layer sitting above the array of wells from which cells can descend into the wells. In variations, time periods allotted for gravity-induced entry of single target cells into the array of wells can range from 5 minutes to 60 minutes for a volume of 1 mL (e.g., approximately 20 minutes for K562 cells, and approximately 30 minutes for PBMCs). However, gravity-induced entry of cells can also be achieved by any other suitable method, such as: smearing the biological sample at the array of the substrate, maintaining a stable fluid layer of the biological sample within the fluid reservoir at a consistent, steady-state velocity, and/or in any other suitable manner of sample deposition and distribution that minimizes application of additional physical forces onto the target cells.

In a second variation, distribution of the population of target cells can include application of force to accelerate the speed of cell capture beyond the forces of gravity alone. In one example, distribution of the target cells can be achieved by cytospinning the substrate with the biological sample about an axis parallel to the broad surface of the substrate, cytospinning the substrate with the biological sample about an axis perpendicular to the broad surface of the substrate, or cytospinning the substrate with the biological sample about an axis oriented at any suitable angle relative to the broad surface of the substrate. Furthermore, in applications of Block S210 including cytospinning, an axis of rotation can be offset from any suitable reference point of the substrate, in any suitable manner. In another variation, distribution of the sample across the open surfaces of the array of wells can be achieved by gently tipping or rocking the substrate about a transverse axis passing through the midpoint of the substrate, or any other suitable axis of rotation. However, capturing the cells can include any other suitable method for sample distribution to encourage efficiency and speed of cell entry into the wells, while minimizing cell damage.

Block S210 can optionally include an additional re-distribution step to ensure optimal distribution of cells and maximize the number of target cells that are captured in single-cell format. In a preferred embodiment, as shown in FIG. 21, re-distribution comprises flowing a cell distribution fluid along a fluid path through a fluid reservoir parallel to the surface plane 118, wherein the fluid reservoir spans the array of wells along the open ends of the wells at the surface plane 118. In one variation, re-distributing can impart a force from the cell distribution fluid to a subset of partially retained cells (crossing over the surface plane 118), egressing the partially retained cells out of their respective cell-saturated wells, and transmitting the partially retained cells downstream of the array of wells to wells that are capable of receiving cells (e.g., in an unoccupied state, cell-accessible state). However, re-distributing can additionally and/or alternatively function to transmit any subset of cells across the array of wells, with any position relative to the array of wells (e.g., cells that are above the surface plane 118 and distal from the array of wells within the fluid reservoir), to wells in any other occupied state (e.g., wells containing one or more cells, wells containing one or more non-cell particles). In a preferred application, re-distribution in Block S210 can improve single-cell capture efficiency, wherein at least 50% of the cells within the population of target cells are captured in single-cell format.

The cell distribution fluid used for cell re-distribution can be any suitable fluid. In one variation, the cell distribution fluid has a density less than the solution within the well cavities of the array of wells, such that when the cell distribution fluid is flowed across the fluid path superior the array of wells, the cell distribution fluid does not readily enter the well cavity 128 of the wells, and therefore can only egress cells that cross the surface plane 118 of the substrate, and protrude into the fluid path. However, the cell distribution fluid can have any suitable density or characteristic that can assist in transmitting partially retained cells or cells above the surface boundary of the substrate downstream of the fluid path.

Furthermore, the flow rate and flow direction of the cell distribution fluid can be modulated and controlled. In a preferred variation, the flow rate and flow direction can be controlled by a fluid delivery module comprising a flow control subsystem that can apply a net positive or a net negative pressure at either side of the fluid reservoir through which the cell distribution fluid can flow. The flow direction can be unidirectional along the fluid path, but can additionally and/or alternatively be bidirectional, multidirectional, randomized, and/or at any angle relative to the fluid path to permit exposure of the cells within the cell distribution fluid to the open ends of cell-accessible wells. In one example, re-distribution can include at least one flow cycle of the cell distribution fluid wherein the flow direction alternates between a first forward direction and a second reverse direction opposing the forward direction, wherein partially retained cells that are egressed from the wells by fluid flow in the first forward direction can be washed back towards the array of wells by fluid flow in the second reverse direction in order to access cell-accessible wells of the array of wells. The number of redistribution flow cycles can be any suitable number of cycles necessary such that at least a majority of the target cells in the population of cells is retained below the surface plane 118 of the substrate within the array of wells. In a preferred application, re-distribution results in a maximum number of target cells of the population of target cells being captured in single-cell format within the array of wells. However, the cell distribution fluid flow rate and flow direction can be otherwise configured.

In a preferred application, as shown in FIG. 21, the wells of the array of wells are configured to permit a maximum of a single cell to be fully retained by the well below the surface plane 118. As such, any additional cell entering the well beyond the first fully retained cell will not be permitted to descend below the surface plane 118. Instead, the additional cell will protrude from the open end of the well, traversing the surface plane 118 between the well cavity 128 and the fluid path and thereby becoming accessible by the cell distribution fluid during a subsequent re-distribution step. In a first variation wherein Block S210 is performed as the first step of method 200 and wherein each well of the array of wells is in an unoccupied state containing no other cell or non-cell particle, the initial distribution step(s) for receiving the population of cells into the array of wells can result in any output combination of a first subset of wells of the array of wells receiving a single cell, defined herein as a particle-accessible state or a single-cell state; a second subset of wells receiving more than one target cell, defined herein as a cell-saturated state; and a third subset of wells receiving no target cells, defined herein as an unoccupied state (FIG. 21). Upon completion of the initial distribution step, only the first subset of wells has successfully captured single cells in each well and are useful for subsequent processing steps of the preferred application involving single-cell capture. In order to increase the number of wells in the first subset of wells (to increase the efficiency of single cell capture into the array of wells), additional cells localized in the second subset of particle-saturated wells can be optionally re-distributed to wells in the third subset of unoccupied wells, using an additional re-distribution step. In a second variation, the initial distribution step(s) for receiving the population of cells can result in an output condition wherein a subpopulation of cells remains above the surface plane 118 of the substrate and within the fluid reservoir. In order to utilize the subpopulation of cells that are available to populate the array of wells and increase the number of wells in the first subset of wells, the sub-population of cells can be optionally re-distributed to wells in third subset of unoccupied wells, using the additional re-distribution step.

Block S210 can be performed at a low temperature, using the thermal control module described in Section 1. In a preferred variation, the temperature of the array of wells is maintained at less than 10° C., however Block S210 can additionally and/or alternatively be performed at any other suitable temperature to maintain the viability of the population of target cells within the array of wells.

In order to facilitate efficient capture of the population of target cells in single cell format, Block S210 can be performed using a biological sample containing a specific ratio of target cells to the number of wells in the array of wells. In one variation, the number of target cells in the biological sample is preferably less than 20% of the number of wells in the array of wells. Preferably, the ratio of the number of cells in the sample to the number of wells in the array can be as low as 1:10, though the ratio can be any other suitable ratio. In a specific example, for an array containing 200,000 wells, Block S210 can be performed using less than 20,000 target cells in the biological sample solution, (e.g., approximately 2,500 cells, 5,000 cells 10,000 cells, 15,000 cells, etc.). However, Block S210 can be performed using any suitable number of cells in the sample in relation to the number of wells in the array of wells, such as 150,000 cells in 200,000 wells, or 250,000 cells in 200,000 wells. Furthermore, capturing the cells can include any other suitable concentration of cells in the sample in order to encourage single cell capture.

Block S210 can additionally include preparing the biological sample containing the population of target cells S212 prior to the distribution of the biological sample to the array of wells. In variations, Block S212 functions to enhance the efficiency of target cell capture within the array of wells by increasing the concentration of target cells within the sample, and can comprise one or more of: spiking cells into the biological sample, combining a pre-fixing solution with the biological sample, adding saline to the biological sample, and delivering the biological sample into the array of wells; however, Block S212 can additionally or alternatively comprise any other suitable biological sample preparation step. For instance, the biological sample can include a cell population of interest as the target cell population, thus eliminating a need for spiking cells into the biological sample. The biological sample can include a raw biological sample (e.g., blood, urine, tissue), enriched cell lines (e.g., isolated from blood), or augmented target cells (e.g., bound to small particles, pre-labeled with a marker). In a first variation, the biological sample is an enriched population of cancer stem cells isolated from blood. In a second variation, target cells (e.g., T-cells, B-cells, cancer stem cells) are bound to a small particle to selectively increase effective cell size. In a third variation, target cells are prelabeled with a fluorescent label, gold nanoparticle, or chemical linker to aid in downstream identification and/or quantification of the cells. However, the biological sample can include any other suitable component and be pre-processed in any suitable manner.

In an example, using a specific example of the system 100 described above, Block S212 can comprise delivering the biological sample (e.g., 2 mL of whole blood), with a cell population of interest (e.g., MCF7 breast cancer cells, SKBR3 breast cancer cells, LnCAP prostate cancer cells, PC3 prostate cancer cells, HT29 colorectal cancer cells) prepared with or without cell spiking, to the fluid reservoir 160 and rotating the cylindrical cartridge of the fluid delivery module, such that a chamber containing an appropriate biological sample preparation solution can be punctured by the actuation system. The biological sample preparation solution can then flow into the fluid reservoir 160, to be combined with the biological sample, and then be delivered into the array of wells upon pressure generation by the pump of the flow control subsystem. Block S212 can, however, comprise any other suitable method of preparing a biological sample, including the target cell population, to be received by the array of wells at the substrate.

Block S210 can additionally include priming the substrate in Block S214 prior distribution of the biological sample to the array of wells, which functions to minimize trapped air and/or cell aggregates within the fluid channels of the substrate, and to prepare the system for receiving a biological sample including the target cell population. Priming the substrate includes flowing a priming reagent or buffer solution through the fluid channels of the substrate. In an example, delivering a buffer solution into the array of wells comprises delivering a buffer comprising 1% bovine serum albumin (BSA) and 2 mM ethylenediaminetetraacetic acid (EDTA) in 1× phosphate buffered saline (PBS); however, delivering a buffer solution can comprise delivering any other suitable fluid into the array of wells. In the example, using a specific example of the system 100 described above, priming the substrate in Block S214 can comprise rotating the cylindrical cartridge of the fluid delivery module, such that a chamber containing the buffer solution can be punctured by the actuation system. The buffer solution can then flow into the fluid reservoir 160, to be delivered into the manifold and into the microfluidic chip upon pressure generation by the pump. The buffer solution can then be driven in a forward direction and a reverse direction, by the pump, to adequately remove bubbles from the array of wells. Block S214 can, however, comprise any other suitable method of delivering a buffer solution into a array of wells configured to capture the target cell population.

In another variation, priming the substrate can function to sterilize the substrate. In an example, sterilization of the substrate can include adding a total of 800 ul of 100% ethanol to the substrate, followed by incubating the substrate under ultraviolet light (e.g., via the imaging subsystem 194 as described in Section 1) for approximately 5 to 20 minutes to sterilize the substrate. However, the substrate can be primed prior to the distribution of cells and/or non-cell particles in any other suitable manner.

After capturing the population of target cells, Block S210 can optionally include gathering information from the captured cells, including identifying, quantifying, and locating the captured cells in Block S216. Block S216 is preferably achieved using the imaging subsystem 194 described in Section 1, but can be achieved using any other method and/or component of the system 100. The information obtained in Block S216 can further be used to inform, modify, and/or adjust settings for subsequent or concurrent steps in method 200. In one variation, the captured population of target cells can be phenotypically characterized and/or quantified by staining the captured cells with fluorescent antibodies (e.g., directly or indirectly labeled). For example, specific stains can be used to quantify the number of viable cells, specific states of the cells in their cell cycles and/or sub-types of the target cells. Furthermore, imaging of the array of wells via the imaging subsystem 194 can also be used to ascertain the exact number of captured cell-particle pairs so that the appropriate parameters for the downstream library preparation and/or next-gen sequencing can be determined (e.g., to determine a number of PCR amplification cycles and/or sequencing depth). In a first example, information regarding the number of cells that have been successfully captured in single-cell format can be used to determine and select the number of particles (e.g., increasing or decreasing concentration of particles in solution) required for efficient distribution and single cell-particle capture in Block S220. In a second example, information indicating that a majority of cells in the sample have already been captured successfully in single-cell format can be used to instruct the system to skip and/or adjust an additional re-distribution step and/or processing step, thereby decreasing processing time and enhancing performance. Alternatively, information indicating cell aggregation or inefficient cell capture (e.g., a majority of uncaptured cells remaining in the fluid reservoir) can instruct the system to include an additional re-distribution step and/or processing step. In a second variation, information regarding individual locations of captured cells and their relative distribution within the array of wells can be used to instruct components of the fluid delivery module described in Section 1 to adjust settings for more efficient capture. In one example, information indicating that a majority of captured cells are located at a first side of the substrate in comparison to a second side of the substrate can inform the flow control subsystem to select a specific flow rate and flow direction to flow uncaptured and/or partially retained cells towards the second side of the substrate during a re-distribution step. In another example, location information of wells containing single cells (e.g., particle-accessible wells) can be used by the flow control subsystem to select a specific protocol for distributing the population of particles in Block S220 in order to enhance the probability that particle-accessible wells receive particles to achieve an ideal state. However, information regarding the captured cells is not limited to quantification and location within the array of wells, and can be used to instruct and modify any of the steps in method 200. Furthermore, Block S216 can be repeated any number of times throughout method 200, and can be performed before, after, and/or during any step of method 200, including to assess and instruct the performance of individual steps of cell distribution in Block S210, particle distribution in Block S220, and particle re-distribution in Block S230.

Block S210 can optionally include selecting an array of wells comprising wells with a specific dimension, geometry, density, and/or spatial arrangement within the substrate in Block S218, according to at least one of: the dimensions and numerosity of the desired target cells, the dimensions and numerosity of the particles used in Block S220, the capture assay or protocol performed, and the desired output condition for the well state upon completion of at least a portion of method 200, including the number of cells and/or particles desired to be captured in each well. The wells of the array of wells can posses a range of dimensions that can impact the output states of wells upon completion of Block S210 and/or Block S220, including horizontal cross-section, vertical cross-section, width of the open end of each well, height of the well cavity 128, and total volume of the well cavity 128. In one variation, for which it is desired that an ideal state of the well comprises receiving exactly one cell and one particle into the same well, the dimensions of the well can be sufficient enough to retain both the cell and the particle below the surface plane 118 (e.g., the open end of the well), but not sufficient enough to retain a second cell after a first cell has been received in Block S210 (resulting in cell-saturated state), or more than one particle after a first cell has been received in Block S210 (resulting in a particle-saturated state). In a specific example, for a population of target cells comprising target cells having a characteristic diameter between 10-15 micrometers and a population of particles having a characteristic diameter between 18-22 micrometers, the height of the well cavity 128 can range between 20 and 50 micrometers, and the width of each well (e.g., horizontal cross section) can range between 20 and 30 micrometers. In another example, for which it is desired that an ideal state of the well comprises receiving either exactly one cell (e.g., between 10-15 micrometers) or one particle (e.g., between 18-22 micrometers) (but not both a cell and a particle), the height of each well cavity 128 can range between 10 and 30 micrometers, and the width of each well (e.g., horizontal cross section) can range between 20 and 30 micrometers. However, the dimensions of the wells can be selected based on any other suitable criteria and can be matched and correlated to the dimensions of the population of cells and/or dimensions of the population of particles used in any step of method 200.

2.2 Method—Distributing the Population of Particles

Block S220 recites: distributing a population of particles into the array of wells. Block S220 preferably functions to colocalize a single particle of the population of particles with a single target cell previously retained within a particle-accessible well (e.g., in the first subset of wells) described in a variation of Block S210, thereby capturing a single cell-particle pair within individual wells. However, Block S220 can be performed before or after any other step in method 200, and can be used to distribute any number of particles into individual wells of the array of wells, including wells previously containing any number of cells and/or non-cell particles, and/or into wells that are previously unoccupied. In a preferred application, as a result of consecutive steps in Block S210 and Block S220, the target cell and the particle are fully retained by the well cavity 128 of the well (e.g., the cell-particle pair is retained below a surface plane 118 of the substrate), such that the particle comprising the cell-particle pair is not egressed from the well cavity 128 during re-distribution of particles in Block S230. However, Block S220 can be implemented in any other suitable manner in method 200, in order to distribute the population of particles across the array of wells, and to control the number of particles received and retained into individual wells of the array of wells.

Preferably, Block S220 is performed after receiving the population of target cells at the array of wells as described in Block S210, such that particles added to a well that is currently occupied by a target cell settle on top of the target cell and proximal the open surface of the substrate, however Block S220 can be additionally and/or alternatively performed prior capturing target cells at the array of wells, and in temporal relation to any other suitable step of method 200. To ensure that the population of particles is distributed uniformly into the array of wells and encourage a 1:1 ratio of target cell to particle per well, Block S220 can be followed by Block S230, wherein particles are redistributed across the array of wells, and analogous to redistribution of cells described in Block S210. However, Block S220 can include any other suitable steps.

In Block S220, the population of particles (e.g., microspheres, beads, etc.) received into the array of wells can be of any suitable material to convey desirable properties to the particles, including physical properties (e.g., nonswelling behavior, dissolveability), magnetic properties, optical properties, chemical properties (biocompatibility, binding affinities), and thermal properties. The particles can be made of polystyrene, silica, non-porous glass, porous glass, coated glass, and/or a combination of one or more suitable materials. The density of the particles is preferably greater than the buffer of the containing solution (e.g., at least 1.1 g/cc) but can alternatively be of any other suitable density.

Preferably, the particle has a characteristic dimension configured such that only a single particle can enter a well currently occupied by a single target cell below the surface plane 118, in order to colocalize the single cell-particle pair within an individual well. In a preferred variation, each particle in the population of particles is a spherical particle including an outer shell with a diameter between 10 to 30 micrometers. To accommodate facile distribution and settling into the array of wells, the population of particles can be produced with a substantially monodisperse geometry. In examples, the population of particles can posses a characteristic dimension including a diameter of one of: 20 microns, 15 microns, 30 microns, 35 microns, and/or 40 microns, with a standard deviation of less than 20% or less than 15%, thus improving the efficiency of single cell-particle pair capture to above 50%. In addition, the uniformity of the population of particles can enable a higher percentage of particle retrieval upon completion of various steps of the single cell sequencing preparation biochemical processes (in Block S250). To minimize sedimentation and improve distribution, the solution containing the population of particles can optionally include approximately 10% glycerol.

In a specific example of this variation, the particles are glass beads with a polystyrene coating approximately 20 micrometers in diameter (e.g., 15 to 25 micrometers), but can alternatively and/or additionally be any other suitable diameter. Furthermore, the particles can be any other suitable 3-dimensional (e.g., rectangular, triangular, oblong, rod or any other polygonal shape) or 2-dimensional shape (e.g., a sheet). In a specific example, wherein the height of the well is approximately 40 micrometers, and wherein the target cell has a characteristic dimension that ranges between 15-25 micrometers, particles with a diameter between 18-22 micron can be used in Step S220 to colocalize a single particle with a single captured cell below the surface plane 118. However, implementation of method 200 by system 100 can be configured in any other suitable manner.

In variations of Block S220, the outer shell of the population of particles can include various surface properties and/or surface features that function to interact with the captured target cells, biomolecules of the captured target cells, the interior surface 130 of the well cavity 128, the solution within the well, and/or any other suitable component of the system and/or method described in this application.

In a first variation, as shown in FIG. 20, the outer shell of the particles can be conjugated to a probe and/or set of probes 36 (e.g., oligonucleotide, chemical linker, etc.) that preferably function to bind to intracellular nucleic acid content (e.g., mRNA, DNA, proteins, etc.) released from the cell and additionally or alternatively to facilitate downstream processes (e.g., reverse transcriptase, polymerase chain reaction (PCR), etc., as described in variations of Block S240. However, the set of probes 36 can be implemented in any other manner in order to perform analysis of the target cells. In variations wherein the probe comprises a biomolecular interaction region comprising a nucleotide sequence, the biomolecular interaction region of individual probes can additionally or alternatively contain any combination of at least one of: a primer sequence (e.g., a PCR handle), a cell barcode used to identify the cell from which the nucleic acid content originated (e.g., a unit identifier), a unique molecular identifier (UMI) to label different molecules (e.g., genetic material) of the same cell (e.g., one barcode can have multiple UMIs), a poly-DT sequence which enables capture of polyadenylated mRNA species, and surface hydroxyls reacted with a polyethylene-glycol (PEG) derivative to serve as a support for oligo synthesis. In addition to the biomolecular interaction region, each probe can include a particle linking region including a particle linker that couples the probe to the particle, and additionally or alternatively a substrate linking region including a functional linker that binds to a portion of a cell or portion of a surface of a well (e.g., via protein, antibody affinity, chemical interactions) (FIG. 20, FIG. 7). In a specific example, a single particle coupled to a single set of probes 36 on the outer shell of the particle is received into the well cavity 128 of an individual well during Block S220. The set of probes 36 is coupled to the outer shell of a particle by a particle linker containing a photo-cleavable bond that can be activated using ultraviolet (UV) wavelengths. Under UV irradiation, the set of probes 36 can be controllably detached from the particle within the well, and the particle can be optionally removed from the well cavity 128, thereby allowing the set of probes 36 to interact with the environment within the well cavity 128 without the physical constraints of the particle. However, the biomolecular interaction region, the particle linking region, and substrate linking regions of the set of probes 36 can be otherwise configured.

In another variation, the outer shell of each particle can be modified to tailor the linker density of barcoded oligonucleotides to a specific number in order to maximize the number of biomolecules captured from the single cell lysate, while minimizing effects of steric hindrance during downstream processing of genetic complexes formed with the probe (e.g., during Block S240), such as cDNA reverse transcription, and/or PCR amplification. For single cell RNA-seq, the particles can be tailored to have a linker density between 0.1 to 5 micro-mole/gram. For example, the linker density on the particles can be tailored such that the maximum number of biomolecules from a single cell lysate can be one of approximately: 100,000 molecules, 500,000 molecules, 750,000 molecules, 1,000,000 molecules, 2,000,000 molecules, 3,000,000 molecules, 4,000,000 molecules, and/or 5,000,000 molecules. Prior to oligonucleotide binding, the outer surface area and/or porosity of the particles can be tailored by various processes such as chemical etching, chemically growing a thin (up to few, 0.1, 1, 2, and/or 3 micron in thickness) layer of functionalized surface. In another variation, the outer shell of the particles can include multiple and distinct functional groups of predetermined density to be able to bind different types of biomolecules from the single cell or single cell lysate, such as: DNA, mRNA, proteins, metabolites, glycans, cellular enzymes, etc. However, the features and characteristics of the outer shell of the population of particles can be configured in any other suitable manner.

Furthermore, the surface features of the population of particles can be otherwise configured to perform any other suitable function or interaction within the array of wells. In a second variation, the outer shell of the particles can include surface-bound moieties able to bind to an antibody or any other suitable protein either on the cell or on the wall of the well. In a third variation, the outer shell of the particles can contain synthetic or organic materials that improve the biocompatibility of the particle (e.g., PEG, collagen, etc.). In a fourth variation, the outer shell of the particles can contain a physical feature that allows the particle to enter and be retained within a well, such as a hook, adhesive, or extendable volume. However, the outer shell of the particles can be otherwise configured.

Furthermore, each particle of the population of particles can optionally contain, within the particle, a synthetic reagent, biochemical agent, and/or an organic material that can be used to conduct biochemical assays on the captured cell. In a variation, the particles can be manufactured to contain a drug that can be released from the particle (e.g., triggered by time, temperature, pH, etc.), with applications for high-throughput drug testing on single cells within the array of wells. For example, the outer shell of the particle can be composed of a biodegradable material the dissolves over time at a certain temperature, thereby releasing the drug in the presence of the target cell within the well. However, the population of particles can be configured in any other suitable manner.

To perform Block S220, the ratio of the number of particles to the number of wells is at least 1:1 and is preferably at least 1.5:1, but can be any other suitable number of particles. In a variation wherein capture of a single cell-particle pair is desired, the number of particles within the particle solution is selected such that every well that contains a single cell receives at least one particle. In a specific example, wherein the number of wells in the array is 200,000, the number of particles added to the array preferably ranges between 300,000 to 400,000 particles. Furthermore, as previously described, obtaining information about the number of cells captured in single-cell format upon completion of Block S210 can be used to assist in selection of a range of number particles within the particle solution, to enhance the desired capture efficiency, and minimize under or over-saturation of the array of wells with particles. In one example, upon determining that a range of 5000 to 6000 wells of an array of 200,000 wells are in a particle-accessible state, the number of particles in the particle solution can be selected within a range of 10,000 to 50,000 particles to minimize occurrences of particle-saturation states, thereby improving colocalization efficiency and/or speed of a single particle to a single cell. However, selecting the number of particles added to the array of wells in Block S220 can be performed in any other suitable manner.

Distributing the population of particles into the array of wells includes an initial distribution step which functions to load the particles into the array of wells, similar to initial distribution of the cells, as described in Block S210. In variations, the population of particles can enter the array of wells by gravity-induced entry (e.g., pipetted into the array in multiple aliquots), with an applied force, (e.g., cytospinning the substrate with solution containing the population of particles), and/or flowed into the fluid reservoir 160 by the reagent delivery module as described in Section 1. In a specific example, a particle solution containing a range of between 200,000 to 600,000 particles can be distributed to the array of wells by pipetting small aliquots of the solution at various regions of the array of wells to form a uniform fluid layer within the fluid reservoir superior the open ends of the wells, followed by centrifuging the array of wells at 330 rpm for 4 minutes. However, initial distribution of the particles can be performed by any other suitable manner using any appropriate component of the system 100.

Figure 22:
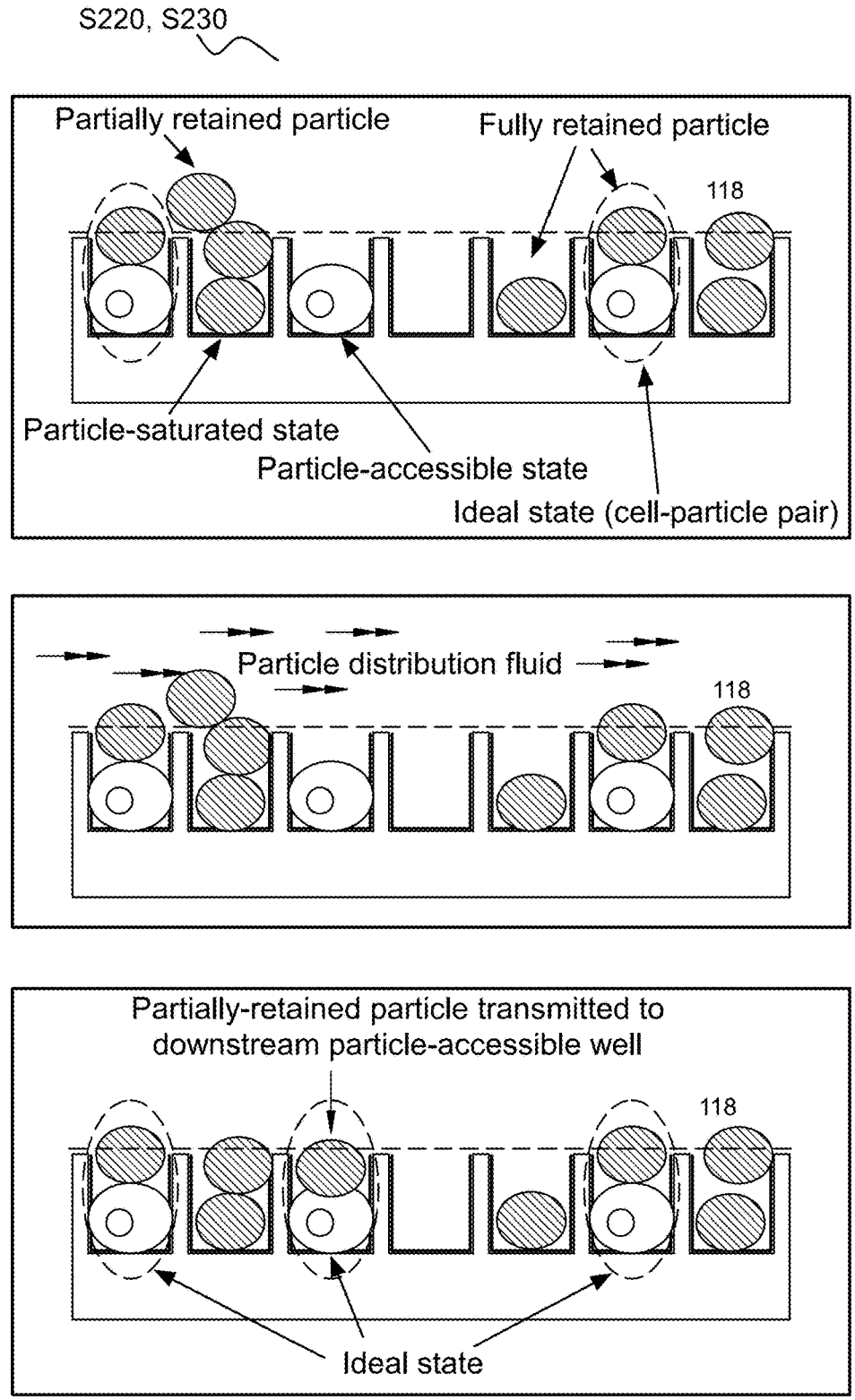
FIG. 22 depicts a schematic representation of a variation of a portion of an embodiment of a method for isolating and analyzing cells.

In a preferred application wherein Block S220 is performed after Block S210, the initial distribution step(s) for receiving the population of particles into the array of wells can result in any output combination as shown in FIG. 22, including: a first subset of wells of the array of wells retaining a single cell receiving a single particle, defined herein as an ideal state containing a single cell-particle pair; a second subset of the array of wells retaining a single cell receiving more than one particle, defined herein as a particle-saturated state; a third subset of unoccupied wells receiving only a single particle, defined herein as a cell-accessible state, and a fourth subset of unoccupied wells receiving more than one particle (FIG. 22). Upon completion of the initial distribution step, only the first subset of wells in the ideal state has successfully captured a single cell-particle pair in each well and are useful for subsequent processing steps of the preferred application involving single-cell and/or single cell-particle pair capture. In order to increase the number of wells in the first subset of wells in the ideal state (to increase the efficiency of single cell-particle capture into the array of wells), additional particles localized in the second subset of particle-saturated wells can be optionally re-distributed to wells that remain unoccupied after the initial distribution step and/or wells that remain in the particle-accessible state (e.g., containing only a single cell) after the initial distribution step, as described in Block S230. Additionally and/or alternatively, partially retained particles and/or excess particles remaining in the fluid reservoir can be egressed from the fluid reservoir through an outlet coupled to a waste chamber. However, Block S220 can be performed in any other suitable manner.

2.3 Method—Redistributing the Population of Particles

In Block S230, redistributing the population of particles functions to ensure optimal distribution of particles across the array of wells, and to maximize the number of particles that can access the array of wells, preferably to enable single cell capture and/or single cell-particle pairing within individual wells. Block S230 can redistribute particles that have been added to the array of wells, but have not been fully retained within individual wells (e.g., into the well cavity 128, below the surface plane 118), including particles that remain in the fluid reservoir above the surface plane 118 (e.g., excess particles), and particles that have entered individual wells, but exceed the volume capacity of the well and traverse the surface plane 118 into the fluid path. In a preferred embodiment, similar to the cell re-distribution step of Block S110, particle re-distribution comprises flowing a particle distribution fluid along a fluid path through a fluid reservoir parallel to the surface plane 118, wherein the fluid reservoir spans the array of wells along the open ends of the wells at the surface plane 118. In one variation, as shown in FIG. 22, re-distributing can impart a force from the particle distribution fluid to a subset of partially retained particles (crossing over the surface plane 118), egressing the partially retained particles out of their respective particle-saturated wells, and transmitting the partially retained particles downstream of the array of wells to wells that are capable of receiving particles (e.g., in an unoccupied state, particle-accessible state). However, re-distributing can additionally and/or alternatively function to transmit any subset of particles across the array of wells, with any position relative to the array of wells (e.g., particles that are above the surface plane 118, particles that are distal from the array of wells within the fluid reservoir), to wells in any other occupied state (e.g., wells containing one or more cells, wells containing one or more non-cell particles).

The particle distribution fluid used for particle and/or cell re-distribution can be any suitable fluid, or a fluid containing any suitable component to flow across the upper surface of the array of wells. In one variation, the particle distribution fluid has a density less than the solution within the well cavities of the array of wells, such that when the particle distribution fluid is flowed across the fluid path superior the array of wells, the particle distribution fluid does not readily enter the well cavity 128 of the wells, and therefore can only egress particles that cross the surface plane 118 of the substrate, and protrude into the fluid path. However, the distribution fluid can posses any other suitable characteristic. In another variation, wherein the fluid reservoir includes a set of magnetic elements (e.g., along the fluid path), the particle distribution fluid can contain a set of magnetic particles that can be used to control and/or concentrate the flow of the distribution fluid across a specific spatial region relative to the array of wells (e.g., only through the fluid path proximal the magnetic elements in the fluid reservoir). However, the distribution fluid can posses any other functional components that can modify the flow rate and/or flow direction of the distribution fluid (e.g., electrostatic, physical, chemical, thermal properties). Furthermore, the particle distribution fluid can have any suitable density, characteristic, and/or contain components that can assist in transmitting partially retained particles or excess particles above the surface plane 118 of the substrate downstream of the fluid path.

Preferably, the flow rate and flow direction of the particle distribution fluid can be modulated and controlled. Similarly to a preferred variation in Block S110, the flow rate and flow direction can be controlled by a fluid delivery module comprising a flow control subsystem that can apply a net positive or a net negative pressure at either side of the fluid reservoir through which the particle distribution fluid can flow. The flow direction can be unidirectional along the fluid path, but can additionally and/or alternatively be bidirectional, multidirectional, randomized, and/or at any angle relative to the fluid path to permit exposure of the particles within the particle distribution fluid to the open ends of particle-accessible wells. In one example, re-distribution can include at least one flow cycle of the particle distribution fluid wherein the flow direction alternates between a first forward direction and a second reverse direction opposing the forward direction, wherein partially retained particles that are egressed from particle-saturated wells by fluid flow in the first forward direction can be washed back towards the array of wells by fluid flow in the second reverse direction in order to access particle-accessible and/or unoccupied wells of the array of wells. The number of redistribution flow cycles can be any suitable number of cycles necessary such that at least a majority of the particles in the population of particles is retained below the surface plane 118 of the substrate within the array of wells. In a preferred application, re-distribution can result in at least 80% of particle-accessible wells being filled with a single particle to achieve an ideal state for the wells. However, the cell distribution fluid flow rate and flow direction can be otherwise configured.

As described in Block S216, the fluid flow rate and flow direction of cell and/or particle distribution fluids in Block S210, Block S220, and Block S230 can be modified and/or adjusted accordingly, and/or in real time during synchronous or asynchronous steps of method 200, according to the quantity and location of captured cells within the array of wells. In a preferred variation, the optical subsystem can record a set of images to obtain information regarding the abundance and distribution of particle-accessible wells, and can communicate instructions to the fluid delivery module and/or flow control subsystem to assist in the selection of at least one of: concentration of particles in the particle solution, flow rate of the particle distribution fluid, direction of the particle distribution fluid, temperature of the particle distribution fluid, and/or number of repeated cycles of re-distribution, in order to enhance capture efficiency. However, the parameters of redistribution in Block S230 can be manually determined by user input (before, during, and/or after one of Block S210, Block S220, Block S230), statically set (pre-determined, according to a stored setting), and/or otherwise determined. In another preferred embodiment, the extraction module can be used in operation with the imaging subsystem to retrieve one or more particles from a well containing more than one particle and dispense them into another well containing no beads, based on imaging feedback.

2.4 Method—Processing the Array of Wells

Block S240 recites: processing the array of wells, which can include one or more of: receiving at least a single process reagent at the array, thereby facilitating diffusive delivery of one or more process reagents to the cell population in at least one of single-cell format and single-cluster format, performing a biochemical process at the array of wells, analyzing the contents of the array of wells, and additionally and/or alternatively any other suitable process at the array of wells. Block S240 functions to enable seamless and rapid processing and analysis of the contents captured within the array of wells, without necessitating removal of the captured contents (e.g., cells and/or non-cell particles) from the array of wells, and furthermore can be used to process multiple arrays of wells simultaneously (e.g., 2, 4, 6, 10 arrays at a time). In preferred embodiments, portions of Block S240 can be performed automatically in coordination with components of system 100, wherein parameters of process reagent delivery including the sequence of multiple reagents, timing (e.g., dispense time, flow duration), velocity, direction, and/or volume of process reagents (e.g., using the fluid delivery module), parameters for temperature modulation of the array of wells and/or process reagents (e.g., using the thermal control module), and/or parameters for optical analysis (e.g., using the optical subsystem) can be determined, selected, and/or coordinated using stored settings, user input, and/or adaptive input and one or more processors of system 100. However, processing the array of wells can include any other suitable steps and/or parameters, and can be performed in any other suitable manner.

In variations, delivering one or more process reagents to the array of wells can function to perform one or more of: permeabilizing captured cells of the target cell population, post-fixing captured cells of the target cell population, blocking captured cells of the target cell population, washing captured cells of the target cell population, treating captured cells of the target cell population with an antibody cocktail, incubating captured cells of the target cell population, staining captured cells of the target cell population, lysing captured cells of the target cell population, isolating components within captured cells of the target cell population, and heating the array of wells. Step S240 can additionally or alternatively comprise any suitable step that prepares the cells of interest captured by the array of wells for analysis, such as delivering a hybridization buffer to the cells of interest, delivering particles and/or control probes to the cells of interest, dehydrating the cells of interest, and/or denaturing the cells of interest. In one variation, Step S240 can prepare cells of the target cell population for an analysis requiring a stain (e.g. fluorescent stain or histological stain). In another variation, Step S240 can prepare cells of the target cell population for an analysis involving electrophoresis. In yet another variation, Step S240 can prepare cells of the target cell population for a molecular diagnostic assay, such as PCR.

In variations, the process reagent(s) can be delivered to and distributed across the array of wells in a manner similar to that of distributing the biological sample or the distribution fluid at the array in variations described for Block S210, Block S220, and/or Block S230. In one example, as described in Section 1, a process reagent that is stored in a cartridge of a fluid delivery module can be dispensed from the cartridge and dispensed into the array of wells through a fluid reservoir 160 superior and directly fluidly coupled to the array of wells. To enhance the speed of performing various assays and processes at the array of wells, multiple process reagents can be stored (e.g., preloaded) in the reagent cartridge of the fluid delivery module until needed. The fluid delivery module functions to deliver the appropriate volume of desired reagent into the array of wells via the fluid inlet and into the fluid reservoir 160, where the fluid flow velocity is controlled by the pumping system, to prevent damage to the cells, and improve efficiency of the assay (e.g., the distribution of reagents within the wells, the distribution of the particles across the wells, etc.). Furthermore, fluid flow across the fluid reservoir 160 can be further controlled using the upper lid of the system to create a fluid layer at the fluid reservoir 160 to enhance the transit of the fluid across the fluid reservoir 160 and into the wells. To dispense the desired reagent into the fluid reservoir, Step S240 can comprise rotating the cylindrical cartridge of the fluid delivery module, such that a chamber containing a desired reagent can be punctured by the actuation system. The process reagent can then flow into the fluid reservoir 160, to be delivered across the array of wells upon pressure generation by the pump of the flow control module. However, dispensing the process reagents into the array of wells can be performed by any other subcomponent of system 100, manually by the user, or otherwise performed.

In addition, Block S240 can be performed in conjunction with the thermal control module to control the convective flow of the reagents across the fluid reservoir 160 and to maintain the temperature of the array of wells (e.g., to preserve cell viability, to preserve intracellular genetic content (e.g., mRNA, cDNA) viability, aid in diffusion of reagents into the wells, enhance speed of flow of reagents across the fluid reservoir 160, etc.). In variations, Block S240 can include transmitting or removing heat, through the substrate, to the cell population captured at the array, which functions to provide controlled incubation and/or thermocycling of the cell population with the process reagent(s) received in variations of Block S240. Heating preferably includes providing uniform heating and/or cooling at each well of the set of wells of the array; however, heating can alternatively include providing heating and/or cooling non-uniformly across the array (e.g., providing heat with a gradient to examine effects of different heating parameters on the cell population). In variations, heating can include contacting the substrate with at least one heating element, adjusting an environmental temperature of the substrate, and/or transmitting heat throughout the substrate by way of heating elements coupled to or embedded within the substrate. In one example, one or more heating elements can be coupled to the base of the substrate below the array of wells (FIGS. 31A-31C), which functions to provide rapid heating and/or cooling to the array of wells. The system can additionally and/or alternatively include one or more heating elements embedded within an upper lid of the substrate, which functions to modulate the temperature of the process reagents flowing through the fluid path of the fluid reservoir and enhance access to the interior of the wells (FIGS. 15A, 15B, and FIG. 16). However, transmitting and/or removing heat to the array of wells can additionally or alternatively be performed in any other suitable manner. In a variation wherein transmitting heat includes incubating the substrate, with the cell population and a process reagent for a desired amount of time at a desired temperature, transmitting heat can facilitate one or more of: lysing the cell population, fixing the cell population, permeabilizing the cell population, staining the cell population, performing immunochemistry for the cell population, binding a probe to intracellular nucleic acid content of the cell population, performing an in-situ hybridization assay (e.g., a fluorescence in-situ hybridization assay, FISH), performing polymerase chain reaction for nucleic acid content of the cell population, culturing the cell population, and any other suitable application. However, receiving the process reagent(s) and/or modulating the flow (volume, velocity, temperature, etc.) of the process reagent(s) can additionally or alternatively be performed in any other suitable manner for any other suitable application.

In one variation of Block S240, the process reagent can be a lysing reagent that releases at least one biomolecule, such as nucleic acid content (e.g., mRNA) and/or protein, from the population of target cells. Lysing the captured cells is achieved by adding the lysing reagent to the array of wells at a temperature below 15° C., followed by incubating the array of wells at approximately 25° C., and/or at slightly elevated temperature such as 50° C., to complete the reaction. In some variations, lysing the cells can include distributing a layer of oil (or other solution immiscible in the solution contained within the well cavities) over the top of the wells prior to performing the lysing reaction, to prevent released content from transferring to adjacent wells in the array of wells. In another variation, lysing the cells can include distributing a layer of air over the top of the wells prior to performing the lysing reaction, to prevent released content from transferring to adjacent wells in the array of wells.

Figure 23:
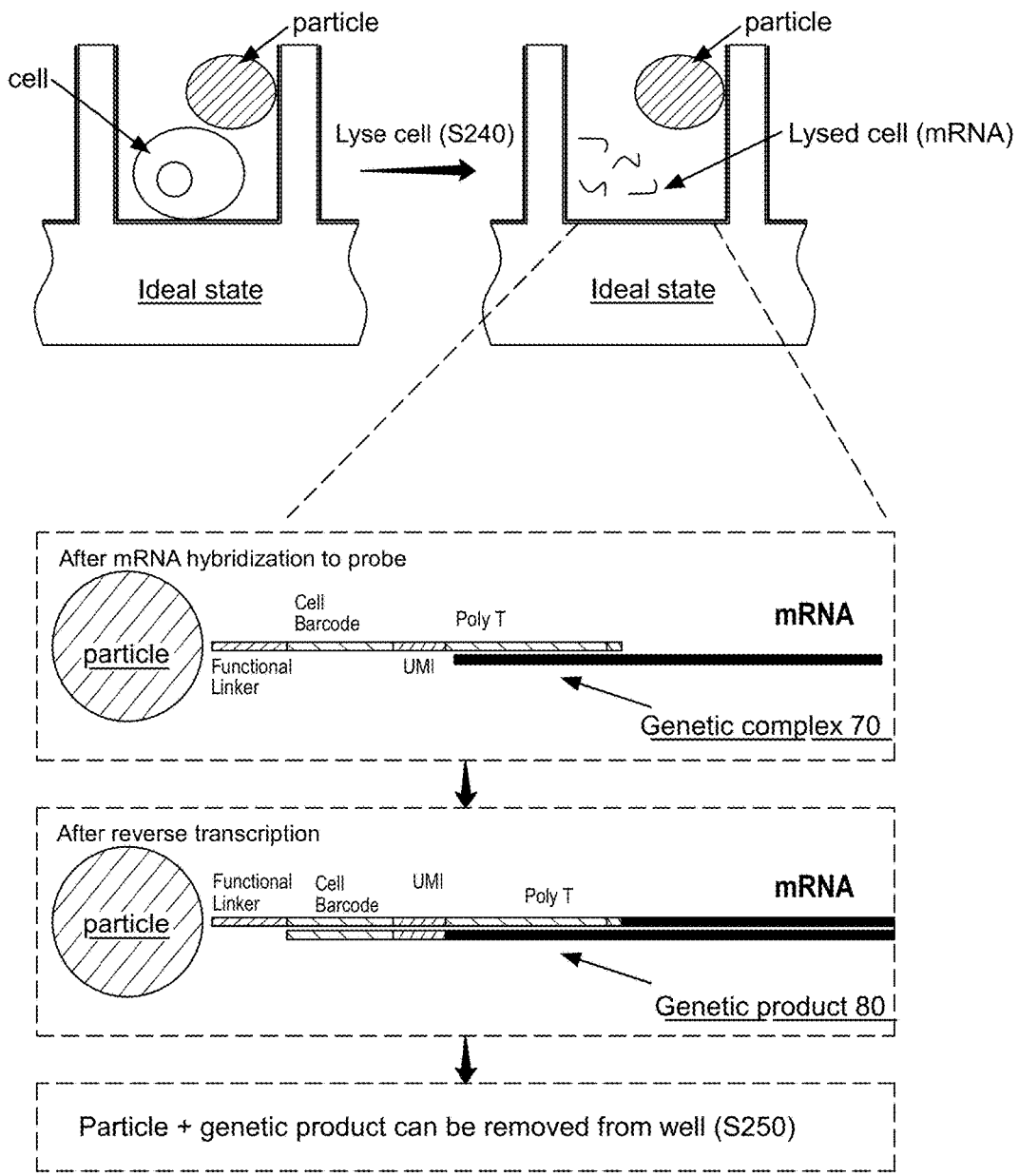
FIG. 23 depicts a schematic representation of a variation of a portion of an embodiment of a method for isolating and analyzing cells.

In a preferred application utilizing the cell-particle pairs captured within wells of the array in the ideal state, the temperature of the array of wells can be again reduced to below 15° C. (approximately 5° C. to preserve the mRNA) after the lysing reaction, and biomolecules released from each of the lysed target cells can hybridize to the probes of the corresponding particles (e.g., particles colocalized within the same well as the target cell, associated with the cell-particle pair), forming a set of genetic complexes 70 (mRNA from the cell hybridized with nucleotide sequences of the set of probes) associated with each captured cell. Preferably, as shown in FIG. 23, each genetic complex of the set of genetic complexes 70 can include at least a probe and a biomolecule (e.g., mRNA) derived from the target cell, wherein a single set of genetic complexes 70 (e.g., all associated with biomolecules derived from the same cell) is contained within each individual well of the array of wells. Generating the set of genetic complexes 70 can be achieved when each particle of a population of particles includes a set of probes 36, each probe including a unit identifier (e.g., a unique nucleotide sequence for each particle) as well as a biomolecule identifier (e.g., a unique nucleotide sequence for each probe, UMI), as further described in Block S220. Upon cell lysis, multiple molecules released from a single target cell can be identified as originating from the cell of the cell-particle pair by binding and/or hybridizing each individual biomolecule to a respective probe of the set of probes 36 of the particle (e.g., complementary nucleotide pairing), thereby labeling each biomolecule with a unique nucleotide sequence including the unit identifier and the biomolecule identifier that can be easily identified during downstream processing (e.g., RNA, DNA sequencing). Thus, genetic complexes with the same unit identifier in the nucleotide sequence can be considered to have been derived from the same target cell in the cell-particle pair, enabling individual analysis of multiple molecules from the same cell to occur in parallel. In order to reduce non-specific labeling of mRNAs to individual probes, various steps including optimizing buffer wash speed, setting an optimal binding time to capture all mRNA transcripts within an individual well, on-chip cooling during lysis and hybridizing steps, and increasing probe density can be used. Additionally and/or alternatively, specific molecules and/or particles can be added to the post-lysis wash solution to capture unbound cellular content egressed from a cell, thereby preventing unbound cellular content from diffusing into a neighboring well. However, the set of genetic complexes 70 can be otherwise configured and can include any suitable subcomponent in association with any biomolecule, cell, particle, and/or well of the array of wells.

In an alternative embodiment of method 200, as shown in FIG. 24, FIG. 25, and FIG. 26, a set of probes 36 can additionally and/or alternatively be immobilized to the interior surface 130 of individual well cavities, left free-floating in solution within individual wells, and/or configured in any suitable manner. In one variation, biomolecules released from a target cell can bind to the set of probes 36 without co-localization of a single particle and a single cell within the well. Specifically, particles can be distributed to the wells in single-particle format in a method similar to that described for Block S220 and Block S230 prior to capturing cells as described in Block S210, wherein each individual particle includes a set of probes 36 containing a common unit identifier. Rather than receiving the population of particles to generate a cell-particle pair in each well, receiving the population of particles can result in an output condition wherein single particles are captured within each well. In a preferred application of this embodiment of method 200', single-particle capture within each well prior to single-cell capture can enable delivery of the sets of probes to each individual well (FIG. 26). Upon single-particle capture, the set of probes 36 can be detached from their associated particle and released into individual well cavities, thereby permitting the contents of each well to be identifiable by the unit identifier of the set of particles therein. Each set of probes 36 that has been released is preferably immobilized to an interior surface 130 of the well cavity 128 (e.g., via biochemical bond, antibody-antigen reactivity), effectively labeling each well with the unit identifier and allowing the particles to be removed from the wells, thus permitting the array of wells to be accessible by a population of target cells. Following the addition of the sets of probes to individual well cavities, a population of target cells can be distributed to the wells, as described in Block S210, whereby target cells can be captured in single-cell format (e.g., one cell to each well) (FIG. 25). Upon single cell capture, cell lysis can be performed as described above, wherein the set of genetic complexes 70 comprising the released biomolecules and the set of probes 36 are contained within each well and coupled to the interior surface 130 of the well cavity 128, rather than the particle). In this way, directly labeling each well with the unit identifier can increase the speed and efficiency of generating sets of genetic complexes from a population of target cells. However, the contents of the array of wells, including genetic complexes, cells, biomolecules, and/or non-cell particles, can be processed in any other suitable manner.

In a second variation of Block S240, process reagents can be added to the array of wells to perform cDNA synthesis of genetic material (e.g., the genetic complexes) of the population of target cells, thereby generating a genetic product 80 associated with each individual cell that can be further analyzed downstream (e.g., genetic sequencing). Synthesis of cDNA from genetic complexes containing mRNA via reverse transcription can be performed by adding a series of process reagents to the array of wells in a predetermined sequence, and is preferably automated by at least one subcomponent of the system 100. In a preferred variation, the series of process reagents can be added to the array of wells at a set time, volume, velocity, and temperature using a program executed by a processor of the fluid delivery module. The method can further comprise receiving information regarding a sample preparation protocol in Block S242. Block S242 is preferably performed before Block S240, such that an automated system can be prepared to process and analyze a biological sample based upon the information. For example, Block S242 can enable automatic alignment of reagent chambers of a set of reagent chambers of a fluid delivery module, with a fluid reservoir 160 configured to deliver processing reagents into a array of wells. In a specific example, a sequence of alignment commands can be generated that control rotation of a cylindrical cartridge containing isolated processing reagents, thereby automating processing of the biological sample according to the sample preparation protocol. Block S242 can alternatively be performed before or after any suitable step of the method 200, and can be used in coordination with information collected from any other step of method 200 and/or system 100. For instance, Block S242 can allow a user to input information about the sample preparation protocol, and/or can automatically receive information about the sample preparation protocol using the imaging subsystem 194, as described previously in Block S216. Block S242 can, however, include any other suitable method of receiving information regarding the sample preparation protocol. However, the series of process reagents can be added to the array of wells manually or by any other suitable method to perform any other suitable biochemical process.

2.5 Method—Removing Genetic Material from the Array of Wells

Block S250 recites: removing genetic material from the array of wells, which functions to collect the genetic material from the wells for downstream processing. In variations, genetic material including portions of genetic complexes and genetic products generated in Block S240 can include any biological material containing identifying information for the target cell (e.g., synthetic proteins, natural proteins, nucleic acids, a biomarker, a byproduct of a biochemical reaction, etc.). Prior to removal from the array of wells, the genetic material can be coupled to the population of particles, floating in the solution within the well cavity 128, attached to a region of the interior surface 130 of the well cavity 128, or in any suitable location within the well or in relation to any other suitable subcomponent within the well. In a first variation, the genetic material includes the raw intracellular genetic content from lysed cells (e.g., protein, mRNA, DNA, proteins). In a second variation, the genetic material includes the set of probes 36, either detached from a particle, or coupled to a particle. In a third variation, the genetic material includes the genetic product 80 (e.g., cDNA sequences formed by reverse transcription of the genetic complexes in variations of Block S240). In a fourth variation, the genetic material includes genetic product 80 from Block S240 that has been amplified by polymerase chain reaction (e.g., a cDNA library). However, the genetic material can include any suitable biological materials that can be removed from the array of wells and subsequently analyzed or processed. Block S250 is performed preferably after Block S240 has been completed, but can be performed at any other suitable time in relation to other steps of method 200. In another embodiment, the system 100 can achieve multiple cycles of Blocks S240 and S250 for repeated generation and elution of similar genetic product, thereby permitting preparation of multiple libraries and/or performing sequencing from the same set of single cell-derived genetic complexes.

In a first variation wherein the genetic material remains coupled to the population of particles, removal of the genetic material can be achieved by removing the population of particles from the array of wells. In one variation, the particles can be flushed out from the array of wells by increasing the fluid volume of an extraction fluid within the array of wells (e.g., manually pipetting fluid, flowing a fluid into the array of wells, etc.). In an example, an extraction fluid (e.g., 5-10 mL PBS) can be dispensed into the array of wells in a direction perpendicular to the upper broad surface of the substrate, but can additionally and/or alternatively be dispensed into the array of wells by flowing the extraction fluid along the fluid path through the fluid reservoir in a direction parallel to the upper broad surface of the substrate, wherein the extraction fluid can enter the array of wells through the open surfaces of the wells by diffusion. Additionally and/or alternatively, dispensing the extraction fluid into the array of wells can include applying force to the extraction fluid, thereby altering the velocity of the extraction fluid, to reposition the particles within the wells (e.g., by pipetting up and down into the fluid reservoir, applying a net positive or net negative pressure to the fluid, etc.). In an example, adding a sufficient volume of extraction fluid at a specific fluid velocity (or cycles of at least a first and a second fluid velocity) can expel particles previously submerged within the well cavity 128 through the open surface of the well and into the fluid reservoir, where the particles can be collected for downstream processing (e.g., flowed through the outlet into a collection receptacle, directly retrieved from the reservoir, etc.). In a second variation, the particles can be removed from the array of wells by inverting the substrate (e.g., rotating the substrate about its transverse axis passing through the midpoint of the substrate by 180°) and incubating the substrate for a time period of up to 60 minutes (e.g., approximately 10, 20, 30, 40, 50, 60 minutes). In variations wherein the fluid reservoir is sealed by the first plate 150 (as described in a previous section), particles can exit the array of wells through the open surfaces of the wells and into the fluid reservoir by gravitational force, however, the particles can egress from the array of wells into any other suitable collection receptacle. In a third variation, the particles can be directly extracted from the array of wells, using the extraction module. Additionally and/or alternatively, the speed of extraction of the particles can be accelerated by additional steps, including: centrifuging the substrate, physically agitating the substrate (e.g., shaking, vibrating), increasing and/or decreasing fluid volume into the array of wells, applying a force to the particles (e.g., magnetic, electric, physical), or any other suitable method of removal.

In a second variation wherein the genetic material remains coupled to the population of particles, genetic material can be removed by separating the genetic product 80 from the particle within the well, and pipetting the fluid from the wells, leaving the particle within the well. In an example, the genetic complexes are bound to the particle by a reversible biochemical bond, such as a photo-cleavable linker, wherein the linker is reversibly attachable to the particle and can be removed by exposing the particles to specific wavelengths of light (e.g., visible light spectrum, ultraviolet spectrum). However, various chemistries can be used to controllably remove (or attach) the probe to the particle, the well, or any other suitable surface for downstream analysis. In a specific example, uniform light originating from the optical subsystem described in Section 1 can provide uniform illumination of the array of wells from above the substrate proximal the first broad face of the substrate, and into the well cavities through the open surfaces of the wells. In this example, ultraviolet light ranging from 300-400 nm (e.g., 365 nm) can be irradiated into the array of wells for up to 30 minutes (e.g., approximately 5, 10, 20, 30 minutes). In a preferred variation, the thermal control module can include a reflective surface arranged below the substrate at the second broad face (lower surface), directly opposing the first broad face through which the ultraviolet light passes, thereby reflecting incident light back into the well and illuminating the entire bead for uniform and simultaneous photo-cleaving of the genetic complexes from the population of particles. However, uniform irradiation of the population of particles contained within the wells can be achieved by any other suitable method, including: rotating the beads within the wells by gently shaking or rotating the substrate during exposure, and using fluid flow across the fluid reservoir 160 in conjunction with the pressure system to manipulate rotation of the beads within the wells. Furthermore, any wavelength or combination of wavelengths of light or can be used to illuminate the population of particles to perform chemistry sensitive to light. In addition, the intensity of the incident light beam can be of any suitable intensity. In this variation wherein optical illumination is used to separate the genetic product 80 from the population of particles within the well, the thermal control module can be used to control the temperature of the array of wells to minimize effects of heating of the solution with the well cavities to preserve the quality of the genetic product. Furthermore, additional reagents can be added to the array of wells to enhance the efficiency or aid in the performance of photo-cleaving chemistries, such as reagents to increase speed and/or efficiency of removal, or agents to improve viability of genetic material during removal.

In an alternative variation of Block S250, separating the genetic material from the particle can further include, instead of removing the genetic material from the well, removing the bare particle from the well, thereby leaving the genetic material in individual wells for further processing. In this variation, the genetic material can be left freely floating within the well cavity 128, or can be immobilized within the well cavity 128. The particles can be removed by methods in previously described variations (e.g., magnet), leaving the genetic material to couple to the interior surface 130 of the well cavity 128. As described in Section 1, the interior surface 130 of the well cavity 128 can include surface features, wherein small molecules can be physically, energetically, or chemically entrapped, and/or surface features wherein small molecules bind with high affinity (higher binding affinity than to the particle). In a specific example, the genetic material can get physically entrapped by a set of ridges or protrusions within the walls of each well. In another specific example, the genetic material can include a functional linker incorporated from the conjugated probe (e.g., biotin protein), and can be configured to bind to streptavidin that has been previously coated on the interior surface 130 of the wells. In another specific example, the genetic material can bind to affinity microspheres/agents lining the surface of the wells. However, genetic material can be processed in any suitable manner.

Figure 34:
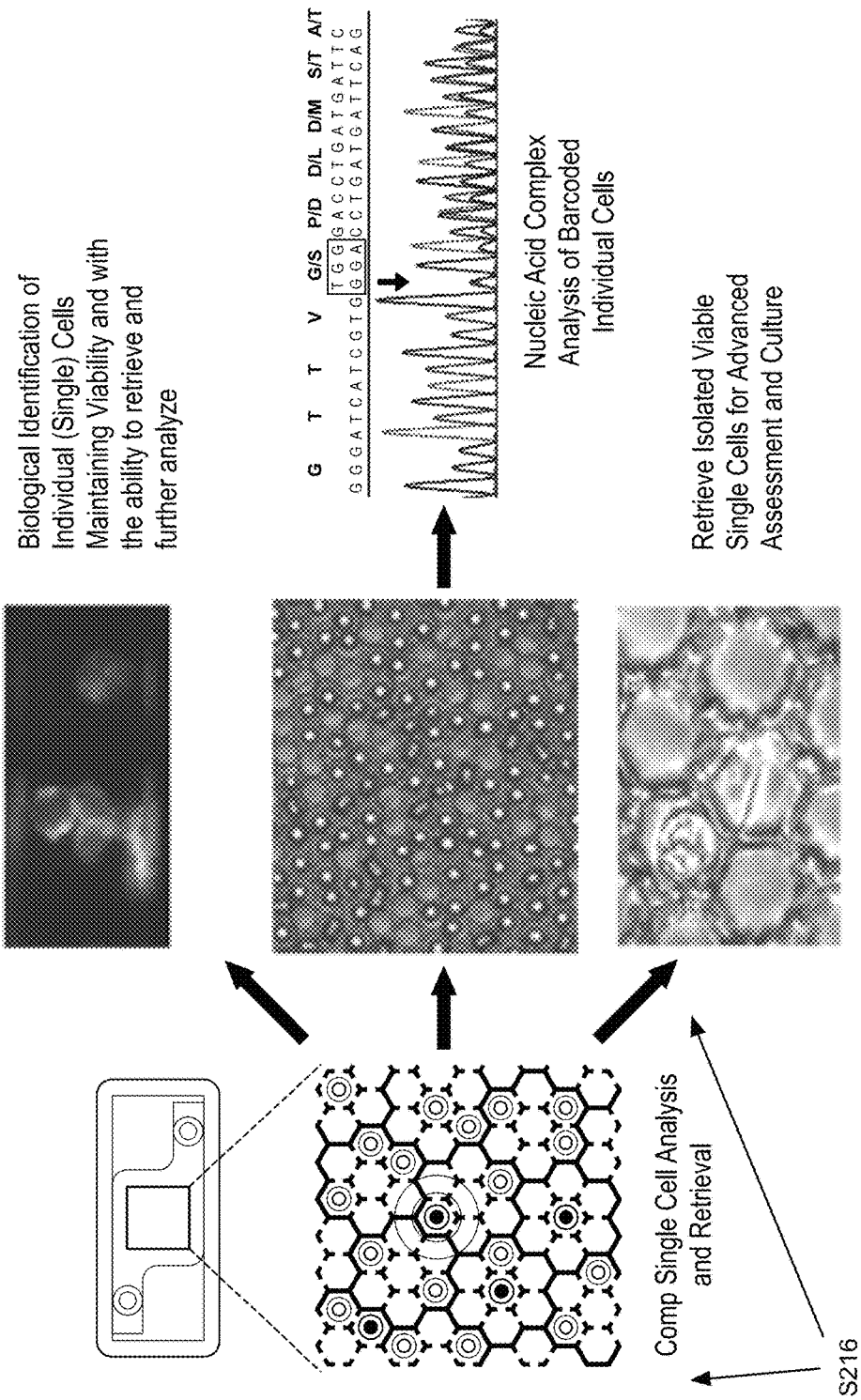
FIG. 34 depicts a schematic of three variations of a portion of an embodiment of a method for isolating and analyzing cells.

Downstream analysis of captured target cells and/or genetic material derived from captured target cells can include any one or more of: harvesting contents of the set of wells (e.g., cells, intracellular content), culturing cells captured at the set of wells, detecting biomarkers exhibited by the cell population (e.g., using fluorescent detection), performing a quantitative analysis (e.g., a quantitative analysis of mRNA expression), characterizing a cell phenotype (e.g., a cancer cell phenotype) based upon biomarker expression, providing a recommended therapy based upon characterization of a cell phenotype, performing flow cytometry with captured cells of the cell population, and performing any other suitable analysis. In a preferred application, wherein genetic material, specifically cDNA produced in Block S240, is used for RNA sequencing, genetic material can be further processed to generate cDNA libraries containing genetic material of specific fragment sizes and quality by performing: exonuclease treatment, pre-amplification PCR, SPRI cleanup, and tagmentation. Furthermore, data collected using system 100 and through implementation of variations of method 200 can be used to generate and utilize single-cell targeted panels including: genotyping libraries, CRISPR pools, immune profiling, pathway analysis, drug screening, and lineage tracing (FIG. 34). However, variations of method 200 can additionally or alternatively include any other suitable steps or blocks that facilitate reception, processing, and/or analysis of the cell population in at least one of single-cell format and single-cluster format.

The system 100 and method 200 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for isolating and analyzing a population of target cells comprising:
   receiving a population of target cells into an array of wells defined at a surface plane of a substrate, wherein each well in the array of wells extends perpendicular to and below the surface plane into the substrate and is in an unoccupied state;
   achieving a particle-accessible state for a first subset of wells of the array of wells comprising at least a first well and a second well, wherein a first target cell of a population of target cells is received below the surface plane through an open end of the first well, and a second target cell of the population of target cells is received below the surface plane and through an open end of the second well;
   distributing a population of particles into the array of wells, wherein each particle of the population of particles is coupled to a probe having a binding affinity for a biomolecule associated with the population of target cells;
   upon distributing the population of particles into the array of wells,
      achieving an ideal state for at least the first well of the first subset of wells in the particle-accessible state, wherein achieving the ideal state comprises receiving a first particle of the population of particles into the first well below the surface plane, thereby colocalizing the first particle with the first target cell within the first well; and
      achieving a particle-saturated state for at least the second well of the first subset of wells in the particle accessible state, wherein achieving the particle-saturated state comprises receiving at least a second and a third particle of the population of particles into the second well, wherein the second particle is received below the surface plane, and the third particle traverses the surface plane;
   re-distributing a subset of partially retained particles comprising at least the third particle across the array of wells, wherein each partially retained particle in the subset of partially retained particles traverses the surface plane, and wherein re-distributing the subset of partially retained particles comprises:
      flowing a particle distribution fluid along a fluid path through a fluid reservoir spanning the array of wells along the surface plane and in a direction parallel to the surface plane, wherein the particle distribution fluid egresses at least the third particle traversing the surface plane from the second well, thereby transitioning the second well from the particle-saturated state to an ideal state; and
   processing a set of ideal wells of the array of wells comprising at least the first well and the second well, wherein each well in the set of ideal wells is in the ideal state, and wherein each well in the ideal state contains exactly one target cell of the population of target cells and exactly one particle of the population of particles wherein processing the set of ideal wells comprises delivering a process reagent to the set of ideal wells.

2. A method for isolating and analyzing a population of target cells comprising:
   receiving a population of target cells into an array of wells defined at a surface plane of a substrate, wherein each well in the array of wells extends perpendicular to and below the surface plane within the substrate;
   achieving a particle-accessible state for a first subset of wells of the array of wells, wherein a first well of the first subset of wells receives a first target cell of the population of target cells below the surface plane through an open end of the first well;
   after receiving the population of target cells into the array of wells, distributing a population of particles into the array of wells, wherein each particle of the population of particles is coupled to a probe having a binding affinity for a biomolecule associated with the population of target cells;
   upon distributing the population of particles into the array of wells,
      achieving a particle-saturated state for at least the first well of the first subset of wells, wherein achieving the particle-saturated state comprises receiving, into the first well, a first particle below the surface plane and a partially retained particle traversing the surface plane;
   re-distributing a subset of partially retained particles across the array of wells, wherein each partially retained particle in the subset of partially retained particles traverses the surface plane, wherein re-distributing the subset of partially retained particles comprises:
      flowing a particle distribution fluid along a fluid path through a fluid reservoir spanning the array of wells along the surface plane and in a direction parallel to the surface plane, wherein the particle distribution fluid egresses the partially retained particle traversing the surface plane from the first well, thereby transitioning the first well from the particle-saturated state to an ideal state; and processing a set of ideal wells of the array of wells comprising at least the first well, wherein each well in the set of ideal wells is in the ideal state and contains exactly one target cell of the population of target cells and exactly one particle of the population of particles, wherein processing the set of ideal wells comprises delivering a process reagent to the set of ideal wells.

3. The method of claim 2, further comprising:
upon egressing the partially retained particle from the first well, transmitting the partially retained particle downstream of the fluid path across the array of wells; and
receiving the partially retained particle into a downstream well, wherein the downstream well is in the particle-accessible state, and wherein the partially retained particle is received below the surface plane into the downstream well, thereby transitioning the downstream well from a particle-accessible state to an ideal state.

4. The method of claim 2, further comprising, upon distributing the population of particles into the array of wells,
achieving an ideal state for at least a second well of the first subset of wells, comprising receiving, into the second well, exactly one particle of the population of particles below the surface plane.

5. The method of claim 2, wherein receiving the population of target cells into the array of wells further comprises flowing a cell distribution fluid along the fluid path, wherein the cell distribution fluid egresses a subset of partially retained target cells across the array of wells, wherein each partially retained target cell in the subset of partially retained target cells traverses the surface plane.

6. The method of claim 5, further comprising:
upon receiving the population of target cells into the array of wells,
achieving a cell-saturated state for a second subset of wells of the array of wells, wherein achieving the cell-saturated state comprises receiving, into at least a first cell-saturated well of the second subset of wells, a target cell below the surface plane and a partially retained target cell traversing the surface plane; and
transitioning at least the first cell-saturated well from the cell-saturated state to the particle-accessible state by flowing the cell distribution fluid along the fluid path, wherein the cell distribution fluid egresses the partially retained target cell from the first cell-saturated well.

7. The method of claim 6, further comprising:
upon egressing the partially retained target cell from the first cell-saturated well, transmitting the partially retained target cell downstream of the fluid path across the array of wells; and
receiving the partially retained target cell into an unoccupied well downstream of the first cell-saturated well, wherein the partially retained cell is received below the surface plane of the unoccupied well, thereby transitioning the unoccupied well from an unoccupied state to the particle-accessible state.

8. The method of claim 2, wherein flowing the particle distribution fluid along the fluid path comprises, with a flow control module coupled to the fluid reservoir, controlling a flow direction of the particle distribution fluid, wherein the flow direction alternates between a first direction and a second direction opposing the first direction.

9. The method of claim 2, wherein flowing the particle distribution fluid along the fluid path comprises, with a flow control module coupled to the fluid reservoir, controlling a flow rate of the particle distribution fluid, wherein the flow rate is greater than 0.5 mL/min.

10. The method of claim 2, wherein the first biomolecule is a ribonucleic acid and the probe of each particle in the population of particles comprises a nucleotide sequence configured to bind to nucleic acid content.

11. The method of claim 2, wherein processing the set of ideal wells comprises:
within at least the first well of the set of ideal wells, releasing the biomolecule from the first target cell, comprising:
flowing a process reagent along the fluid path and into the array of wells, wherein the temperature of the array of wells is maintained below 15° C. with a thermal control module coupled to the substrate; and
upon releasing the first biomolecule from the first target cell, binding the first biomolecule to a first probe of the first particle to generate a first genetic complex coupled to the first particle.

12. The method of claim 11, further comprising:
within the first well of the set of ideal wells, performing a biochemical process upon the first genetic complex.

13. The method of claim 12, wherein performing the biochemical process comprises performing reverse transcription within at least the first well of the set of ideal wells, thereby producing, within the first well, a first nucleotide sequence associated with the first genetic complex.

14. The method of claim 11, wherein processing the set of ideal wells further comprises removing at least a portion of the first genetic complex from the first well of the set of ideal wells.

15. The method of claim 14, wherein the probe of each particle in the population of particles is coupled to a particle of the population of particles by a photocleavable linker, wherein removing at least a portion of the first genetic complex from the first well of the set of ideal wells comprises illuminating the array of wells with at least one wavelength of light to release the portion of the first genetic complex from the first particle.

16. The method of claim 14, wherein the wavelength of light is between 300 and 400 nm.

17. The method of claim 11, wherein the first probe includes a first unique identifier for the first probe, and wherein generating the first genetic complex associates the first unique identifier with the first target cell.

18. The method of claim 2, wherein each well of the array of wells is configured to achieve the ideal state, wherein the length of each well is between 20 and 75 micrometers, and the width of each well is between 20 and 30 micrometers.

19. The method of claim 2, wherein each well of the array of wells defines a prismatic volume within the substrate, and wherein the wells are arranged in a hexagonal close-packed configuration spanning the surface plane of the substrate.

20. The method of claim 2, wherein an open end of each well in the array of wells defines a hexagon, wherein the horizontal cross-section of the open end of each well is aligned with the surface plane.

* * * * *

UNITED STATES PATENT AND TRADEMARK OFFICE
CERTIFICATE OF CORRECTION

PATENT NO. : 10,391,492 B2
APPLICATION NO. : 16/115059
DATED : August 27, 2019
INVENTOR(S) : Kalyan Handique et al.

Page 1 of 1

It is certified that error appears in the above-identified patent and that said Letters Patent is hereby corrected as shown below:

In the Claims

Column 56, Line 26:
In Claim 1, after "of particles", insert --,--

Column 58, Line 45:
In Claim 16, delete "claim 14," and insert --claim 15,-- therefor Signed and Sealed this
Fifth Day of May, 2020

Andrei Iancu
*Director of the United States Patent and Trademark Office*